United States Patent
Johnson et al.

(10) Patent No.: US 7,144,912 B2
(45) Date of Patent: Dec. 5, 2006

(54) PYRROLE-TYPE COMPOUNDS, COMPOSITIONS, AND METHODS FOR TREATING CANCER, TREATING VIRAL DISEASES AND CAUSING IMMUNOSUPPRESSION

(75) Inventors: Roy A. Johnson, Sausalito, CA (US); Giorgio Attardo, Laval (CA)

(73) Assignee: Gemin X Biotechnologies Inc., Montreal (CA)

( * ) Notice: Subject to any disclaimer, the term of this patent is extended or adjusted under 35 U.S.C. 154(b) by 0 days.

(21) Appl. No.: 10/484,652

(22) PCT Filed: Jul. 18, 2002

(86) PCT No.: PCT/CA02/01104

§ 371 (c)(1),
(2), (4) Date: Jul. 26, 2004

(87) PCT Pub. No.: WO03/008410

PCT Pub. Date: Jan. 30, 2003

(65) Prior Publication Data

US 2005/0049292 A1    Mar. 3, 2005

Related U.S. Application Data

(60) Provisional application No. 60/305,870, filed on Jul. 18, 2001.

(51) Int. Cl.
*A61K 31/403* (2006.01)
*C07D 487/00* (2006.01)
*C07D 209/02* (2006.01)
*C07D 209/04* (2006.01)

(52) U.S. Cl. ............ 514/410; 514/414; 548/421; 548/466

(58) Field of Classification Search ............. None
See application file for complete search history.

(56) References Cited

U.S. PATENT DOCUMENTS

| | | | |
|---|---|---|---|
| 2,673,855 A | 3/1954 | Nager | |
| 5,691,334 A | 11/1997 | Doria et al. | |
| 5,847,127 A | 12/1998 | D'Alessio et al. | |
| 6,369,096 B1 | 4/2002 | D'Alessio et al. | |
| 6,407,244 B1* | 6/2002 | Murthy et al. | 546/276.7 |
| 6,602,879 B1* | 8/2003 | Murthy et al. | 514/277 |
| 6,638,968 B1 | 10/2003 | Kim et al. | |
| 2003/0119894 A1* | 6/2003 | Murthy et al. | 514/414 |

FOREIGN PATENT DOCUMENTS

| | | |
|---|---|---|
| CA | 2155096 | 6/1995 |
| JP | 55162758 | 8/1986 |
| JP | 61-280429 | 12/1988 |
| JP | 02250828 | 10/1990 |
| JP | 2250828 | 10/1990 |
| JP | 09-030967 | 2/1997 |
| JP | 10-120562 | 5/1998 |
| JP | 10-120563 | 5/1998 |
| JP | 11-209283 | 8/1999 |
| WO | WO-98/11894 | 3/1998 |
| WO | WO-98/40380 | 9/1998 |
| WO | WO-99/15690 | 4/1999 |
| WO | WO-99/29309 | 8/1999 |
| WO | WO-99/40069 | 8/1999 |

OTHER PUBLICATIONS

Boger, et al. "Total Synthesis of Prodigiosin, prodigiosene, and Desmethoxyprodigiosin," J. Org. Chem., vol. 53, pp. 1405-1415, 1988.*
Nakai, et al. Transplantation Proceedings, vol. 32(6), pp. 1324-1325 (2000).*
Gerber, et al., Journal of Organic Chemistry, vol. 37(6), 1176-1179, (1979).*
Furstner, et al. Journal of Organic Chemistry, vol. 64, pp. 8275-8280, (1999).*
Yamamoto, et al. Hepatology, vol. 30(4), pp. 894-902 (1999).*
Boger and Patel, 1988, "Total Synthesis of Prodigiosin, Prodigiosene, and Desmethosyprodigiosin: Diels-Alder Reactions of Heterocyclic Azadienes and Development of an Effective Palladium(III)-Promoted 2,2'-Bipyrrole Coupling Procedure", J. Org. Chem. 53(7):1405-1415.
Abel, et al., 2000, "Aggregate formation from 3-alkylindoles; amphiphilic models for interfacial helix anchoring groups," Chem. Comm. 433-434.
Anderson, et al., 1985, "The Synthesis of 3-Substituted Pyrroles from Pyrrole," Synthesis, 353-364.

(Continued)

*Primary Examiner*—Kamal A. Saeed
*Assistant Examiner*—Nyeemah Grazier
(74) *Attorney, Agent, or Firm*—Wilmer Cutler Pickering Hale and Dorr LLP

(57) ABSTRACT

The present invention relates to novel Pyrrole-Type compounds, compositions comprising Pyrrole-Type compounds, and methods useful for treating or preventing cancer or a neoplastic disorder comprising administering a Pyrrole-Type compound. The compounds, compositions, and methods of the invention are also useful for inhibiting the growth of a cancer cell or neoplastic cell. The present invention also relates to novel Pyrrole-Type compounds, compositions, and methods useful for treating or preventing a viral infection. The compounds, compositions, and methods of the invention are also useful for inhibiting the replication and/or infectivity of a virus. The present invention also relates to novel Pyrrole-Type compounds, compositions, and methods useful for causing immunosuppression. The present invention also relates to novel Pyrrole-Type compounds, compositions, and methods useful for treating or preventing an autoimmune disease.

28 Claims, 1 Drawing Sheet

OTHER PUBLICATIONS

Figure 1:
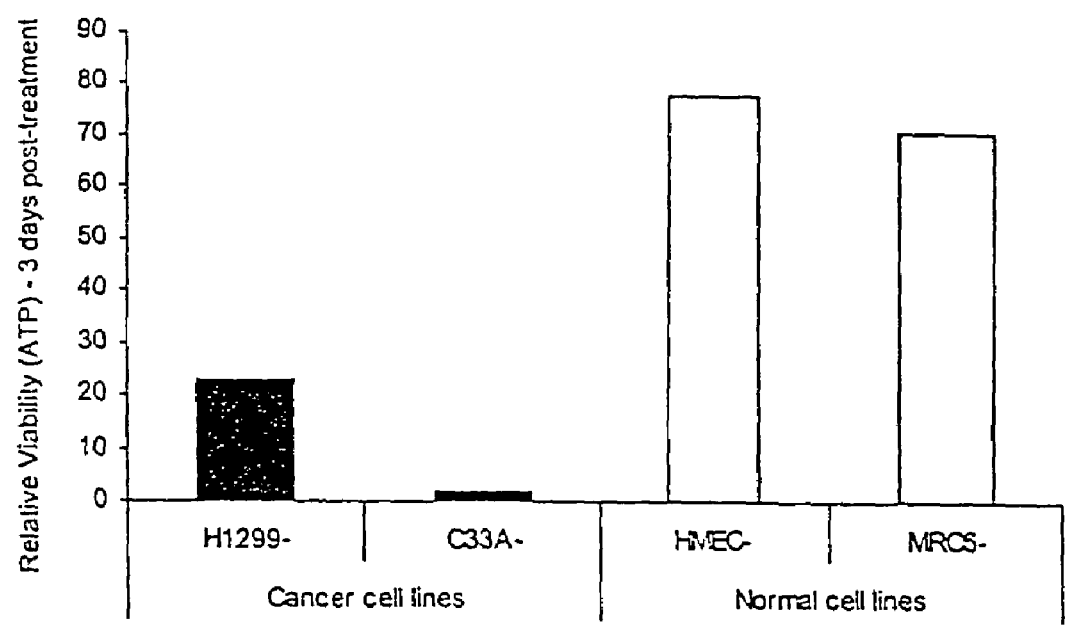

Applebaum, 1992, "The role of the immune system in the pathogenesis of cancer", Semin. Oncol. Nurs. 8(1):51-62.
Azuma, et al., 2000, "Induction of apoptosis of activated murine splenic T cells by cyproprodiglosin hydrochloride, a novel immunosuppressant", Immunopharmacology 46(1):29-37.
Birkeland et al., 2000, "Cancer risk in patients on dialysis and after renal transplantation", Lancet 355(8218):1886-7.
Blake, et al. 1990, "A short synthesis of prodiglosin analogues," J. Chem. Soc., Chem. Comm. 734-736.
Boger and Patel, 1987, "Total Synthesis of Prodigiosin", Tetrahedron Lett. 28:2499-2502.
Botti et al., 1998, "Immunosupressive factors: role in cancer development and progession", Int'l. J. Biol. Mark. 13(2):51-69.
Castro, A. et al., "Antimicrobial Properties of Pyrrole Derivatives," J. Med. Chem., vol. 10(1), pp. 29-32 (Jan. 1967).
Cortesina et al., 1993, "Immunomodulation therapy for squamous cell carcinoma of the head and neck", Head Neck. 15(3):266-70.
D'Alessio and Rossi, 1996, "Short Synthesis of Undecyprodigiosine. A New Route to 2,2'-Bipyrrolyl-Pyrromethene Systems", Synlett 6:513-514.
D'Alessio, R., et al., "Synthesis and Immunosuppressive Activity of Noval Prodigiosin Derivatives," J. Med. Chem., vol. 43, pp. 2557-2565 (2000).
Duc, et al. 1992, "Methyl (E)-4-Chloro-3-methoxy-2-butenoate: An Extremely Versatile Four Carbon Building Block," Synthesis, 391-394.
Furstner et al., 1998, "Platinum- and Acid-Catalyzed Enyne Metathesis Reactions: Mechanistic Studies and Applications to the Syntheses of *Streptorubin* B and Metacycloprodigiosin", J. Am. Chem. Soc. 120:8305-8314.
Furstner, A., et al., "Total Synthesis and Structural Refinement of the Cyclic Tripyrrole Pigment Nonylprodigiosin," J. Org. Chem., vol. 64(22) pp. 8275-8280 (1999).
Furstner, et al., 1998, "Total Synthesis of Roseophilin," J. Am. Chem. Soc. 120:2817-2825.
Gerber and Lechevalier, 1976, "Prodiginine (Prodigiosin-Like) Pigments from *Streptomyces* and Other Aerobic Actinomycetas", Can. J. Microbiol. 22:658-667.
Gerber and Stahly, 1975, "Prodiginine (Prodigiosin-Like) Pigments from *Streptoverticillium rubrireticuli*, an Organism That Causes Pink Staining of Polyvinyl Chloride", Appl. Microbiol. 30:807-810.
Gerber et al., "Biosynthesis of Prodiginines, $^{13}$C Resonance Assignments and Enrichment Patterns in Nonyl- Cyclononyl-, Methylcyclodecyl-, and Butylcycloheptylprodiginine Produced by Actinomycete Cultures Supplemented with $^{13}$C-Labeled Acetate and $^{15}$N-Labeled Nitrate", Can. J. Chem. 56:1155-1163.
Gerber, 1973, "Minor Prodiginine Pigments from Actionomadura madurae and Actinomadura pelletien", J. Hetarocycl. Chem. 10:925-929.
Gerber, 1975, "A New Prodiginine (Prodigiosin-Like) Pigment from *Streptomyces*. Antimalarial Activity of Several Prodiginines", J. Antibiotics 28:194-199.
Gerber, 1975, "Prodigiosin-Like Pigments", CRC Crit. Rev. Microbiol. 3:469-485.
Goping et al., "Regulated Targeting of BAX to Mitochondria", J. Cell Biol. 143:207-215.
Guseva and Balshin, 1992 "Comparative Efficacy of Prodigiosan and Proper-Myl Action on Neutrophil Phagocytosis in Acute Myeloblastic Leukemia", Antibiot. Khimioter. 37:44-46 (in Russian w/English abstract).
Guseva and Tishenko, 1989, "The Effect of Prodigiosan on Antibody-Dependent Cytotoxicity of Neutrophils in Chronic Myeloid Leukemia", Vopr. Onkol. 35:30-34 (in Russian w/English abstract).
Hearn, W., et al., "Prodigiosene [5-(2-Pyrryl)-2,2'-dipyrrylmethene] and Some Substituted Prodigiosenes," J. Org. Chem., vol. 35(1) pp. 142-146 (Jan. 1970).
Hojo et al., 1999, "Cyclosporina Induces Cancer Progression by a Cell-Autonomous Mechanism", Nature 397:530-534.
http://dbs.p.kanazawa-u.ac.ip/-seika/home-e.html Faculty of Pharmaceutical Science at the University of Kanazawa (2000).

Korsmeyer, 1992, "Bcl-2: A Repressor of Lymphocyte Death", Immunol. Today 13:285-288.
Laatsch and Thomson, 1983, "A Revised Structure for Cycloprodigiosin", Tetrahedron Lett. 24:2701-2704.
Laatsch et al., 1991, "Butyl-meta-Cycloheptylprodiginine—a Revision of the Structure of the Former Ortho-Isomer", J. Antibiot. 44:187-191.
Marshall et al., 1999, "Epstein-Barr Virus Encodes a Novel Homolog of the bcl-2 Oncogene That Inhibits Appoptosis and Associates with Bax and Bak", J. Virol. 73:5181-5185.
Matsunaga et al., 1986, "Bioactive Marine Metabolites. VIII. Isolation of an Antimicrobial Blue Pigment from the Bryozoan Bugula dentata", Experientia 42:84.
Melvin, M. et al., "DNA Binding by 4-Methoxypyrrolic Natural Products," J. Org. Chem., vol. 64(18), pp. 6861-6869 (1999).
Mitsuya et al., 1991, "Targeted Therapy of Human Immunodeficiency Virus-Related Disease", FASEB J. 5:2369-2381.
Molecular Biology of the Cell (2ed. 1989) edited et al., Garland Publishing, Inc.:New York, pp. 727-761 and 1203-1215.
Montaner et al., 2000, "Prodigiosin from the supernatant of *Serratia marcescens* induces apoptosis in haematopoletic cancer cell lines", Br. J. Pharmacol. 131(3):585-93.
Mortellaro et al., 1999, "New Immunosuppressive Drug PNU156804 Blocks IL-2 Dependent Proliferation and NF-.kappa.B and AP-1 Activation", J. Immunol. 162:7102-7109.
Nakamura et al., 1986, "Selective Suppression by Prodigiosin of the Mitogenic Response of Murine Splenocytes", J. Antibiotics 39:1155-1159.
Ng and Shore, 1998, "Bcl-X.sub.L. Cooperatively Associates with Bap31 Complex in the Endoplasmic Reticulum, Dependent on Procaspase-8 and Ced-4 Adaptor", J. Biol. Chem. 273:3140-3143.
Ng et al., 1997, "p 28 Bap31, a Bcl-2/Bcl-X.sup.L—and Procaspase-8-Associated Protein In the Endoplasmic Reticulum", J. Cell. Biol. 139:327-338.
Nguyen et al., 1998, "E1A-Induced Processing of Procaspase-8 Can Occur Independently of FADD and is Inhibited by Bcl-2", J. Biol. Chem. 273-33099-33102.
Nicot et al., 1997, "Activation of Bcl-2 Expression in Human Encothelial Cells Chronically Expressing the Human T-Cell Lymphotropic Virus Type I", Virol. 236:47-53.
Penn, 2000, "Cancers in renal transplant recipients", Adv. Ren. Replace. Ther. 7(2):147-56.
Piontek and Porschen, 1994, "Growth Inhibition of Human Gastrointestinal Cancer Cells by Cyclosporin A", J. Cancer Res. Clin. Oncol. 120:695-699.
Rapoport and Holden, 1962, "The Synthesis of Prodigiosin", J. Am. Chen. Soc. 84:635-642.
Rubinstein et al., 1990, "Comparison of In Vitro Anticancer-Drug-Screening Data Generated with a Tetrazolium Assay versus a Protein Assay Against a Diverse Panel of Human Tumor Cell Lines", J. Natl. Cancer Inst. 82:1113-1118.
Shapoyalova, 1972, "Effect of Antitumor Antibiotics on Resistance to Bacterial Infections of Animals with Transplanted Lymphadenosis NK/LI", Antibiotiki 17:339-343 (In Russian w/English abstract).
Skehan et al., 1990, "New Colorimetric Cytotoxicity Assay for Anticancer-Drug Screening", J. Natl. Cancer Inst. 82:1107-1112.
Strauss and Berger, 1983, "Methylosin A und B, Pigmente aus *Methylosinus trichosporium*", Zeitschr. fur Allgemeine Mikrobiologie 23:661-668 (in German w/English abstract).
Swinnen et al., 2000, "Transplantation-related lymphoproliferative disorder: a model for human immunodeficiency virus-related lymphomas", Semin. Oncol, 27(4):402-8.
The Merck Index (12th ed., 1996) entry 7948, p. 1334.
Thomas and Banks, 1998, 1998, "Inhibition of Bak-Induced Apoptosis by HPV-18 E6", Oncogene 17:2943-2954.
Thomas and Banks, 1999, "Human Papillomarvirus (HPV) E6 Interactions with Bak are Conserved amongst E6 Proteins from High and Low Rish HPV Types", J. Gen. Virol. 80:1513-1517.
Tsao et al., 1985, "Identification of a Red Pigment from *Streptomyces coelicolor* A3(2) as a Mixture of Prodigiosin Derivatives", J. Antibiotics 38:128-131.

Tsujimoto et al., 1984, "Cloning of the Chromosome Breakpoint of Neoplastic B Cells with the t(14;18) Chromosome Translocation", Science 226:1097-1099.

Tsukahara et al., 1999, "Induction of Bcl-x.sub.L Expression by Human T-Cell Leukemia Virus Type 1 Tax through NF-.kappa.B in Apoptosis-Resistant T-Cell Transfectants with Tax", J. Virol. 73:7981-7987.

Wasserman et al., 1961, "Der Prodigiosin-Ahnllche Pilzfarbstoff aus *Streptomyces longisporus* ruber", Angew. Chem. 73:467 (In German).

Wasserman et al., 1969, "The Synthesis of Metacycloprodigiosin", J. Am. Chem. Soc. 91:1264-1265.

Wasserman et al., 1976, "The Structure of Matacycloprodigiosin", Tetrahedron 32:1855-1861.

Wasserman et al., 1976, "The Synthesis of Metacycloprodigiosin", Tetrahedron 32:1867-1871.

Wasserman et al., 1976, "Undecylprodigiosin", Tetrahedron 32:1851-1854.

Wasserman et al., 1984, "The synthesis of (±)-cycloprodigiosin," Tet. Lett., 25(13), 1387-1388.

Wasserman, H. et al., "Biosynthesis of Prodigiosin," J. Amer. Chem. Soc., vol 95(20), pp. 6874-6875 (Oct. 1973).

Waters, 1998, "Chloroquine-Resistance-Discovering the Missing Link?", Nature Med. 4:23-24.

Yayon et al., 1984, "Identification of the Acidic Compartment of *Plasmodium falciparum*-Infected Human Erythrocytes as the Target of the Antimalarial Drug Chloroquine", EMBO J. 3:2695-2700.

Barbgallo et al., 1979, "Cytological Activity of Prodigiosin by Allium cepa L. Test", Riv. Biol. Norm. Patol. 5:25-31 (in Italian w/English abstract).

Hong et al., 1999, "Cloning and Functional Analysis of Infectious Pancreatic Necrosis Virus VP5: A Novel Bcl-2 Family with Regulation of Viral Expression and Anti-Cell Death Activity", Cold Spring Harbor Symposium on Programmed Cell Death, Sep. 29-Oct. 3, 1999, p. 93.

Magae et al., 1996, "Effect of Metacycloprodigiosin, an Inhibitor of Killer T Cells, on Murine Skin and Heart Transplants," J. Antibiotics 86-90.

Myasoedov et al., 1987, "Topical Application of Chemopreparations and Embolization of the Blood Vessels in the Complex Treatment of Tumors", Klin. Khir. 4:7-9 (in Russian with English abstract).

* cited by examiner

PYRROLE-TYPE COMPOUNDS, COMPOSITIONS, AND METHODS FOR TREATING CANCER, TREATING VIRAL DISEASES AND CAUSING IMMUNOSUPPRESSION

This application claims the benefit of U.S. Provisional Application No. 60/305,870, filed Jul. 18, 2001, which is incorporated by reference herein in its entirety.

1. FIELD OF THE INVENTION

The present invention relates to Pyrrole-Type compounds, compositions comprising Pyrrole-Type compounds, and methods useful for treating or preventing cancer or a neoplastic disorder comprising administering a Pyrrole-Type compound. The compounds, compositions, and methods of the invention are also useful for inhibiting the growth of a cancer cell or neoplastic cell. The present invention also relates to Pyrrole-Type compounds, compositions, and methods useful for treating or preventing a viral infection. The compounds, compositions, and methods of the invention are also useful for inhibiting the replication or infectivity of a virus. The present invention also relates to Pyrrole-Type compounds, compositions, and methods useful for causing immunosuppression. The compounds and methods are also useful for treating or preventing an autoimmune disease.

2. BACKGROUND OF THE INVENTION

2.1. Cancer and Neoplastic Disease

Cancer affects approximately 20 million adults and children worldwide, and this year, more than 9 million new cases will be diagnosed (International Agency for Research on Cancer; www.irac.fr). According to the American Cancer Society, about 563,100 Americans are expected to die of cancer this year, more than 1500 people a day. Since 1990, in the United States alone, nearly five million lives have been lost to cancer, and approximately 12 million new cases have been diagnosed.

Currently, cancer therapy involves surgery, chemotherapy and/or radiation treatment to eradicate neoplastic cells in a patient (see, for example, Stockdale, 1998, "Principles of Cancer Patient Management", in *Scientific American: Medicine*, vol. 3, Rubenstein and Federman, eds., Chapter 12, Section IV). All of these approaches pose significant drawbacks for the patient. Surgery, for example, may be contraindicated due to the health of the patient or may be unacceptable to the patient. Additionally, surgery may not completely remove the neoplastic tissue. Radiation therapy is effective only when the irradiated neoplastic tissue exhibits a higher sensitivity to radiation than normal tissue, and radiation therapy can also often elicit serious side effects. (Id.) With respect to chemotherapy, there are a variety of chemotherapeutic agents available for treatment of neoplastic disease. However, despite the availability of a variety of chemotherapeutic agents, chemotherapy has many drawbacks (see, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, many tumor cells are resistant or develop resistance to chemotherapeutic agents through multi-drug resistance.

Tamura et al., JP93086374, discloses metacycloprodigiosin and/or prodigiosin-25C as being useful for treating leukemia, but provides data for only prodigiosin-25C activity against L-5178Y cells in vitro. Hirata et al., JP-10120562, discloses the use of cycloprodigiosin as an inhibitor of the vacuolar ATPase proton pump and states that cycloprodigiosin may have anti-tumor enhancing activity. Hirata et al., JP-10120563 discloses the use of cycloprodigiosin as a therapeutic drug for leukemia, as an immunosuppressant, and as an apoptosis inducer. JP61034403, to Kirin Brewery Co. Ltd, describes prodigiosin for increasing the survival time of mice with leukemia. Boger, 1988, J. Org. Chem. 53:1405–1415 discloses in vitro cytotoxic activity of prodigiosin, prodigiosene, and 2-methyl-3-pentylprodigiosene against mouse P388 leukemia cells. The National Cancer Institute, http://dtp.nci.nih.gov, discloses data obtained from the results of a human-tumor-cell-line screen, including screening of butylcycloheptyl-prodiginine HCl; however, the screen provides no indication that the compounds of the screen are selective for cancer cells (e.g., as compared to normal cells).

Therefore, there is a significant need in the art for novel compounds and compositions, and methods that are useful for treating cancer or neoplastic disease with reduced or without the aforementioned side effects. Further, there is a need for cancer treatments that provide cancer-cell-specific therapies with increased specificity and decreased toxicity.

2.2. Viruses and Disease

In addition to cancer, an enormous number of human and animal diseases result from virulent and opportunistic viral infections (see Belshe (Ed.) 1984 *Textbook of Human Virology*, PSG Publishing, Littleton, Mass.). Viral diseases of a wide array of tissues, including the respiratory tract, CNS, skin, genitourinary tract, eyes, ears, immune system, gastrointestinal tract, and musculoskeletal system, affect a vast number of humans of all ages (see Table 328-2 In: Wyngaarden and Smith, 1988, *Cecil Textbook of Medicine*, 18$^{th}$ Ed., W.B. Saunders Co., Philadelphia, pp. 1750–1753).

Although considerable effort has been invested in the design of effective anti-viral therapies, viral infections continue to threaten the lives of millions of people worldwide. In general, attempts to develop anti-viral drugs have focused on several stages of viral life cycle (See e.g., Mitsuya, H., et al., 1991, FASEB J. 5:2369–2381, discussing HIV). However, a common drawback associated with using of many current anti-viral drugs is their deleterious side effects, such as toxicity to the host or resistance by certain viral strains.

Accordingly, there is a need in the art for anti-viral compounds, compositions, and methods that allow for safe and effective treatment of viral disease without the above-mentioned disadvantages.

2.3. Immunosuppression

The immune system, when working properly, protects an individual from infection and from growth of cancers. In order to carry out these functions, however, the immune system must be able to recognize and mount an attack against foreign antigens (including cancer-specific antigens), but not against self antigens that are present on normal cells throughout the body.

To improve its level of protection, it is possible to stimulate the immune system. Vaccines, including single-protein antigens such as diptheria toxoid, are widely used to generate immunity against a specific antigen and thus a specific disease associated with that antigen. Where general stimulation of the immune system is desired, this type of stimulation can sometimes be achieved using nonspecific agents such as adjuvants, interleukins, interferons, and colony stimulating factors.

Occasionally, the immune system loses its critical ability to distinguish self from non-self antigens. The resulting immunological assault on the individual's own tissues can take the form of autoimmune disease, for example, systemic lupus erythrematosis, Type 1 diabetes, or rheumatoid arthritis. In such a case, or alternatively where the individual is the recipient of a transplanted organ or tissue, suppression rather than stimulation of the immune response is desirable. Non-specific down-regulation of the immune response is typically achieved by treatment with corticosteroids, azathioprine, cyclosporine, tacrolimus (FK506), rapamycin, or mycophenolate mofetil. Certain immunoglobulins, including the monoclonal antibody OKT3, have also been used for this purpose. Suppression of immunity against a specific antigen, called "tolerance induction," may also be possible. Methods that have been used for inducing tolerance against a particular antigen include intravenous or repeated topical administration of the antigen in dilute form, treatment with a very high dose of the antigen, and oral administration of the antigen.

Presently used immunosupressive agents, such as Cyclosporin A and steroids, are potent but can cause severe side effects in a dose dependent manner.

Accordingly, there is a need for new safe compounds, compositions, and methods that are useful for treating diseases that are responsive to immunomodulation.

Citation or identification of any reference in Section 2 of this application is not an admission that such reference is available as prior art to the present invention.

3. SUMMARY OF THE INVENTION

Formula I

The present invention encompasses novel compounds having the general Formula (I):

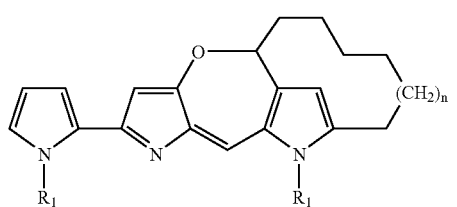

(I)

and pharmaceutically acceptable salts thereof, wherein:

each $R_1$ is independently selected from the group consisting of —H, —CH$_3$, —CH$_2$C$_6$H$_5$, —C(O)OC(CH$_3$)$_3$, and —C(O)OCH$_2$C$_6$H$_5$; and n is an integer ranging from 1 and 5.

The compounds of Formula (I) or a pharmaceutically acceptable salt thereof are useful for treating or preventing cancer or neoplastic disease in a patient in need of such treatment or prevention. The compounds of Formula (I) or a pharmaceutically acceptable salt thereof are also useful for inhibiting the growth of a cancer cell or neoplastic cell. The compounds of Formula (I) or a pharmaceutically acceptable salt thereof are useful for treating or preventing a viral infection in a patient in need of such treatment or prevention. The compounds of Formula (I) or a pharmaceutically acceptable salt thereof are also useful for inhibiting the replication or infectivity of a virus. The compounds of Formula (I) or a pharmaceutically acceptable salt thereof are also useful for causing immunosuppression in a patient in need thereof. The compounds of Formula (I) or a pharmaceutically acceptable salt thereof are also useful for treating or preventing an autoimmune disease in a patient in need of such treatment or prevention.

The present invention provides compositions comprising a pharmaceutically acceptable carrier and an effective amount of a compound of Formula (I) or a pharmaceutically acceptable salt thereof. The compositions comprising a pharmaceutically acceptable carrier and a compound of Formula (I) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (I) or a pharmaceutically acceptable salt thereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (I) or a pharmaceutically acceptable salt thereof are also useful for causing immunosuppression in a patient in need thereof. The compositions comprising a pharmaceutically acceptable carrier and a compound of Formula (I) or a pharmaceutically acceptable salt thereof are also useful for treating or preventing an autoimmune disease in a patient in need of such treatment or prevention.

The invention further provides methods for treating or preventing cancer or neoplastic disease in a patient comprising administering to a patient in need of such treatment or prevention an effective amount of a compound of Formula (I) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (I) or a pharmaceutically acceptable salt thereof.

The invention further provides methods for treating or preventing a viral infection in a patient comprising administering to a patient in need of such treatment or prevention an effective amount of a compound of Formula (I) or a pharmaceutically acceptable salt thereof.

The invention further provides methods for inhibiting the replication or infectivity of a virus comprising contacting a virus or a virus-infected cell with an effective amount of a compound having the general Formula (I) or a pharmaceutically acceptable salt thereof.

The invention further provides methods for causing immunosuppression in a patient comprising administering to a patient in need thereof an effective amount of a compound of Formula (I) or a pharmaceutically acceptable salt thereof.

The invention further provides methods for treating or preventing an autoimmune disease in a patient comprising administering to a patient in need of such treatment or prevention an effective amount of a compound of Formula (I) or a pharmaceutically acceptable salt thereof.

Formula II

The present invention still further provides novel compounds having the general Formula (II):

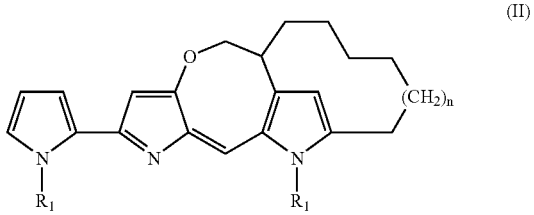

and pharmaceutically acceptable salts thereof, wherein:

each $R_1$ is independently selected from the group consisting of —H, —$CH_3$, —$CH_2C_6H_5$, —$C(O)OC(CH_3)_3$, and —$C(O)OCH_2C_6H_5$; and n is an integer ranging from 1 and 5.

The compounds of Formula (II) or a pharmaceutically acceptable salt thereof are useful for treating or preventing cancer or neoplastic disease in a patient in need of such treatment or prevention. The compounds of Formula (II) or a pharmaceutically acceptable salt thereof are also useful for inhibiting the growth of a cancer cell or neoplastic cell. The compounds of Formula (II) or a pharmaceutically acceptable salt thereof are useful for treating or preventing a viral infection in a patient in need of such treatment or prevention. The compounds of Formula (II) or a pharmaceutically acceptable salt thereof are also useful for inhibiting the replication or infectivity of a virus. The compounds of Formula (II) or a pharmaceutically acceptable salt thereof are also useful for causing immunosuppression in a patient in need thereof. The compounds of Formula (II) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (II) or a pharmaceutically acceptable salt thereof. The compositions comprising a pharmaceutically acceptable carrier and a compound of Formula (II) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (II) or a pharmaceutically acceptable salt thereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (II) or a pharmaceutically acceptable salt thereof are also useful for causing immunosuppression in a patient in need thereof. The compositions comprising a pharmaceutically acceptable carrier and a compound of Formula (II) or a pharmaceutically acceptable salt thereof are also useful for treating or preventing an autoimmune disease in a patient in need of such treatment or prevention.

The invention further provides methods for treating or preventing cancer or neoplastic disease in a patient comprising administering to a patient in need of such treatment or prevention an effective amount of a compound of Formula (II) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (II) or a pharmaceutically acceptable salt thereof.

The invention further provides methods for treating or preventing a viral infection in a patient comprising administering to a patient in need of such treatment or prevention an effective amount of a compound of Formula (II) or a pharmaceutically acceptable salt thereof.

The invention further provides methods for inhibiting the replication or infectivity of a virus comprising contacting a virus or a virus-infected cell with an effective amount of a compound having the general Formula (II) or a pharmaceutically acceptable salt thereof.

The invention further provides methods for causing immunosuppression in a patient comprising administering to a patient in need thereof an effective amount of a compound of Formula (II) or a pharmaceutically acceptable salt thereof.

The invention further provides methods for treating or preventing an autoimmune disease in a patient comprising administering to a patient in need of such treatment or prevention an effective amount of a compound of Formula (II) or a pharmaceutically acceptable salt thereof.

Formula III

The present invention still further provides novel compounds having the general Formula (III):

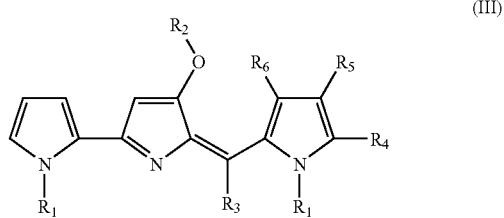

and pharmaceutically acceptable salts thereof, wherein:

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alkyl or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is —H, a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_5$ is —H, a $C_1$–$C_{12}$ straight chain alkyl, i-$C_3H_7$, or —$C_6H_5$;

$R_6$ is —H, a $C_1$–$C_{12}$ straight chain alkyl, i-$C_3H_7$, $C_3$–$C_7$ cycloalkyl, or —$C_6H_5$.

The compounds of Formula (III) or a pharmaceutically acceptable salt thereof are useful for treating or preventing cancer or neoplastic disease in a patient in need of such treatment or prevention. The compounds of Formula (III) or a pharmaceutically acceptable salt thereof are also useful for inhibiting the growth of a cancer cell or neoplastic cell. The compounds of Formula (III) or a pharmaceutically acceptable salt thereof are useful for treating or preventing a viral infection in a patient in need of such treatment or prevention. The compounds of Formula (III) or a pharmaceutically acceptable salt thereof are also useful for inhibiting the replication or infectivity of a virus. The compounds of Formula (III) or a pharmaceutically acceptable salt thereof are also useful for causing immunosuppression in a patient in need thereof. The compounds of Formula (III) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (III) or a pharmaceutically acceptable salt thereof. The compositions comprising a pharmaceutically acceptable carrier and a compound of Formula (III) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (III) or a pharmaceutically acceptable salt thereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (II) or a pharmaceutically acceptable salt thereof are also useful for causing immunosuppression in a patient in need thereof. The compositions comprising a pharmaceutically acceptable carrier and a compound of Formula (III) or a pharmaceutically acceptable salt thereof are also useful for treating or preventing an autoimmune disorder in a patient in need of such treatment or prevention.

The invention further provides methods for treating or preventing cancer or neoplastic disease in a patient comprising administering to a patient in need of such treatment or prevention an effective amount of a compound of Formula (III) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (III) or a pharmaceutically acceptable salt thereof.

The invention further provides methods for treating or preventing a viral infection in a patient comprising administering to a patient in need of such treatment or prevention an effective amount of a compound of Formula (III) or a pharmaceutically acceptable salt thereof.

The invention further provides methods for inhibiting the replication or infectivity of a virus comprising contacting a virus or a virus-infected cell with an effective amount of a compound having the general Formula (III) or a pharmaceutically acceptable salt thereof.

The invention further provides methods for causing immunosuppression in a patient comprising administering to a patient in need thereof an effective amount of a compound of Formula (III) or a pharmaceutically acceptable salt thereof.

The invention further provides methods for treating or preventing an autoimmune disease in a patient comprising administering to a patient in need of such treatment or prevention an effective amount of a compound of Formula (III) or a pharmaceutically acceptable salt thereof.

Formula IV

The present invention encompasses novel compounds having the general Formula (IV):

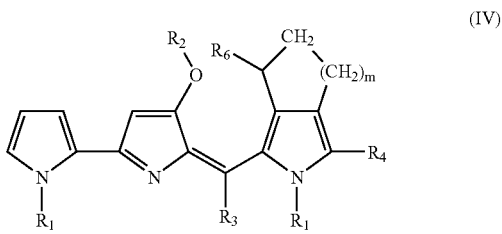

(IV)

and pharmaceutically acceptable salts thereof, wherein:

each $R_1$ is independently selected from the group consisting of —H, —$CH_3$, —$CH_2C_6H_5$, —C(O)OC$(CH_3)_3$, and —C(O)OCH$_2C_6H_5$;

$R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups, $R_8$ is —H, —$CH_3$, —$CH_2CH_3$, —$CH_2CH_2CH_3$, or —$(CH_2)_3CH_3$; and m is 1 to 4.

The compounds of Formula (IV) or a pharmaceutically acceptable salt thereof are useful for treating or preventing cancer or neoplastic disease in a patient in need of such treatment or prevention. The compounds of Formula (IV) or a pharmaceutically acceptable salt thereof are also useful for inhibiting the growth of a cancer cell or neoplastic cell. The compounds of Formula (IV) or a pharmaceutically acceptable salt thereof are useful for treating or preventing a viral infection in a patient in need of such treatment or prevention. The compounds of Formula (IV) or a pharmaceutically acceptable salt thereof are also useful for inhibiting the replication or infectivity of a virus. The compounds of Formula (IV) or a pharmaceutically acceptable salt thereof are also useful for inhibiting the replication or infectivity of a virus. The compounds of Formula (IV) or a pharmaceutically acceptable salt thereof are also useful for causing immunosuppression in a patient in need thereof. The compounds of Formula (IV) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (IV) or a pharmaceutically acceptable salt thereof. The compositions comprising a pharmaceutically acceptable carrier and a compound of Formula (IV) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (IV) or a pharmaceutically acceptable salt thereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (IV) or a pharmaceutically acceptable salt thereof are also useful for causing immunosuppression in a patient in need thereof. The compositions comprising a pharmaceutically acceptable carrier and a compound of Formula (IV) or a pharmaceutically acceptable salt thereof are also useful for treating or preventing an autoimmune disorder in a patient in need of such treatment or prevention.

The invention further provides methods for treating or preventing cancer or neoplastic disease in a patient comprising administering to a patient in need of such treatment or prevention an effective amount of a compound of Formula (IV) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (IV) or a pharmaceutically acceptable salt thereof.

The invention further provides methods for treating or preventing a viral infection in a patient comprising administering to a patient in need of such treatment or prevention an effective amount of a compound of Formula (IV) or a pharmaceutically acceptable salt thereof.

The invention further provides methods for inhibiting the replication or infectivity of a virus comprising contacting a virus or a virus-infected cell with an effective amount of a compound having the general Formula (IV) or a pharmaceutically acceptable salt thereof.

The invention further provides methods for causing immunosuppression in a patient comprising administering to a patient in need thereof an effective amount of a compound of Formula (IV) or a pharmaceutically acceptable salt thereof.

The invention further provides methods for treating or preventing an autoimmune disease in a patient comprising administering to a patient in need of such treatment or prevention an effective amount of a compound of Formula (IV) or a pharmaceutically acceptable salt thereof.

Formula V

The present invention encompasses novel compounds having the general Formula (V):

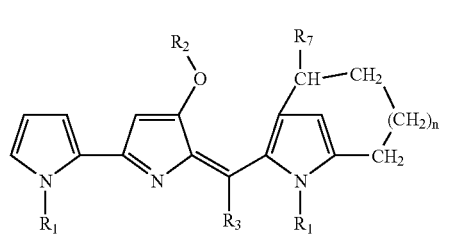

and pharmaceutically acceptable salts thereof, wherein:
each $R_1$ is independently selected from the group consisting of —H, —$CH_3$, —$CH_2C_6H_5$, —$C(O)OC(CH_3)_3$, and —$C(O)OCH_2C_6H_5$;
$R_2$ is a $C_1$–$C_{10}$ straight chain alkyl, or —$CH_2C_6H_5$, the —$CH_2C_6H_5$ being unsubstituted substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;
$R_7$ is —H, a $C_1$–$C_{10}$ straight chain alkyl, or —$CH(CH_3)_2$; and
n is 4 to 8.

The compounds of Formula (V) or a pharmaceutically acceptable salt thereof are useful for treating or preventing cancer or neoplastic disease in a patient in need of such treatment or prevention. The compounds of Formula (V) or a pharmaceutically acceptable salt thereof are also useful for inhibiting the growth of a cancer cell or neoplastic cell. The compounds of Formula (V) or a pharmaceutically acceptable salt thereof are useful for treating or preventing a viral infection in a patient in need of such treatment or prevention. The compounds of Formula (V) or a pharmaceutically acceptable salt thereof are also useful for inhibiting the replication or infectivity of a virus. The compounds of Formula (V) or a pharmaceutically acceptable salt thereof are also useful for causing immunosuppression in a patient in need thereof. The compounds of Formula (V) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (V) or a pharmaceutically acceptable salt thereof. The compositions comprising a pharmaceutically acceptable carrier and a compound of Formula (V) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (V) or a pharmaceutically acceptable salt thereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (V) or a pharmaceutically acceptable salt thereof are also useful for causing immunosuppression in a patient in need thereof. The compositions comprising a pharmaceutically acceptable carrier and a compound of Formula (V) or a pharmaceutically acceptable salt thereof are also useful for treating or preventing an autoimmune disorder in a patient in need of such treatment or prevention.

The invention further provides methods for treating or preventing cancer or neoplastic disease in a patient comprising administering to a patient in need of such treatment or prevention an effective amount of a compound of Formula (V) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (V) or a pharmaceutically acceptable salt thereof.

The invention further provides methods for treating or preventing a viral infection in a patient comprising administering to a patient in need of such treatment or prevention an effective amount of a compound of Formula (V) or a pharmaceutically acceptable salt thereof.

The invention further provides methods for inhibiting the replication or infectivity of a virus comprising contacting a virus or a virus-infected cell with an effective amount of a compound having the general Formula (V) or a pharmaceutically acceptable salt thereof.

The invention further provides methods for causing immunosuppression in a patient comprising administering to a patient in need thereof an effective amount of a compound of Formula (V) or a pharmaceutically acceptable salt thereof.

The invention further provides methods for treating or preventing an autoimmune disease in a patient comprising administering to a patient in need of such treatment or prevention an effective amount of a compound of Formula (V) or a pharmaceutically acceptable salt thereof.

Formula VI

The present invention encompasses novel compounds having the general Formula (VI):

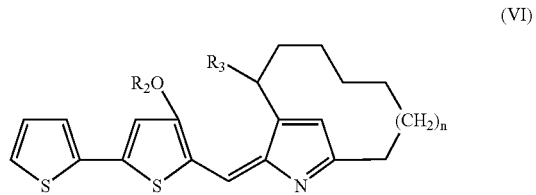

(VI)

and pharmaceutically acceptable salts thereof, wherein:
R$_2$ is a C$_1$–C$_{10}$ straight chain alkyl or —CH$_2$C$_6$H$_5$;
R$_3$ is a C$_1$–C$_{10}$ straight chain alkyl, —CH(CH$_3$)$_2$, —CH(CH$_3$)CH$_2$CH$_3$, —CH(CH$_3$)CH$_2$CH$_2$CH$_3$, —CH(OH)CH$_2$CH$_2$CH$_3$, —CH(Cl)CH$_2$CH$_2$CH$_3$, or —CH$_2$C$_6$H$_5$; and
n is 1 to 5.

The compounds of Formula (VI) or a pharmaceutically acceptable salt thereof are useful for treating or preventing cancer or neoplastic disease in a patient in need of such treatment or prevention. The compounds of Formula (VI) or a pharmaceutically acceptable salt thereof are also useful for inhibiting the growth of a cancer cell or neoplastic cell. The compounds of Formula (VI) or a pharmaceutically acceptable salt thereof are useful for treating or preventing a viral infection in a patient in need of such treatment or prevention. The compounds of Formula (VI) or a pharmaceutically acceptable salt thereof are also useful for inhibiting the replication or infectivity of a virus. The compounds of Formula (VI) or a pharmaceutically acceptable salt thereof are also useful for causing immunosuppression in a patient in need thereof. The compounds of Formula (VI) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (VI) or a pharmaceutically acceptable salt thereof. The compositions comprising a pharmaceutically acceptable carrier and a compound of Formula (VI) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (VI) or a pharmaceutically acceptable salt thereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (VI) or a pharmaceutically acceptable salt thereof are also useful for causing immunosuppression in a patient in need thereof. The compositions comprising a pharmaceutically acceptable carrier and a compound of Formula (VI) or a pharmaceutically acceptable salt thereof are also useful for treating or preventing an autoimmune disorder in a patient in need of such treatment or prevention.

The invention further provides methods for treating or preventing cancer or neoplastic disease in a patient comprising administering to a patient in need of such treatment or prevention an effective amount of a compound of Formula (VI) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (VI) or a pharmaceutically acceptable salt thereof.

The invention further provides methods for treating or preventing a viral infection in a patient comprising administering to a patient in need of such treatment or prevention an effective amount of a compound of Formula (VI) or a pharmaceutically acceptable salt thereof.

The invention further provides methods for inhibiting the replication or infectivity of a virus comprising a contacting virus or a virus-infected cell with an effective amount of a compound having the general Formula (VI) or a pharmaceutically acceptable salt thereof.

The invention further provides methods for causing immunosuppression in a patient comprising administering to a patient in need thereof an effective amount of a compound of Formula (VI) or a pharmaceutically acceptable salt thereof.

The invention further provides methods for treating or preventing an autoimmune disease in a patient comprising administering to a patient in need of such treatment or prevention an effective amount of a compound of Formula (VI) or a pharmaceutically acceptable salt thereof.

Formula VII

The present invention encompasses novel compounds having the general Formula (VII):

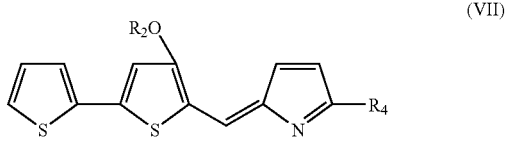

(VII)

and pharmaceutically acceptable salts thereof, wherein:
R$_2$ is a C$_1$–C$_{10}$ straight chain alkyl or —CH$_2$C$_6$H$_5$; and
R$_4$ is —H or a C$_1$–C$_{15}$ straight chain alkyl.

The compounds of Formula (VII) or a pharmaceutically acceptable salt thereof are useful for treating or preventing cancer or neoplastic disease in a patient in need of such treatment or prevention. The compounds of Formula (VII) or a pharmaceutically acceptable salt thereof are also useful for inhibiting the growth of a cancer cell or neoplastic cell. The compounds of Formula (VII) or a pharmaceutically acceptable salt thereof are useful for treating or preventing a viral infection in a patient in need of such treatment or prevention. The compounds of Formula (VII) or a pharmaceutically acceptable salt thereof are also useful for inhibiting the replication or infectivity of a virus. The compounds of Formula (VII) or a pharmaceutically acceptable salt thereof are also useful for causing immunosuppression in a patient in need thereof. The compounds of Formula (VII) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (VII) or a pharmaceutically acceptable salt thereof. The compositions comprising a pharmaceutically acceptable carrier and a compound of Formula (VII) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (VII) or a pharmaceutically acceptable salt thereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (VII) or a pharmaceutically acceptable salt thereof are also useful for causing immunosuppression in a patient in need thereof. The compositions comprising a pharmaceutically acceptable carrier and a compound of Formula (VII) or a pharmaceutically acceptable salt thereof are also useful for treating or preventing an autoimmune disorder in a patient in need of such treatment or prevention.

The invention further provides methods for treating or preventing cancer or neoplastic disease in a patient comprising administering to a patient in need of such treatment or prevention an effective amount of a compound of Formula (VII) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (VII) or a pharmaceutically acceptable salt thereof.

The invention further provides methods for treating or preventing a viral infection in a patient comprising administering to a patient in need of such treatment or prevention an effective amount of a compound of Formula (VII) or a pharmaceutically acceptable salt thereof.

The invention further provides methods for inhibiting the replication or infectivity of a virus comprising contacting a virus or a virus-infected cell with an effective amount of a compound having the general Formula (VII) or a pharmaceutically acceptable salt thereof.

The invention further provides methods for causing immunosuppression in a patient comprising administering to a patient in need thereof an effective amount of a compound of Formula (VII) or a pharmaceutically acceptable salt thereof.

The invention further provides methods for treating or preventing an autoimmune disease in a patient comprising administering to a patient in need of such treatment or prevention an effective amount of a compound of Formula (VII) or a pharmaceutically acceptable salt thereof.

Formula VIII

The present invention encompasses novel compounds having the general Formula (VIII):

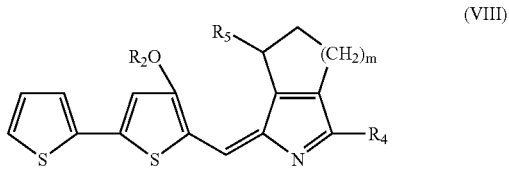

(VIII)

and pharmaceutically acceptable salts thereof, wherein:
$R_2$ is a $C_1$–$C_{10}$ straight chain alkyl or —$CH_2C_6H_5$;
$R_4$ is —H or a $C_1$–$C_{10}$ straight chain alkyl;
$R_5$ is —H or a $C_1$–$C_{10}$ straight chain alkyl;
and
m is 1 to 4.

The compounds of Formula (VIII) or a pharmaceutically acceptable salt thereof are useful for treating or preventing cancer or neoplastic disease in a patient in need of such treatment or prevention. The compounds of Formula (VIII) or a pharmaceutically acceptable salt thereof are also useful for inhibiting the growth of a cancer cell or neoplastic cell. The compounds of Formula (VIII) or a pharmaceutically acceptable salt thereof are useful for treating or preventing a viral infection in a patient in need of such treatment or prevention. The compounds of Formula (VIII) or a pharmaceutically acceptable salt thereof are also useful for inhibiting the replication or infectivity of a virus. The compounds of Formula (VII) or a pharmaceutically acceptable salt thereof are also useful for causing immunosuppression in a patient in need thereof. The compounds of Formula (VIII) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (VIII) or a pharmaceutically acceptable salt thereof. The compositions comprising a pharmaceutically acceptable carrier and a compound of Formula (VIII) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (VIII) or a pharmaceutically acceptable salt thereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (VIII) or a pharmaceutically acceptable salt thereof are also useful for causing immunosuppression in a patient in need thereof. The compositions comprising a pharmaceutically acceptable carrier and a compound of Formula (VIII) or a pharmaceutically acceptable salt thereof are also useful for treating or preventing an autoimmune disorder in a patient in need of such treatment or prevention.

The invention further provides methods for treating or preventing cancer or neoplastic disease in a patient comprising administering to a patient in need of such treatment or prevention an effective amount of a compound of Formula (VIII) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (VIII) or a pharmaceutically acceptable salt thereof.

The invention further provides methods for treating or preventing a viral infection in a patient comprising administering to a patient in need of such treatment or prevention an effective amount of a compound of Formula (VIII) or a pharmaceutically acceptable salt thereof.

The invention further provides methods for inhibiting the replication or infectivity of a virus comprising contacting a virus or a virus-infected cell with an effective amount of a compound having the general Formula (VIII) or a pharmaceutically acceptable salt thereof.

The invention further provides methods for causing immunosuppression in a patient comprising administering to a patient in need thereof an effective amount of a compound of Formula (VIII) or a pharmaceutically acceptable salt thereof.

The invention further provides methods for treating or preventing an autoimmune disease in a patient comprising administering to a patient in need of such treatment or prevention an effective amount of a compound of Formula (VIII) or a pharmaceutically acceptable salt thereof.

Formula IX

The present invention encompasses novel compounds having the general Formula (IX):

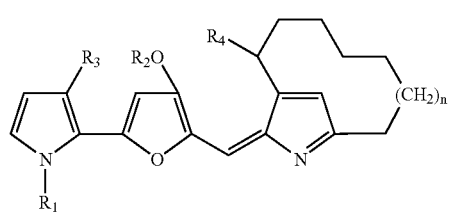

(IX)

and pharmaceutically acceptable salts thereof, wherein:

$R_1$ is —H, —$CH_3$, —$SO_2$-4-methylphenyl, —$CH_2C_6H_5$, —$Si(R_5R_6R_7)$, —$CH_2OCH_2CH_2SiCH_3$, —$C(O)OC(CH_3)_3$, or —$C(O)CH_2C_6H_5$;

$R_2$ is —$CH_3$, —$CH_2CH_3$, —$CH_2CH_2CH_3$, or —$CH_2C_6H_5$;

$R_3$ is —H or Cl;

$R_4$ is —H or a $C_1$–$C_{10}$ straight chain alkyl;

$R_5$ is a $C_1$–$C_4$ straight or branched chain alkyl or —$C_6H_5$;

$R_6$ is a $C_1$–$C_3$ straight or branched chain alkyl;

$R_7$ is a $C_1$–$C_3$ straight or branched chain alkyl; and n is 1 to 5.

The compounds of Formula (IX) or a pharmaceutically acceptable salt thereof are useful for treating or preventing cancer or neoplastic disease in a patient in need of such treatment or prevention. The compounds of Formula (IX) or a pharmaceutically acceptable salt thereof are also useful for inhibiting the growth of a cancer cell or neoplastic cell. The compounds of Formula (IX) or a pharmaceutically acceptable salt thereof are useful for treating or preventing a viral infection in a patient in need of such treatment or prevention. The compounds of Formula (IX) or a pharmaceutically acceptable salt thereof are also useful for inhibiting the replication or infectivity of a virus. The compounds of Formula (IX) or a pharmaceutically acceptable salt thereof are also useful for causing immunosuppression in a patient in need thereof. The compounds of Formula (IX) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (IX) or a pharmaceutically acceptable salt thereof. The compositions comprising a pharmaceutically acceptable carrier and a compound of Formula (IX) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (IX) or a pharmaceutically acceptable salt hereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (IX) or a pharmaceutically acceptable salt thereof are also useful for causing immunosuppression in a patient in need thereof. The compositions comprising a pharmaceutically acceptable carrier and a compound of Formula (IX) or a pharmaceutically acceptable salt thereof are also useful for treating or preventing an autoimmune disorder in a patient in need of such treatment or prevention.

The invention further provides methods for treating or preventing cancer or neoplastic disease in a patient comprising administering to a patient in need of such treatment or prevention an effective amount of a compound of Formula (IX) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (IX) or a pharmaceutically acceptable salt thereof.

The invention further provides methods for treating or preventing a viral infection in a patient comprising administering to a patient in need of such treatment or prevention an effective amount of a compound of Formula (IX) or a pharmaceutically acceptable salt thereof.

The invention further provides methods for inhibiting the replication or infectivity of a virus comprising contacting a virus or a virus-infected cell with an effective amount of a compound having the general Formula (IX) or a pharmaceutically acceptable salt thereof.

The invention further provides methods for causing immunosuppression in a patient comprising administering to a patient in need thereof an effective amount of a compound of Formula (IX) or a pharmaceutically acceptable salt thereof.

The invention further provides methods for treating or preventing an autoimmune disease in a patient comprising administering to a patient in need of such treatment or prevention an effective amount of a compound of Formula (IX) or a pharmaceutically acceptable salt thereof.

Formula X

The present invention encompasses novel compounds having the general Formula (X):

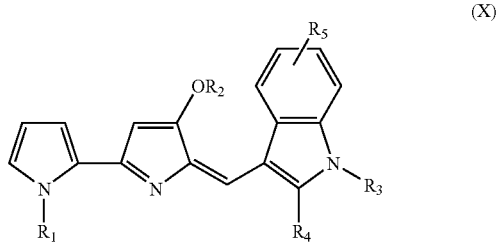

(X)

and pharmaceutically acceptable salts thereof, wherein:

$R_1$ is —H, —$CH_3$, —$CH_2C_6H_5$, —$COCH_3$, —$C(O)OC(CH_3)_3$, or —$C(O)CH_2C_6H_5$;

$R_2$ is a $C_1$–$C_{10}$ straight chain alkyl or —$CH_2C_6H_5$, the —$CH_2C_6H_5$ being unsubstituted or substituted with one or more halogen, methoxyl, methyl, methoxycarbonyl, or nitro groups;

$R_3$ is —H, —$CH_3$, —$CH_2C_6H_5$, or —$C(O)OC(CH_3)_3$;

$R_4$ is —H or —$CH_3$;

$R_5$ is —H, —$CH_3$, —$OCH_3$, —F, —Cl, —Br, —I, —CN, —$NH_2$, —$NH(C_1$–$C_3$ straight or branched chain alkyl), —$NHCOCH_3$, —$NO_2$, —COOH, —$COOR_6$, —OH, or —$OCH_2C_6H_5$; and $R_6$ is a $C_1$–$C_6$ straight chain alkyl.

The compounds of Formula (X) or a pharmaceutically acceptable salt thereof are useful for treating or preventing cancer or neoplastic disease in a patient in need of such treatment or prevention. The compounds of Formula (X) or a pharmaceutically acceptable salt thereof are also useful for inhibiting the growth of a cancer cell or neoplastic cell. The compounds of Formula (X) or a pharmaceutically acceptable salt thereof are useful for treating or preventing a viral infection in a patient in need of such treatment or prevention. The compounds of Formula (X) or a pharmaceutically acceptable salt thereof are also useful for inhibiting the replication or infectivity of a virus. The compounds of Formula (X) or a pharmaceutically acceptable salt thereof are also useful for causing immunosuppression in a patient in need thereof. The compounds of Formula (X) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (X) or a pharmaceutically acceptable salt thereof. The compositions comprising a pharmaceutically acceptable carrier and a compound of Formula (X) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (X) or a pharmaceutically acceptable salt thereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (X) or a pharmaceutically acceptable salt thereof are also useful for causing immunosuppression in a patient in need thereof. The compositions comprising a pharmaceutically acceptable carrier and a compound of Formula (X) or a pharmaceutically acceptable salt thereof are also useful for treating or preventing an autoimmune disorder in a patient in need of such treatment or prevention.

The invention further provides methods for treating or preventing cancer or neoplastic disease in a patient comprising administering to a patient in need of such treatment or prevention an effective amount of a compound of Formula (X) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (X) or a pharmaceutically acceptable salt thereof.

The invention further provides methods for treating or preventing a viral infection in a patient comprising administering to a patient in need of such treatment or prevention an effective amount of a compound of Formula (X) or a pharmaceutically acceptable salt thereof.

The invention further provides methods for inhibiting the replication or infectivity of a virus comprising contacting a virus or a virus-infected cell with an effective amount of a compound having the general Formula (X) or a pharmaceutically acceptable salt thereof.

The invention further provides methods for causing immunosuppression in a patient comprising administering to a patient in need thereof an effective amount of a compound of Formula (X) or a pharmaceutically acceptable salt thereof.

The invention further provides methods for treating or preventing an autoimmune disease in a patient comprising administering to a patient in need of such treatment or prevention an effective amount of a compound of Formula (XI) or a pharmaceutically acceptable salt thereof.

Formula XI

The present invention encompasses novel compounds having the general Formula (XI):

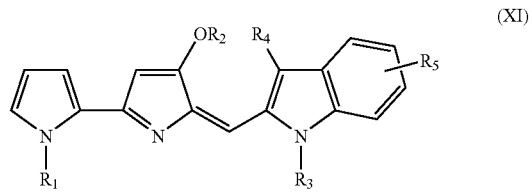

(XI)

and pharmaceutically acceptable salts thereof, wherein:

$R_1$ is —H, —$CH_3$, —$CH_2C_6H_5$, —$COCH_3$, —$C(O)OC(CH_3)_3$, or —$C(O)CH_2C_6H_5$;

$R_2$ is a $C_1$–$C_{10}$ straight chain alkyl or —$CH_2C_6H_5$;

$R_3$ is —H, —$CH_3$, —$CH_2C_6H_5$, —$C(O)OC(CH_3)_3$, or —$C(O)CH_2C_6H_5$;

$R_4$ is —H or —$CH_3$;

$R_5$ is —H, a $C_1$–$C_{10}$ straight chain alkyl, —$OR_6$, —F, —Cl, —Br, —I, —CN, —COOH, —$COOR_6$, —$NH_2$, —$NHCOR_6$, —$NO_2$, —OH, or —$OCH_2C_6H_5$; and $R_6$ is a $C_1$–$C_6$ straight chain alkyl.

The compounds of Formula (XI) or a pharmaceutically acceptable salt thereof are useful for treating or preventing cancer or neoplastic disease in a patient in need of such treatment or prevention. The compounds of Formula (XI) or a pharmaceutically acceptable salt thereof are also useful for inhibiting the growth of a cancer cell or neoplastic cell. The compounds of Formula (XI) or a pharmaceutically acceptable salt thereof are useful for treating or preventing a viral infection in a patient in need of such treatment or prevention. The compounds of Formula (XI) or a pharmaceutically acceptable salt thereof are also useful for inhibiting the replication or infectivity of a virus. The compounds of Formula (XI) or a pharmaceutically acceptable salt thereof are also useful for causing immunosuppression in a patient in need thereof. The compounds of Formula (XI) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (XI) or a pharmaceutically acceptable salt thereof. The compositions comprising a pharmaceutically acceptable carrier and a compound of Formula (XI) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (XI) or a pharmaceutically acceptable salt thereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (XI) or a pharmaceutically acceptable salt thereof are also useful for causing immunosuppression in a patient in need thereof. The compositions comprising a pharmaceutically acceptable carrier and compound of Formula (XI) or a pharmaceutically acceptable salt thereof are also useful for treating or preventing an autoimmune disorder in a patient in need of such treatment or prevention.

The invention further provides methods for treating or preventing cancer or neoplastic disease in a patient comprising administering to a patient in need of such treatment or prevention an effective amount of a compound of Formula (XI) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (XI) or a pharmaceutically acceptable salt thereof.

The invention further provides methods for treating or preventing a viral infection in a patient comprising administering to a patient in need of such treatment or prevention an effective amount of a compound of Formula (XI) or a pharmaceutically acceptable salt thereof.

The invention further provides methods for inhibiting the replication or infectivity of a virus comprising contacting a virus or a virus-infected cell with an effective amount of a compound having the general Formula (XI) or a pharmaceutically acceptable salt thereof.

The invention further provides methods for causing immunosuppression in a patient comprising administering to a patient in need thereof an effective amount of a compound of Formula (XI) or a pharmaceutically acceptable salt thereof.

The invention further provides methods for treating or preventing an autoimmune disease in a patient comprising administering to a patient in need of such treatment or prevention an effective amount of a compound of Formula (XI) or a pharmaceutically acceptable salt thereof.

Formula XII

The present invention encompasses novel compounds having the general Formula (XII):

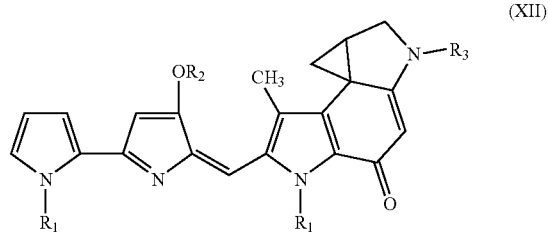

(XII)

and pharmaceutically acceptable salts thereof, wherein:
$R_1$ is —H, —$CH_3$, —$CH_2C_6H_5$, or —C(O)OC($CH_3$)$_3$;
$R_2$ is a $C_1$–$C_{10}$ straight chain alkyl or —$CH_2C_6H_5$;
$R_3$ is —H, —$SO_2CH_3$, —$SO_2C_6H_5$, —C(O)OC($CH_3$)$_3$, —$COCH_3$, —CO($CH_2$)$_4CH_3$, —CO($CH_2$)$_8CH_3$, —$COC_6H_5$, —CO-4-(NHCO$C_6H_5$)$C_6H_4$, —CO-2-pyridyl, —CO-2-napthyl, —CO-2-quinolyl, —CO-6-(NHCO($CH_2$)$_4$ $CH_3$)-2-quinolyl, —CO-2-pyrrolyl, —CO-2-indolyl, —CO-1-methyl-2-indolyl, —CO-2-benzofuranyl, —CO-2-benzothiophenyl, —CO-3-methyl-2-indenyl, or —CO—$R_4$-2-indolyl; and
$R_4$ is -5-OCH$_3$, -6-OH-7-OCH$_3$, -5-NHCONH$_2$, 5-NHCOC$_6$H$_5$, -5-NHCO-indolyl, -5-NHCO-2-benzofuranyl, -5-NHCO-5(NHCONH$_2$)-2-indolyl, or -5-NHCO-5-(NHCOC$_6$H$_5$)-2-indolyl.

The compounds of Formula (XII) or a pharmaceutically acceptable salt thereof are useful for treating or preventing cancer or neoplastic disease in a patient in need of such treatment or prevention. The compounds of Formula (XII) or a pharmaceutically acceptable salt thereof are also useful for inhibiting the growth of a cancer cell or neoplastic cell. The compounds of Formula (XII) or a pharmaceutically acceptable salt thereof are useful for treating or preventing a viral infection in a patient in need of such treatment or prevention. The compounds of Formula (XII) or a pharmaceutically acceptable salt thereof are also useful for inhibiting the replication or infectivity of a virus. The compounds of Formula (XII) or a pharmaceutically acceptable salt thereof are also useful for causing immunosuppression in a patient in need thereof. The compounds of Formula (XII) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (XII) or a pharmaceutically acceptable salt thereof. The compositions comprising a pharmaceutically acceptable carrier and a compound of Formula (XII) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (XII) or a pharmaceutically acceptable salt thereof are also useful for treating or preventing a viral infection in a patient in need of such treatment or prevention.

These compositions are also useful for inhibiting the replication or infectivity of a virus. The compositions comprising a pharmaceutically acceptable carrier and a compound of Formula (XII) or a pharmaceutically acceptable salt thereof are also useful for causing immunosuppression in a patient in need thereof. The compositions comprising a pharmaceutically acceptable carrier and a compound of Formula (XII) or a pharmaceutically acceptable salt thereof are also useful for treating or preventing an autoimmune disorder in a patient in need of such treatment or prevention.

The invention further provides methods for treating or preventing cancer or neoplastic disease in a patient comprising administering to a patient in need of such treatment or prevention an effective amount of a compound of Formula (XII) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (XII) or a pharmaceutically acceptable salt thereof.

The invention further provides methods for treating or preventing a viral infection in a patient comprising administering to a patient in need of such treatment or prevention an effective amount of a compound of Formula (XII) or a pharmaceutically acceptable salt thereof.

The invention further provides methods for inhibiting the replication or infectivity of a virus comprising contacting a virus or a virus-infected cell with an effective amount of a compound having the general Formula (XII) or a pharmaceutically acceptable salt thereof.

The invention further provides methods for causing immunosuppression in a patient comprising administering to a patient in need thereof an effective amount of a compound of Formula (XII) or a pharmaceutically acceptable salt thereof.

The invention further provides methods for treating or preventing an autoimmune disease in a patient comprising administering to a patient in need of such treatment or prevention an effective amount of a compound of Formula (XII) or a pharmaceutically acceptable salt thereof.

Formula XIII

The present invention encompasses novel compounds having the general Formula (XII):

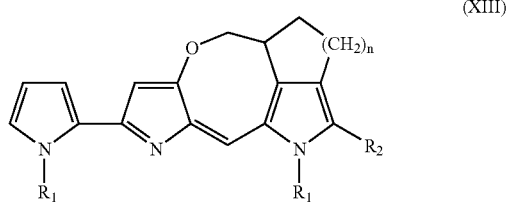

(XIII)

and pharmaceutically acceptable salts thereof, wherein:
each $R_1$ is independently selected from the group consisting of —H, —$CH_3$, —$CH_2C_6H_5$, —$C(O)OC(CH_3)_3$, or —$C(O)OCH_2C_6H_5$;
$R_2$ is —H or a $C_1$–$C_{10}$ straight chain alkyl; and
n is 1 to 4.

The compounds of Formula (XIII) or a pharmaceutically acceptable salt thereof are useful for treating or preventing cancer or neoplastic disease in a patient in need of such treatment or prevention. The compounds of Formula (XIII) or a pharmaceutically acceptable salt thereof are also useful for inhibiting the growth of a cancer cell or neoplastic cell. The compounds of Formula (XIII) or a pharmaceutically acceptable salt thereof are useful for treating or preventing a viral infection in a patient in need of such treatment or prevention. The compounds of Formula (XIII) or a pharmaceutically acceptable salt thereof are also useful for inhibiting the replication or infectivity of a virus. The compounds of Formula (XIII) or a pharmaceutically acceptable salt thereof are also useful for causing immunosuppression in a patient in need thereof. The compounds of Formula (XIII) or a pharmaceutically acceptable salt thereof are also useful for treating or preventing an autoimmune disorder in a patient in need of such treatment or prevention.

The present invention provides compositions comprising a pharmaceutically acceptable carrier and an effective amount of a compound of Formula (XIII) or a pharmaceutically acceptable salt thereof. The compositions comprising a pharmaceutically acceptable carrier and a compound of Formula (XIII) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (XIII) or a pharmaceutically acceptable salt thereof are also useful for treating or preventing a viral infection in a patient in need of such treatment or prevention. These compositions are also useful for inhibiting the replication or infectivity of a virus. The compositions comprising a pharmaceutically acceptable carrier and a compound of Formula (XIII) or a pharmaceutically acceptable sals thereof are also useful for causing immunosuppression in a patient in need thereof. The compositions comprising a pharmaceutically acceptable carrier and a compound of Formula (XIII) or a pharmaceutically acceptable salt thereof are also useful for treating or preventing an autoimmune disorder in a patient in need of such treatment or prevention.

The invention further provides methods for treating or preventing cancer or neoplastic disease in a patient comprising administering to a patient in need of such treatment or prevention an effective amount of a compound of Formula (XIII) or a pharmaceutically acceptable salt thereof.

The invention further provides methods for inhibiting the growth of a cancer cell or neoplastic cell comprising contacting a cancer cell or neoplastic cell with an effective amount of a compound having the general Formula (XIII) or a pharmaceutically acceptable salt thereof.

The invention further provides methods for treating or preventing a viral infection in a patient comprising administering to a patient in need of such treatment or prevention an effective amount of a composition comprising a compound of Formula (XIII) or a pharmaceutically acceptable salt thereof.

The invention further provides methods for inhibiting the replication or infectivity of a virus comprising contacting a virus or a virus-infected cell with an effective amount of a compound having the general Formula (XIII) or a pharmaceutically acceptable salt thereof.

The invention further provides methods for causing immunosuppression in a patient comprising administering to a patient in need thereof an effective amount of a compound of Formula (XIII) or a pharmaceutically acceptable salt thereof.

The invention further provides methods for treating or preventing an autoimmune disease in a patient comprising administering to a patient in need of such treatment or prevention an effective amount of a compound of Formula (XIII) or a pharmaceutically acceptable salt thereof.

The present invention may be understood more fully by reference to the following schemes, detailed description, and illustrative examples which are intended to exemplify non-limiting embodiments of the invention.

3.1. DEFINITIONS AND ABBREVIATIONS

Examples of halogens are fluorine, chlorine, bromine, and iodine.

Examples of $C_1$–$C_3$ straight or branched chain alkyl groups include, but are not limited to, methyl, ethyl, 1-propyl, and 2-propyl.

Examples of $C_1$–$C_4$ straight or branched chain alkyl groups include, but are not limited to, methyl, ethyl, 1-propyl, 2-propyl, 1-butyl, 2-butyl, 2-methyl-1-propyl, and 2-methyl-2-propyl.

Examples of $C_1$–$C_6$ straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, and 2-ethyl-1-butyl.

Examples of $C_1$–$C_5$ straight chain alkyl groups include, but are not limited to, methyl, ethyl, 1-propyl, 1-butyl, and 1-pentyl.

Examples of $C_1$–$C_6$ straight chain alkyl groups are methyl, ethyl, 1-propyl, 1-butyl, 1-pentyl, and 1-hexyl.

Examples of $C_1$–$C_{10}$ straight chain alkyl groups are methyl, ethyl, 1-propyl, 1-butyl, 1-pentyl, 1-hexyl, 1-heptyl, 1-octyl, 1-nonyl, and 1-decyl.

Examples of $C_1$–$C_{12}$ straight chain alkyl groups are methyl, ethyl, 1-propyl, 1-butyl, 1-pentyl, 1-hexyl, 1-heptyl, 1-octyl, 1-nonyl, 1-decyl, 1-undecyl, and 1-dodecyl.

Examples of $C_1$–$C_{15}$ straight chain alkyl groups are methyl, ethyl, 1-propyl, 1-butyl, 1-pentyl, 1-hexyl, 1-heptyl, 1-octyl, 1-nonyl, 1-decyl, 1-undecyl, 1-dodecyl, 1-tridecyl, 1-tetradecyl, and 1-pentadecyl.

Examples of $C_3$–$C_7$ cycloalkyl groups include but are not limited to cyclopropyl, cyclobutyl, cyclopentyl, cyclohexyl, and cycloheptyl.

The following abbreviations and their definitions, unless defined otherwise, are used in this specification:

| Abbreviation | Definition |
| --- | --- |
| BOC | —C(O)OC(CH$_3$)$_3$ |
| Cbz | —C(O)OCH$_2$C$_6$H$_5$ |
| THP | -2-tetrahydropyranyl |
| MOM | —OCH$_2$OCH$_3$ |
| TROC | —C(O)OCH$_2$C(Cl)$_3$ |
| Tf | —SO$_2$CF$_3$ |
| Ts | —SO$_2$-4-methyl-C$_6$H$_5$ |
| TBDMSCl | tert-butyldimethylsilyl chloride |
| DEAD | diethyl azodicarboxylate |
| SEM | 2-(trimethylsilyl)ethoxymethyl chloride |
| —CO-4-(NHCOC$_6$H$_5$)C$_6$H$_4$ | |
| —CO-2-pyridyl | |
| —CO-2-napthyl | |

-continued
| Abbreviation | Definition |
| --- | --- |
| —CO-2-quinolyl | 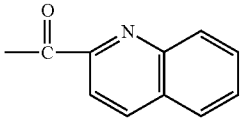 |
| —CO-6-(NHCO(CH$_2$)$_4$CH$_3$)-2-quinolyl | 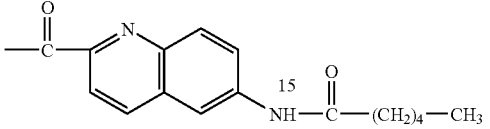 |
| —CO-2-pyrrolyl | 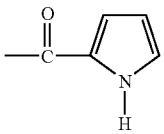 |
| —CO-2-indolyl | 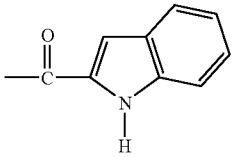 |
| —CO-1-methyl-2-indolyl | 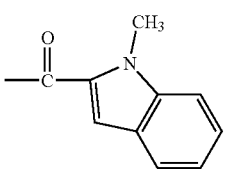 |
| —CO-2-benzofuranyl | 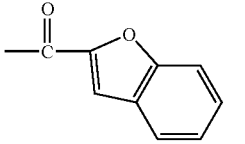 |
| —CO-2-benzothiophenyl | 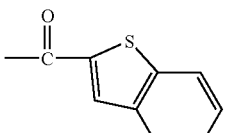 |
| —CO-3-methyl-2-indenyl | 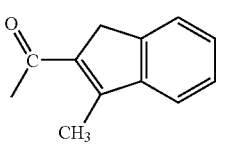 |
| —CO-(R$_4$-2-indolyl) | 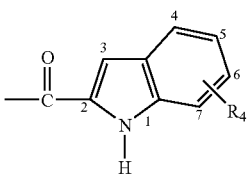 |
wherein R$_4$ can be 6 attached to the 3, 4, 5, 6, or 7 position of the indole ring.

When administered to a patient, e.g., a mammal for veterinary use or a human for clinical use, the Pyrrole-Type compounds are administered in isolated form. As used herein, "isolated" means that the Pyrrole-Type compounds are separated from other components of either (a) a natural source, such as a plant or cell, preferably bacterial culture, or (b) a synthetic organic chemical reaction mixture. Preferably, via conventional techniques, the Pyrrole-Type compounds are purified. As used herein, "purified" means that when isolated, the isolate contains at least 95%, preferably at least 98%, of a single Pyrrole-Type compound by weight of the isolate.

4. BRIEF DESCRIPTION OF THE DRAWINGS

FIG. 1 is a bar graph depicting cell survival following 72 hours of Compound 79 (4-methoxy-5-(1H-indol-2yl-methylene)-2,2'-bi-1H-pyrrole) treatment.

5. DETAILED DESCRIPTION OF THE INVENTION

5.1. Formula I

The present invention encompasses novel compounds having the general Formula (I) and pharmaceutically acceptable salts thereof, wherein:

each $R_1$ is independently selected from the group consisting of —H, —$CH_3$, —$CH_2C_6H_5$, —$C(O)OC(CH_3)_3$, and —$C(O)OCH_2C_6H_5$; and n is an integer ranging from 1 and 5.

The compounds of Formula (I) or a pharmaceutically acceptable salt thereof are useful for treating or preventing cancer or neoplastic disease in a patient in need of such treatment or prevention. The compounds of Formula (I) or a pharmaceutically acceptable salt thereof are also useful for inhibiting the growth of a cancer cell or neoplastic cell. The compounds of Formula (I) or a pharmaceutically acceptable salt thereof are useful for treating or preventing a viral infection in a patient in need of such treatment or prevention. The compounds of Formula (I) or a pharmaceutically acceptable salt thereof are also useful for inhibiting the replication or infectivity of a virus. The compounds of Formula (I) or a pharmaceutically acceptable salt thereof are also useful for causing immunosuppression in a patient in need thereof. The compounds of Formula (I) or a pharmaceutically acceptable salt thereof are also useful for treating an autoimmune disease in a patient in need of such treatment or prevention.

A preferred subclass of the compounds of Formula (I) is that wherein:

each $R_1$ is independently selected from the group consisting of —H and —$CH_3$; and n is an integer ranging from 1 to 5.

A more preferred subclass of the compounds of Formula (I) is that wherein:

$R_1$ is —H; and n is an integer ranging from 1 to 3.

The present invention also provides compositions comprising a pharmaceutically acceptable carrier and an effective amount of a compound of Formula (I) or a pharmaceutically acceptable salt thereof, wherein, in the compound of Formula (I):

each $R_1$ is independently selected from the group consisting of —H, —$CH_3$, —$CH_2C_6H_5$, —$C(O)OC(CH_3)_3$, and —$C(O)OCH_2C_6H_5$; and n is an integer ranging from 1 and 5.

The compositions comprising a pharmaceutically acceptable carrier and a compound of Formula (I) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (I) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (I) or a pharmaceutically acceptable salt thereof are also useful for causing immunosuppression in a patient in need thereof. The compositions comprising a pharmaceutically acceptable carrier and a compound of Formula (I) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (I) or a pharmaceutically acceptable salt thereof is that wherein, in the compound of Formula (I):

each $R_1$ is independently selected from the group consisting of —H and —$CH_3$; and n is an integer ranging from 1 to 5.

A more preferred subclass of the compositions comprising a pharmaceutically acceptable carrier and a compound of Formula (I) or a pharmaceutically acceptable salt thereof is that wherein, in the compound of Formula (I):

$R_1$ is —H; and n is an integer ranging from 1 to 3.

The invention further provides methods for treating or preventing cancer or neoplastic disease in a patient comprising administering to a patient in need of such treatment or prevention an effective amount of a compound of Formula (I) or a pharmaceutically acceptable salt thereof, wherein, in the compound of Formula (I):

each $R_1$ is independently selected from the group consisting of —H, —$CH_3$, —$CH_2C_6H_5$, —$C(O)OC(CH_3)_3$, and —$C(O)OCH_2C_6H_5$; and n is an integer ranging from 1 and 5.

For use in the methods for treating or preventing cancer or neoplastic disease, a preferred subclass of the compounds of Formula (I) is that wherein, in the compound of Formula (I):

each $R_1$ is independently selected from the group consisting of —H and —$CH_3$; and n is an integer ranging from 1 to 5.

For use in the methods for treating or preventing cancer or neoplastic disease, a more preferred subclass of the compounds of Formula (I) is that wherein, in the compound of Formula (I):

$R_1$ is —H; and n is an integer ranging from 1 to 3.

The invention further provides methods for inhibiting the growth of a cancer cell or neoplastic cell comprising contacting a cancer cell or neoplastic cell with an effective amount of a compound of general Formula (I) or a pharmaceutically acceptable salt thereof, wherein, in the compound of Formula (I):

each $R_1$ is independently selected from the group consisting of —H, —CH$_3$, —CH$_2$C$_6$H$_5$, —C(O)OC(CH$_3$)$_3$, and —C(O)OCH$_2$C$_6$H$_5$; and n is an integer ranging from 1 and 5.

For use in the methods for inhibiting the growth of a cancer or neoplastic cell, a preferred subclass of the compounds of Formula (I) is that wherein, in the compound of Formula (I):

each $R_1$ is independently selected from the group consisting of —H and —CH$_3$; and n is an integer ranging from 1 to 5.

For use in the methods for inhibiting the growth of a cancer or neoplastic cell, a more preferred subclass of the compounds of Formula (I) is that wherein, in the compound of Formula (I):

$R_1$ is —H; and n is an integer ranging from 1 to 3.

The invention further provides methods for treating or preventing a viral infection in a patient comprising administering to a patient in need of such treatment or prevention an effective amount of a compound of Formula (I) or a pharmaceutically acceptable salt thereof, wherein, in the compound of Formula (I):

each $R_1$ is independently selected from the group consisting of —H, —CH$_3$, —CH$_2$C$_6$H$_5$, —C(O)OC(CH$_3$)$_3$, and —C(O)OCH$_2$C$_6$H$_5$; and n is an integer ranging from 1 and 5.

For use in the present methods for treating or preventing a viral infection, a preferred subclass of the compounds of Formula (I) is that wherein, in the compound of Formula (I):

each $R_1$ is independently selected from the group consisting of —H and —CH$_3$; and n is an integer ranging from 1 to 5.

For use in the present methods for treating or preventing a viral infection, a more preferred subclass of the compounds of Formula (I) is that wherein, in the compound of Formula (I):

each $R_1$ is independently selected from the group consisting of —H and —CH$_3$; and n is an integer ranging from 1 to 5.

The invention further provides methods for inhibiting the replication or infectivity of a virus comprising contacting a virus or a virus-infected cell with an effective amount of a composition comprising a pharmaceutically acceptable carrier and a compound of general Formula (I) or a pharmaceutically acceptable salt thereof, wherein, in the compound of Formula (I):

each $R_1$ is independently selected from the group consisting of —H, —CH$_3$, —CH$_2$C$_6$H$_5$, —C(O)OC(CH$_3$)$_3$, and —C(O)OCH$_2$C$_6$H$_5$; and n is an integer ranging from 1 and 5.

For use in the methods for inhibiting the replication or infectivity of a virus, a preferred subclass of the compounds of Formula (I) are those wherein:

each $R_1$ is independently selected from the group consisting of —H and —CH$_3$; and n is an integer ranging from 1 to 5.

For use in the methods for inhibiting the replication or infectivity of a virus, a more preferred subclass of the compounds of Formula (I) are those wherein:

each $R_1$ is independently selected from the group consisting of —H and —CH$_3$; and n is an integer ranging from 1 to 5.

The invention further provides methods for causing immunosuppression in a patient comprising administering to a patient in need thereof an effective amount of a compound of Formula (I) or a pharmaceutically acceptable salt thereof, wherein, in the compound of Formula (I):

each $R_1$ is independently selected from the group consisting of —H, —CH$_3$, —CH$_2$C$_6$H$_5$, —C(O)OC(CH$_3$)$_3$, and —C(O)OCH$_2$C$_6$H$_5$; and n is an integer ranging from 1 and 5.

For use in the methods of causing immunosuppression, a preferred subclass of the compounds of Formula (I) are those wherein:

each $R_1$ is independently selected from the group consisting of —H and —CH$_3$; and n is an integer ranging from 1 to 5.

For use in the methods of causing immunosuppression, a more preferred subclass of the compounds of Formula (I) are those wherein:

each $R_1$ is independently selected from the group consisting of —H and —CH$_3$; and n is an integer ranging from 1 to 5.

The invention further provides methods for treating or preventing an autoimmune disease in a patient comprising administering to a patient in need of such treatment or prevention an effective amount of a compound of Formula (I) or a pharmaceutically acceptable salt thereof, wherein, in the compound of Formula (I):

each $R_1$ is independently selected from the group consisting of —H, —CH$_3$, —CH$_2$C$_6$H$_5$, —C(O)OC(CH$_3$)$_3$, and —C(O)OCH$_2$C$_6$H$_5$; and n is an integer ranging from 1 and 5.

For use in the methods of treating or preventing an autoimmune disease, a preferred subclass of the compounds of Formula (I) are those wherein:

each $R_1$ is independently selected from the group consisting of —H and —CH$_3$; and n is an integer ranging from 1 to 5.

For use in the methods of treating or preventing an autoimmune disease, a more preferred subclass of the compounds of Formula (I) are those wherein:

each $R_1$ is independently selected from the group consisting of —H and —CH$_3$; and n is an integer ranging from 1 to 5.

5.2. Formula II

The present invention encompasses novel compounds having the general Formula (II) and pharmaceutically acceptable salts thereof, wherein:

each $R_1$ is independently selected from the group consisting of —H, —CH$_3$, —CH$_2$C$_6$H$_5$, —C(O)OC(CH$_3$)$_3$, and —C(O)OCH$_2$C$_6$H$_5$; and n is an integer ranging from 1 and 5.

The compounds of Formula (II) or a pharmaceutically acceptable salt thereof are useful for treating or preventing cancer or neoplastic disease in a patient in need of such treatment or prevention. The compounds of Formula (II) or a pharmaceutically acceptable salt thereof are also useful for inhibiting the growth of a cancer cell or neoplastic cell. The compounds of Formula (II) or a pharmaceutically acceptable salt thereof are useful for treating or preventing a viral infection in a patient in need of such treatment or prevention. The compounds of Formula (II) or a pharmaceutically acceptable salt thereof are also useful for inhibiting the replication or infectivity of a virus. The compounds of Formula (II) or a pharmaceutically acceptable salt thereof are also useful for causing immunosuppression in a patient in need thereof. The compounds of Formula (II) or a pharmaceutically acceptable salt thereof are also useful for treating an autoimmune disease in a patient in need of such treatment or prevention.

A preferred subclass of the compounds of Formula (II) is that wherein:

each $R_1$ is independently selected from the group consisting of —H and —CH$_3$; and n is an integer ranging from 1 to 5.

A more preferred subclass of the compounds of Formula (II) is that wherein:

$R_1$ is —H; and n is an integer ranging from 1 to 3.

The present invention also provides compositions comprising a pharmaceutically acceptable carrier and an effective amount of a compound of Formula (II) or a pharmaceutically acceptable salt thereof, wherein, in the compound of Formula (II):

each $R_1$ is independently selected from the group consisting of —H, —CH$_3$, —CH$_2$C$_6$H$_5$, —C(O)OC(CH$_3$)$_3$, and —C(O)OCH$_2$C$_6$H$_5$; and n is an integer ranging from 1 and 5.

The compositions comprising a pharmaceutically acceptable carrier and a compound of Formula (II) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (II) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (II) or a pharmaceutically acceptable salt thereof are also useful for causing immunosuppression in a patient in need thereof. The compositions comprising a pharmaceutically acceptable carrier and a compound of Formula (II) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (II) or a pharmaceutically acceptable salt thereof is that wherein, in the compound of Formula (II):

each $R_1$ is independently selected from the group consisting of —H and —CH$_3$; and n is an integer ranging from 1 to 5.

A more preferred subclass of the compositions comprising a pharmaceutically acceptable carrier and a compound of Formula (II) or a pharmaceutically acceptable salt thereof is that wherein, in the compound of Formula (II):

$R_1$ is —H; and n is an integer ranging from 1 to 3.

The invention further provides methods for treating or preventing cancer or neoplastic disease in a patient comprising administering to a patient in need of such treatment or prevention an effective amount of a compound of Formula (II) or a pharmaceutically acceptable salt thereof, wherein, in the compound of Formula (II):

each $R_1$ is independently selected from the group consisting of —H, —CH$_3$, —CH$_2$C$_6$H$_5$, —C(O)OC(CH$_3$)$_3$, and —C(O)OCH$_2$C$_6$H$_5$; and n is an integer ranging from 1 and 5.

For use in the methods for treating or preventing cancer or neoplastic disease, a second preferred subclass of the compounds of Formula (II) is that wherein, in the compound of Formula (II):

each $R_1$ is independently selected from the group consisting of —H and —CH$_3$; and n is an integer ranging from 1 to 5.

For use in the methods for treating or preventing cancer or neoplastic disease, a more preferred subclass of the compounds of Formula (II) is that wherein, in the compound of Formula (II):

$R_1$ is —H; and n is an integer ranging from 1 to 3.

The invention further provides methods for inhibiting the growth of a cancer cell or neoplastic cell comprising contacting a cancer cell or neoplastic cell with an effective amount of a compound having the general Formula (II) or a pharmaceutically acceptable salt thereof, wherein, in the compound of Formula (II):

each $R_1$ is independently selected from the group consisting of —H, —CH$_3$, —CH$_2$C$_6$H$_5$, —C(O)OC(CH$_3$)$_3$, and —C(O)OCH$_2$C$_6$H$_5$; and n is an integer ranging from 1 and 5.

For use in the methods for inhibiting the growth of a cancer or neoplastic cell, a preferred subclass of the compounds of Formula (II) is that wherein, in the compound of Formula (II):

each $R_1$ is independently selected from the group consisting of —H and —CH$_3$; and n is an integer ranging from 1 to 5.

For use in the methods for inhibiting the growth of a cancer or neoplastic cell, a more preferred subclass of the compounds of Formula (II) is that wherein, in the compound of Formula (II):

$R_1$ is —H; and n is an integer ranging from 1 to 3.

The invention further provides methods for treating or preventing a viral infection in a patient comprising administering to a patient in need of such treatment or prevention an effective amount of a compound of Formula (II) or a pharmaceutically acceptable salt thereof, wherein, in the compound of Formula (II):

each $R_1$ is independently selected from the group consisting of —H, —CH$_3$, —CH$_2$C$_6$H$_5$, —C(O)OC(CH$_3$)$_3$, and —C(O)OCH$_2$C$_6$H$_5$;

and n is an integer ranging from 1 and 5.

For use in the present methods for treating or preventing a viral infection, a preferred subclass of the compounds of Formula (II) is that wherein, in the compound of Formula (II):

each $R_1$ is independently selected from the group consisting of —H and —CH$_3$; and n is an integer ranging from 1 to 5.

For use in the present methods for treating or preventing a viral infection, a more preferred subclass of the compounds of Formula (II) is that wherein, in the compound of Formula (II):

each $R_1$ is independently selected from the group consisting of —H and —CH$_3$; and n is an integer ranging from 1 to 5.

The invention further provides methods for inhibiting the replication or infectivity of a virus comprising contacting a virus or a virus-infected cell with an effective amount of a compound having the general Formula (II) or a pharmaceutically acceptable salt thereof, wherein, in the compound of Formula (II):

each $R_1$ is independently selected from the group consisting of —H, —$CH_3$, —$CH_2C_6H_5$, —$C(O)OC(CH_3)_3$, and —$C(O)OCH_2C_6H_5$; and n is an integer ranging from 1 and 5.

For use in the methods for inhibiting the replication or infectivity of a virus, a preferred subclass of the compounds of Formula (II) are those wherein:

each $R_1$ is independently selected from the group consisting of —H and —$CH_3$; and n is an integer ranging from 1 to 5.

For use in the methods for inhibiting the replication or infectivity of a virus, a more preferred subclass of the compounds of Formula (II) are those wherein:

each $R_1$ is independently selected from the group consisting of —H and —$CH_3$; and n is an integer ranging from 1 to 5.

The invention further provides methods for causing immunosuppression in a patient comprising administering to a patient in need thereof an effective amount of a compound of Formula (II) or a pharmaceutically acceptable salt thereof, wherein, in the compound of Formula (II):

each $R_1$ is independently selected from the group consisting of —H, —$CH_3$, —$CH_2C_6H_5$, —$C(O)OC(CH_3)_3$, and —$C(O)OCH_2C_6H_5$; and n is an integer ranging from 1 and 5.

For use in the methods for causing immunosuppression, a preferred subclass of the compounds of Formula (II) are those wherein:

each $R_1$ is independently selected from the group consisting of —H and —$CH_3$; and n is an integer ranging from 1 to 5.

For use in the methods for causing immunosuppression, a more preferred subclass of the compounds of Formula (II) are those wherein:

each $R_1$ is independently selected from the group consisting of —H and —$CH_3$; and n is an integer ranging from 1 to 5.

The invention further provides methods for treating or preventing an autoimmune disease in a patient comprising administering to a patient in need of such treatment or prevention an effective amount of a compound of Formula (II) or a pharmaceutically acceptable salt thereof, wherein, in the compound of Formula (II):

each $R_1$ is independently selected from the group consisting of —H, —$CH_3$, —$CH_2C_6H_5$, —$C(O)OC(CH_3)_3$, and —$C(O)OCH_2C_6H_5$; and n is an integer ranging from 1 and 5.

For use in the methods for treating or preventing an autoimmune disease, a preferred subclass of the compounds of Formula (II) are those wherein:

each $R_1$ is independently selected from the group consisting of —H and —$CH_3$; and n is an integer ranging from 1 to 5.

For use in the methods for treating or preventing an autoimmune disease, a more referred subclass of the compounds of Formula (II) are those wherein:

each $R_1$ is independently selected from the group consisting of —H and —$CH_3$; and n is an integer ranging from 1 to 5.

5.3. Formula III

The present invention encompasses novel compounds having the general Formula (III) and pharmaceutically acceptable salts thereof, wherein:

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alky or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is —H, a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_5$ is —H, a $C_1$–$C_{12}$ straight chain alkyl, i-$C_3H_7$, or —$C_6H_5$;

$R_6$ is —H, a $C_1$–$C_{12}$ straight chain alkyl, i-$C_3H_7$, $C_3$–$C_7$ cycloalkyl, or —$C_6H_5$.

The compounds of Formula (III) or a pharmaceutically acceptable salt thereof are useful for treating or preventing cancer or neoplastic disease in a patient in need of such treatment or prevention. The compounds of Formula (III) or a pharmaceutically acceptable salt thereof are also useful for inhibiting the growth of a cancer cell or neoplastic cell. The compounds of Formula (III) or a pharmaceutically acceptable salt thereof are useful for treating or preventing a viral infection in a patient in need of such treatment or prevention. The compounds of Formula (III) or a pharmaceutically acceptable salt thereof are also useful for inhibiting the replication or infectivity of a virus. The compounds of Formula (III) or a pharmaceutically acceptable salt thereof are also useful for causing immunosuppression in a patient in need thereof. The compounds of Formula (III) or a pharmaceutically acceptable salt thereof are also useful for treating an autoimmune disease in a patient in need of such treatment or prevention.

A preferred subclass of the compounds of Formula (III) is that wherein:

$R_1$ is —H;
$R_2$ is —$CH_3$, —$CH_2C_6H_5$;
$R_3$ is —$CH_3$;
$R_4$ is —H or a $C_1$–$C_{15}$ straight chain alkyl;
$R_5$ is —H or a $C_1$–$C_5$ straight chain alkyl; and
$R_6$ is —H or —$CH_3$;

A more preferred subclass of the compounds of Formula (III) is that wherein:

$R_1$ is —H;
$R_2$ and $R_3$ is —$CH_3$;
$R_4$ is —H or —$(CH_2)_{14}CH_3$;
$R_5$ is —H or -n-$C_5H_{11}$; and
$R_6$ is —H.

The present invention also provides compositions comprising a pharmaceutically acceptable carrier and an effective amount of a compound of Formula (III) or a pharmaceutically acceptable salt thereof, wherein, in the compound of Formula (III):

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alky or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is —H, a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_5$ is —H, a $C_1$–$C_{12}$ straight chain alkyl, i-$C_3H_7$, or —$C_6H_5$;

$R_6$ is —H, a $C_1$–$C_{12}$ straight chain alkyl, i-$C_3H_7$, $C_3$–$C_7$ cycloalkyl, or —$C_6H_5$.

The compositions comprising a pharmaceutically acceptable carrier and a compound of Formula (III) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (III) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (III) or a pharmaceutically acceptable salt thereof are also useful for causing immunosuppression in a patient in need thereof. The compositions comprising a pharmaceutically acceptable carrier and a compound of Formula (III) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (III) or a pharmaceutically acceptable salt thereof is that wherein, in the compound of Formula (III):

$R_1$ is —H;

$R_2$ is —$CH_3$, —$CH_2C_6H_5$;

$R_3$ is —$CH_3$;

$R_4$ is —H or a $C_1$–$C_{15}$ straight chain alkyl;

$R_5$ is —H or a $C_1$–$C_5$ straight chain alkyl; and $R_6$ is —H or —$CH_3$.

A more preferred subclass of the compositions comprising a pharmaceutically acceptable carrier and a compound of Formula (III) or a pharmaceutically acceptable salt thereof is that wherein, in the compound of Formula (III):

$R_1$ is —H;

$R_2$ and $R_3$ is —$CH_3$;

$R_4$ is —H or —$(CH_2)_{14}CH_3$;

$R_5$ is -n-$C_5H_{11}$; and $R_6$ is —H.

The invention further provides methods for treating or preventing cancer or neoplastic disease in a patient comprising administering to a patient in need of such treatment or prevention an effective amount of a compound of Formula (III) or a pharmaceutically acceptable salt thereof, wherein, in the compound of Formula (III):

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alky or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_5$ is —H, a $C_1$–$C_{12}$ straight chain alkyl, i-$C_3H_7$, or —$C_6H_5$;

$R_6$ is —H, a $C_1$–$C_{12}$ straight chain alkyl, i-$C_3H_7$, $C_3$–$C_7$ cycloalkyl, or —$C_6H_5$.

For use in the methods for treating or preventing cancer or neoplastic disease, a preferred subclass of the compounds of Formula (III) is that wherein, in the compound of Formula (III):

$R_1$ is —H;

$R_2$ is —$CH_3$, —$CH_2C_6H_5$;

$R_3$ is —$CH_3$;

$R_4$ is —H or a $C_1$–$C_{15}$ straight chain alkyl;

$R_5$ is —H or a $C_1$–$C_5$ straight chain alkyl; and $R_6$ is —H or —$CH_3$.

For use in the methods for treating or preventing cancer or neoplastic disease, a more preferred subclass of the compounds of Formula (III) is that wherein, in the compound of Formula (III):

$R_1$ is —H;

$R_2$ and $R_3$ is —$CH_3$;

$R_4$ is —H or —$(CH_2)_{14}CH_3$;

$R_5$ is —H or -n-$C_5H_{11}$; and $R_6$ is —H.

The invention further provides methods for inhibiting the growth of a cancer cell or neoplastic cell comprising contacting a cancer cell or neoplastic cell with an effective amount of a compound having the general Formula (III) or a pharmaceutically acceptable salt thereof, wherein, in the compound of Formula (III):

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alky or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_5$ is —H, a $C_1$–$C_{12}$ straight chain alkyl, i-$C_3H_7$, or —$C_6H_5$;

$R_6$ is —H, a $C_1$–$C_{12}$ straight chain alkyl, i-$C_3H_7$, $C_3$–$C_7$ cycloalkyl, or —$C_6H_5$.

For use in the methods for inhibiting the growth of a cancer or neoplastic cell, a preferred subclass of the compounds of Formula (III) is that wherein, in the compound of Formula (III):

$R_1$ is —H;

$R_2$ is —$CH_3$, —$CH_2C_6H_5$;

$R_3$ is —$CH_3$;

$R_4$ is —H or a $C_1$–$C_{15}$ straight chain alkyl;

$R_5$ is —H or a $C_1$–$C_5$ straight chain alkyl; and $R_6$ is —H or —$CH_3$.

For use in the methods for inhibiting the growth of a cancer or neoplastic cell, a more preferred subclass of the compounds of Formula (III) is that wherein, in the compound of Formula (III):

$R_1$ is —H;

$R_2$ and $R_3$ is —$CH_3$;

$R_4$ is —H or —$(CH_2)_{14}CH_3$;

$R_5$ is —H or -n-$C_5H_{11}$; and
$R_6$ is —H.

The invention further provides methods for treating or preventing a viral infection in a patient comprising administering to a patient in need of such treatment or prevention an effective amount of a compound of Formula (III) or a pharmaceutically acceptable salt thereof, wherein, in the compound of Formula (III):

each $R_1$ is independently selected from the group consisting of —H, —$CH_3$, —$CH_2C_6H_5$, —$C(O)OC(CH_3)_3$, and —$C(O)OCH_2C_6H_5$; p $R_2$ is a $C_1$–$C_{10}$ straight chain alky or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_5$ is —H, a $C_1$–$C_{12}$ straight chain alkyl, i-$C_3H_7$, or —$C_6H_5$;

$R_6$ is —H, a $C_1$–$C_{12}$ straight chain alkyl, i-$C_3H_7$, $C_3$–$C_7$ cycloalkyl, or —$C_6H_5$.

For use in the present methods for treating or preventing a viral infection, a preferred subclass of the compounds of Formula (III) is that wherein, in the compound of Formula (III):

$R_1$ is —H;
$R_2$ is —$CH_3$, —$CH_2C_6H_5$;
$R_3$ is —$CH_3$;
$R_4$ is —H or a $C_1$–$C_{15}$ straight chain alkyl;
$R_5$ is —H or a $C_1$–$C_{15}$ straight chain alkyl; and
$R_6$ is —H or —$CH_3$.

For use in the present methods for treating or preventing a viral infection, a more preferred subclass of the compounds of Formula (III) is that wherein, in the compound of Formula (III):

$R_1$ is —H;
$R_2$ and $R_3$ is —$CH_3$;
$R_4$ is —H or —$(CH_2)_{14}CH_3$;
$R_5$ is —H or -n-$C_5H_{11}$; and
$R_6$ is —H.

The invention further provides methods for inhibiting the replication or infectivity of a virus comprising contacting a virus or a virus-infected cell with an effective amount of a compound having the general Formula (III) or a pharmaceutically acceptable salt thereof, wherein, in the compound of Formula (III):

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alky or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_5$ is —H, a $C_1$–$C_{12}$ straight chain alkyl, i-$C_3H_7$, or —$C_6H_5$;

$R_6$ is —H, a $C_1$–$C_{12}$ straight chain alkyl, i-$C_3H_7$, $C_3$–$C_7$ cycloalkyl, or —$C_6H_5$.

For use in the methods for inhibiting the replication or infectivity of a virus, a preferred subclass of the compounds of Formula (III) are those wherein:

$R_1$ is —H;
$R_2$ is —$CH_3$, —$CH_2C_6H_5$;
$R_3$ is —$CH_3$;
$R_4$ is —H or a $C_1$–$C_{15}$ straight chain alkyl;
$R_5$ is —H or a $C_1$–$C_{15}$ straight chain alkyl; and
$R_6$ is —H or —$CH_3$.

For use in the methods for inhibiting the replication or infectivity of a virus, a more preferred subclass of the compounds of Formula (III) are those wherein:

$R_1$ is —H;
$R_2$ and $R_3$ is —$CH_3$;
$R_4$ is —H or —$(CH_2)_{14}CH_3$;
$R_5$ is —H or -n-$C_5H_{11}$; and
$R_6$ is —H.

The invention further provides methods for causing immunosuppression in a patient comprising administering to a patient in need thereof an effective amount of a compound of Formula (III) or a pharmaceutically acceptable salt thereof, wherein, in the compound of Formula (III):

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alky or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_5$ is —H, a $C_1$–$C_{12}$ straight chain alkyl, i-$C_3H_7$, or —$C_6H_5$;

$R_6$ is —H, a $C_1$–$C_{12}$ straight chain alkyl, i-$C_3H_7$, $C_3$–$C_7$ cycloalkyl, or —$C_6H_5$.

For use in the methods for causing immunosuppression, a preferred subclass of the compounds of Formula (III) are those wherein:

$R_1$ is —H;
$R_2$ is —$CH_3$, —$CH_2C_6H_5$;
$R_3$ is —$CH_3$;
$R_4$ is —H or a $C_1$–$C_{15}$ straight chain alkyl;
$R_5$ is —H or a $C_1$–$C_5$ straight chain alkyl; and
$R_6$ is —H or —$CH_3$.

For use in the methods for causing immunosuppression, a more preferred subclass of the compounds of Formula (III) are those wherein:

$R_1$ is —H;
$R_2$ and $R_3$ is —$CH_3$;
$R_4$ is —H or —$(CH_2)_{14}CH_3$;
$R_5$ is —H or -n-$C_5H_{11}$; and
$R_6$ is —H.

The invention further provides methods for treating or preventing an autoimmune disease in a patient comprising administering to a patient in need of such treatment or prevention an effective amount of a compound of Formula (III) or a pharmaceutically acceptable salt thereof, wherein, in the compound of Formula (III):

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alky or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_5$ is —H, a $C_1$–$C_{12}$ straight chain alkyl, i-$C_3H_7$, or —$C_6H_5$;

$R_6$ is —H, a $C_1$–$C_{12}$ straight chain alkyl, i-$C_3H_7$, $C_3$–$C_7$ cycloalkyl, or —$C_6H_5$.

For use in the methods for treating or preventing an autoimmune disease, a preferred subclass of the compounds of Formula (III) are those wherein:

$R_1$ is —H;
$R_2$ is —$CH_3$, —$CH_2C_6H_5$;
$R_3$ is —$CH_3$;
$R_4$ is —H or a $C_1$–$C_{15}$ straight chain alkyl;
$R_5$ is —H or a $C_1$–$C_5$ straight chain alkyl; and
$R_6$ is —H or —$CH_3$.

For use in the methods for treating or preventing an autoimmune disease, a more preferred subclass of the compounds of Formula (III) are those wherein:

$R_1$ is —H;
$R_2$ and $R_3$ is —$CH_3$,
$R_4$ is —H or —$(CH_2)_{14}CH_3$;
$R_5$ is —H or -n-$C_5H_{11}$; and
$R_6$ is —H.

5.4. Formula IV

The present invention encompasses novel compounds having the general Formula (IV) and pharmaceutically acceptable salts thereof, wherein:

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_8$ is —H, —$CH_3$, —$CH_2CH_3$, —$CH_2CH_2CH_3$, or —$(CH_2)_3CH_3$; and m is 1 to 4.

The compounds of Formula (IV) or a pharmaceutically acceptable salt thereof are useful for treating or preventing cancer or neoplastic disease in a patient in need of such treatment or prevention. The compounds of Formula (IV) or a pharmaceutically acceptable salt thereof are also useful for inhibiting the growth of a cancer cell or neoplastic cell. The compounds of Formula (IV) or a pharmaceutically acceptable salt thereof are useful for treating or preventing a viral infection in a patient in need of such treatment or prevention. The compounds of Formula (IV) or a pharmaceutically acceptable salt thereof are also useful for inhibiting the replication or infectivity of a virus. The compounds of Formula (IV) or a pharmaceutically acceptable salt thereof are also useful for causing immunosuppression in a patient in need thereof. The compounds of Formula (IV) or a pharmaceutically acceptable salt thereof are also useful for treating an autoimmune disease in a patient in need of such treatment or prevention.

A preferred subclass of the compounds of Formula (IV) is that wherein:

$R_1$ is —H;
$R_2$ is —$CH_3$ or —$CH_2C_6H_5$;
$R_3$ is —$CH_3$;
$R_4$ is —H or a $C_1$–$C_{15}$ straight chain alkyl;
$R_8$ is —H or —$CH_3$; and
m is 2.

A more preferred subclass of the compounds of Formula (IV) is that wherein:

$R_1$ is —H;
$R_2$, $R_3$, and $R_4$ is —$CH_3$;
$R_8$ is —H or $CH_3$; and
m is 2.

The present invention also provides compositions comprising a pharmaceutically acceptable carrier and an effective amount of a compound of Formula (IV) or a pharmaceutically acceptable salt thereof, wherein, in the compound of Formula (IV):

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_8$ is —H, —$CH_3$, —$CH_2CH_3$, —$CH_2CH_2CH_3$, or —$(CH_2)_3CH_3$; and m is 1 to 4.

The compositions comprising a pharmaceutically acceptable carrier and a compound of Formula (IV) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (IV) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (IV) or a pharmaceutically acceptable salt thereof are also useful for causing immunosuppression in a patient in need thereof. The compositions comprising a pharmaceutically acceptable carrier and a compound of Formula (IV) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (IV) or a pharmaceutically acceptable salt thereof is that wherein, in the compound of Formula (IV):

$R_1$ is —H;
$R_2$ is —$CH_3$ or —$CH_2C_6H_5$;
$R_3$ is —$CH_3$;
$R_4$ is —H or a $C_1$–$C_{15}$ straight chain alkyl;
$R_8$ is —H or —$CH_3$; and
m is 2.

A more preferred subclass of the compositions comprising a pharmaceutically acceptable carrier and a compound of Formula (IV) or a pharmaceutically acceptable salt thereof is that wherein, in the compound of Formula (IV):
$R_1$ is —H;
$R_2$, $R_3$, and $R_4$ is —$CH_3$;
$R_8$ is —H or $CH_3$; and
m is 2.

The invention further provides methods for treating or preventing cancer or neoplastic disease in a patient comprising administering to a patient in need of such treatment or prevention an effective amount of a compound of Formula (IV) or a pharmaceutically acceptable salt thereof, wherein, in the compound of Formula (IV):
each $R_1$ is independently selected from the group consisting of —H, —$CH_3$, —$CH_2C_6H_5$, —$C(O)OC(CH_3)_3$, and —$C(O)OCH_2C_6H_5$;
$R_2$ is a $C_1$–$C_{10}$ straight chain alkyl, or —$CH_2C_6H_5$ the —$CH_2C_6H_5$ being unsubstituted or substituted on the phenyl with one or more methoxyl, halogen, methyl, nitro, trifluoromethyl, or methoxylcarbonyl groups;
$R_3$ is —$CH_3$, —$CH_2CH_3$, or —$C_6H_5$;
$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;
$R_8$ is —H, —$CH_3$, —$CH_2CH_3$, —$CH_2CH_2CH_3$, or —$(CH_2)_3CH_3$; and
m is 1 to 4.

For use in the methods for treating or preventing cancer or neoplastic disease, a preferred subclass of the compounds of Formula (IV) is that wherein, in the compound of Formula (IV):
$R_1$ is —H;
$R_2$ is —$CH_3$ or —$CH_2C_6H_5$;
$R_3$ is —$CH_3$;
$R_4$ is —H or a $C_1$–$C_{15}$ straight chain alkyl;
$R_8$ is —H or —$CH_3$; and
m is 2.

For use in the methods for treating or preventing cancer or neoplastic disease, a more preferred subclass of the compounds of Formula (IV) is that wherein, in the compound of Formula (IV):
$R_1$ is —H;
$R_2$, $R_3$, and $R_4$ is —$CH_3$;
$R_8$ is —H or $CH_3$; and
m is 2.

The invention further provides methods for inhibiting the growth of a cancer cell or neoplastic cell comprising contacting a cancer cell or neoplastic cell with an effective amount of a compound having the general Formula (IV) or a pharmaceutically acceptable salt thereof, wherein, in the compound of Formula (IV):
each $R_1$ is independently selected from the group consisting of —H, —$CH_3$, —$CH_2C_6H_5$, —$C(O)OC(CH_3)_3$, and —$C(O)OCH_2C_6H_5$;
$R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;
$R_3$ is —$CH_3$, —$CH_2CH_3$, or —$C_6H_5$;
$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups,
$R_8$ is —H, —$CH_3$, —$CH_2CH_3$, —$CH_2CH_2CH_3$, or —$(CH_2)_3CH_3$; and
m is 1 to 4.

For use in the methods for inhibiting the growth of a cancer or neoplastic cell, a preferred subclass of the compounds of Formula (IV) is that wherein, in the compound of Formula (IV):
$R_1$ is —H;
$R_2$ is —$CH_3$ or —$CH_2C_6H_5$;
$R_3$ is —$CH_3$;
$R_4$ is —H or a $C_1$–$C_{15}$ straight chain alkyl;
$R_8$ is —H or —$CH_3$; and
m is 2.

For use in the methods for inhibiting the growth of a cancer or neoplastic cell, a more preferred subclass of the compounds of Formula (IV) is that wherein, in the compound of Formula (IV):
$R_1$ is —H;
$R_2$, $R_3$, and $R_4$ is —$CH_3$;
$R_8$ is —H or $CH_3$; and
m is 2.

The invention further provides methods for treating or preventing a viral infection in a patient comprising administering to a patient in need of such treatment or prevention an effective amount of a compound of Formula (IV) or a pharmaceutically acceptable salt thereof, wherein, in the compound of Formula (IV):
each $R_1$ is independently selected from the group consisting of —H, —$CH_3$, —$CH_2C_6H_5$, —$C(O)OC(CH_3)_3$, and —$C(O)OCH_2C_6H_5$;
$R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;
$R_3$ is —$CH_3$, —$CH_2CH_3$, or —$C_6H_5$;
$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;
$R_8$ is —H, —$CH_3$, —$CH_2CH_3$, —$CH_2CH_2CH_3$, or —$(CH_2)_3CH_3$; and
m is 1 to 4.

For use in the present methods for treating or preventing a viral infection, a preferred subclass of the compounds of Formula (IV) is that wherein, in the compound of Formula (IV):
$R_1$ is —H;
$R_2$ is —$CH_3$ or —$CH_2C_6H_5$;
$R_3$ is —$CH_3$;
$R_4$ is —H or a $C_1$–$C_{15}$ straight chain alkyl;
$R_5$ is —H or —$CH_3$; and
m is 2.

For use in the present methods for treating or preventing a viral infection, a more preferred subclass of the compounds of Formula (IV) is that wherein, in the compound of Formula (IV):
$R_1$ is —H;
$R_2$, $R_3$, and $R_4$ is —$CH_3$;
$R_8$ is —H or $CH_3$; and
m is 2.

The invention further provides methods for inhibiting the replication or infectivity of a virus comprising contacting a virus or a virus-infected cell with an effective amount of a compound having the general Formula (IV) or a pharmaceutically acceptable salt thereof, wherein, in the compound of Formula (IV):
each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_8$ is —H, —$CH_3$, —$CH_2CH_3$, —$CH_2CH_2CH_3$, or —$(CH_2)_3CH_3$; and m is 1 to 4.

For use in the methods for inhibiting the replication or infectivity of a virus, a preferred subclass of the compounds of Formula (IV) are those wherein:

$R_1$ is —H;
$R_2$ is —$CH_3$ or —$CH_2C_6H_5$;
$R_3$ is —$CH_3$;
$R_4$ is —H or a $C_1$–$C_{15}$ straight chain alkyl;
$R_8$ is —H or —$CH_3$; and
m is 2.

For use in the methods for inhibiting the replication or infectivity of a virus, a more preferred subclass of the compounds of Formula (IV) are those wherein:

$R_1$ is —H;
$R_2$, $R_3$, and $R_4$ is —$CH_3$;
$R_8$ is —H or $CH_3$; and
m is 2.

The invention further provides methods for causing immunosuppression in a patient comprising administering to a patient in need thereof an effective amount of a compound of Formula (IV) or a pharmaceutically acceptable salt thereof, wherein, in the compound of Formula (IV):

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_8$ is —H, —$CH_3$, —$CH_2CH_3$, —$CH_2CH_2CH_3$, or —$(CH_2)_3CH_3$; and m is 1 to 4.

For use in the methods for causing immunosuppression, a preferred subclass of the compounds of Formula (IV) are those wherein:

$R_1$ is —H;
$R_2$ is —$CH_3$ or —$CH_2C_6H_5$;
$R_3$ is —$CH_3$;
$R_4$ is —H or a $C_1$–$C_{15}$ straight chain alkyl;
$R_8$ is —H or —$CH_3$; and
m is 2.

For use in the methods for causing immunosuppression, a more preferred subclass of the compounds of Formula (IV) are those wherein:

$R_1$ is —H;
$R_2$, $R_3$, and $R_4$ is —$CH_3$;
$R_8$ is —H or —$CH_3$; and
m is 2.

The invention further provides methods for treating or preventing an autoimmune disease in a patient comprising administering to a patient in need of such treatment or prevention an effective amount of a compound of Formula (IV) or a pharmaceutically acceptable salt thereof, wherein, in the compound of Formula (IV):

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_4$ is a $C_1$–$C_{15}$ straight chain alkyl, -2-pyrrolyl, -3-pyrrolyl, -2-furanyl, -3-furanyl, or —$C_6H_5$, the —$C_6H_5$ being unsubstituted or substituted with one or more methyl, methoxyl, halogen, trifluoromethyl, or methoxycarbonyl groups;

$R_8$ is —H, —$CH_3$, —$CH_2CH_3$, —$CH_2CH_2CH_3$, or —$(CH_2)_3CH_3$; and m is 1 to 4.

For use in the methods for treating or preventing an autoimmune disease, a preferred subclass of the compounds of Formula (IV) are those wherein:

$R_1$ is —H;
$R_2$ is —$CH_3$ or —$CH_2C_6H_5$;
$R_3$ is —$CH_3$;
$R_4$ is —H or a $C_1$–$C_{15}$ straight chain alkyl;
$R_8$ is —H or —$CH_3$; and
m is 2.

For use in the methods for treating or preventing an autoimmune disease, a more preferred subclass of the compounds of Formula (IV) are those wherein:

$R_1$ is —H;
$R_2$, $R_3$, and $R_4$ is —$CH_3$;
$R_8$ is —H or $CH_3$; and
m is 2.

5.5. Formula V

The present invention encompasses novel compounds having the general Formula (V) and pharmaceutically acceptable salts thereof, wherein:

each $R_1$ is independently selected from the group consisting of —H, —$CH_3$, —$CH_2C_6H_5$, —$C(O)OC(CH_3)_3$, and —$C(O)OCH_2C_6H_5$;

$R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;

$R_3$ is —$CH_3$, —$CH_2CH_3$, or —$C_6H_5$;

$R_7$ is —H, a $C_1$–$C_{10}$ straight chain alkyl, or —$CH(CH_3)_2$; and n is 4 to 8.

The compounds of Formula (V) or a pharmaceutically acceptable salt thereof are useful for treating or preventing cancer or neoplastic disease in a patient in need of such treatment or prevention. The compounds of Formula (V) or a pharmaceutically acceptable salt thereof are also useful for inhibiting the growth of a cancer cell or neoplastic cell. The compounds of Formula (V) or a pharmaceutically acceptable salt thereof are useful for treating or preventing a viral infection in a patient in need of such treatment or prevention. The compounds of Formula (V) or a pharmaceutically acceptable salt thereof are also useful for inhibiting the replication or infectivity of a virus. The compounds of Formula (V) or a pharmaceutically acceptable salt thereof are also useful for causing immunosuppression in a patient in need thereof. The compounds of Formula (V) or a pharmaceutically acceptable salt thereof are also useful for treating-an autoimmune disease in a patient in need of such treatment or prevention.

A preferred subclass of the compounds of Formula (V) is that wherein:
$R_1$ is —H;
$R_2$ is —$CH_3$, or —$CH_2C_6H_5$;
$R_3$ is —$CH_3$;
$R_7$ is —H or a $C_1$–$C_4$ straight or branched chain alkyl; and
n is 4.

A more preferred subclass of the compounds of Formula (V) is that wherein:
$R_1$ is —H;
$R_2$ and $R_3$ is —$CH_3$;
$R_7$ is —H, —$C_2H_5$, or -n-$C_4H_9$; and
n is 4.

The present invention also provides compositions comprising a pharmaceutically acceptable carrier and an effective amount of a compound of Formula (V) or a pharmaceutically acceptable salt thereof, wherein, in the compound of Formula (V):
each $R_1$ is independently selected from the group consisting of —H, —$CH_3$, —$CH_2C_6H_5$, —$C(O)OC(CH_3)_3$, and —$C(O)OCH_2C_6H_5$;
$R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;
$R_3$ is —$CH_3$, —$CH_2CH_3$, or —$C_6H_5$;
$R_7$ is —H, a $C_1$–$C_{10}$ straight chain alkyl, or —$CH(CH_3)_2$; and
n is 4 to 8.

The compositions comprising a pharmaceutically acceptable carrier and a compound of Formula (V) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (V) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (V) or a pharmaceutically acceptable salt thereof are also useful for causing immunosuppression in a patient in need thereof. The compositions comprising a pharmaceutically acceptable carrier and a compound of Formula (V) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (V) or a pharmaceutically acceptable salt thereof is that wherein, in the compound of Formula (V):
$R_1$ is —H;
$R_2$ is —$CH_3$, or —$CH_2C_6H_5$;
$R_3$ is —$CH_3$;
$R_7$ is —H or a $C_1$–$C_4$ straight or branched chain alkyl; and
n is 4.

A more preferred subclass of the compositions comprising a pharmaceutically acceptable carrier and a compound of Formula (V) or a pharmaceutically acceptable salt thereof is that wherein, in the compound of Formula (V):
$R_1$ is —H;
$R_2$ and $R_3$ is —$CH_3$;
$R_7$ is —H, —$C_2H_5$, or -n-$C_4H_9$; and
n is 4.

The invention further provides methods for treating or preventing cancer or neoplastic disease in a patient comprising administering to a patient in need of such treatment or prevention an effective amount of a compound of Formula (V) or a pharmaceutically acceptable salt thereof, wherein, in the compound of Formula (V):
each $R_1$ is independently selected from the group consisting of —H, —$CH_3$, —$CH_2C_6H_5$, —$C(O)OC(CH_3)_3$, and —$C(O)OCH_2C_6H_5$;
$R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;
$R_3$ is —$CH_3$, —$CH_2CH_3$, or —$C_6H_5$;
$R_7$ is —H, a $C_1$–$C_{10}$ straight chain alkyl, or —$CH(CH_3)_2$; and
n is 4 to 8.

For use in the methods for treating or preventing cancer or neoplastic disease, a preferred subclass of the compounds of Formula (V) is that wherein, in the compound of Formula (V):
$R_1$ is —H;
$R_2$ is —$CH_3$, or —$CH_2C_6H_5$;
$R_3$ is —$CH_3$;
$R_7$ is —H or a $C_1$–$C_4$ straight or branched chain alkyl; and
n is 4.

For use in the methods for treating or preventing cancer or neoplastic disease, a more preferred subclass of the compounds of Formula (V) is that wherein, in the compound of Formula (V):
$R_1$ is —H;
$R_2$ and $R_3$ is —$CH_3$;
$R_7$ is —H, —$C_2H_5$, or -n-$C_4H_9$; and
n is 4.

The invention further provides methods for inhibiting the growth of a cancer cell or neoplastic cell comprising contacting a cancer cell or neoplastic cell with an effective amount of a compound having the general Formula (V) or a pharmaceutically acceptable salt thereof, wherein, in the compound of Formula (V):
each $R_1$ is independently selected from the group consisting of —H, —$CH_3$, —$CH_2C_6H_5$, —$C(O)OC(CH_3)_3$, and —$C(O)OCH_2C_6H_5$;
$R_2$ is a $C_1$–$C_{10}$ straight chain alkyl or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;
$R_3$ is —$CH_3$, —$CH_2CH_3$, or —$C_6H_5$;
$R_7$ is —H, a $C_1$–$C_{10}$ straight chain alkyl, or —$CH(CH_3)_2$; and
n is 4 to 8.

For use in the methods for inhibiting the growth of a cancer or neoplastic cell, a preferred subclass of the compounds of Formula (V) is that wherein, in the compound of Formula (V):
$R_1$ is —H;
$R_2$ is —$CH_3$, or —$CH_2C_6H_5$;
$R_3$ is —$CH_3$;
$R_7$ is —H or a $C_1$–$C_4$ straight or branched chain alkyl; and
n is 4.

For use in the methods for inhibiting the growth of a cancer or neoplastic cell, a more preferred subclass of the compounds of Formula (V) is that wherein, in the compound of Formula (V):

$R_1$ is —H;
$R_2$ and $R_3$ is —$CH_3$;
$R_7$ is —H, —$C_2H_5$, or -n-$C_4H_9$; and
n is 4.

The invention further provides methods for treating or preventing a viral infection in a patient comprising administering to a patient in need of such treatment or prevention an effective amount of a compound of Formula (V) or a pharmaceutically acceptable salt thereof, wherein, in the compound of Formula (V):
  each $R_1$ is independently selected from the group consisting of —H, —$CH_3$, —$CH_2C_6H_5$, —$C(O)OC(CH_3)_3$, and —$C(O)OCH_2C_6H_5$;
  $R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;
  $R_3$ is —$CH_3$, —$CH_2CH_3$, or —$C_6H_5$;
  $R_7$ is —H, a $C_1$–$C_{10}$ straight chain alkyl, or —$CH(CH_3)_2$; and
  n is 4 to 8.

For use in the present methods for treating or preventing a viral infection, a preferred subclass of the compounds of Formula (V) is that wherein, in the compound of Formula (V):
  $R_1$ is —H;
  $R_2$ is —$CH_3$, or —$CH_2C_6H_5$;
  $R_3$ is —$CH_3$;
  $R_7$ is —H or a $C_1$–$C_4$ straight or branched chain alkyl; and
  n is 4.

For use in the present methods for treating or preventing a viral infection, a more preferred subclass of the compounds of Formula (V) is that wherein, in the compound of Formula (V):
  $R_1$ is —H;
  $R_2$ and $R_3$ is —$CH_3$;
  $R_7$ is —H, —$C_2H_5$, or -n-$C_4H_9$; and
  n is 4.

The invention further provides methods for inhibiting the replication or infectivity of a virus comprising contacting a virus or a virus-infected cell with an effective amount of a compound having the general Formula (V) or a pharmaceutically acceptable salt thereof, wherein, in the compound of Formula (V):
  each $R_1$ is independently selected from the group consisting of —H, —$CH_3$, —$CH_2C_6H_5$, —$C(O)OC(CH_3)_3$, and —$C(O)OCH_2C_6H_5$;
  $R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;
  $R_3$ is —$CH_3$, —$CH_2CH_3$, or —$C_6H_5$;
  $R_7$ is —H, a $C_1$–$C_{10}$ straight chain alkyl, or —$CH(CH_3)_2$; and
  n is 4 to 8.

For use in the methods for inhibiting the replication or infectivity of a virus, a preferred subclass of the compounds of Formula (V) are those wherein:
  $R_1$ is —H;
  $R_2$ is —$CH_3$, or —$CH_2C_6H_5$;
  $R_3$ is —$CH_3$;
  $R_7$ is —H or a $C_1$–$C_4$ straight or branched chain alkyl; and
  n is 4.

For use in the methods for inhibiting the replication or infectivity of a virus, a more preferred subclass of the compounds of Formula (V) are those wherein:
  $R_1$ is —H;
  $R_2$ and $R_3$ is —$CH_3$;
  $R_7$ is —H, —$C_2H_5$, or -n-$C_4H_9$; and
  n is 4.

The invention further provides methods for causing immunosuppression in a patient comprising administering to a patient in need thereof an effective amount of a compound of Formula (V) or a pharmaceutically acceptable salt thereof, wherein, in the compound of Formula (V):
  each $R_1$ is independently selected from the group consisting of —H, —$CH_3$, —$CH_2C_6H_5$, —$C(O)OC(CH_3)_3$, and —$C(O)OCH_2C_6H_5$;
  $R_2$ is a $C_1$–$C_{10}$ straight chain alkyl, or —$CH_2C_6H_5$ the —$CH_2C_6H_5$ being unsubstituted or substituted on the phenyl with one or more methoxyl, halogen, methyl, nitro, trifluoromethyl, or methoxylcarbonyl groups;
  $R_3$ is —$CH_3$, —$CH_2CH_3$, or —$C_6H_5$;
  $R_7$ is —H, a $C_1$–$C_{10}$ straight chain alkyl, or —$CH(CH_3)_2$; and
  n is 4 to 8.

For use in the methods for causing immunosuppression, a preferred subclass of the compounds of Formula (V) are those wherein:
  $R_1$ is —H;
  $R_2$ is —$CH_3$, or —$CH_2C_6H_5$;
  $R_3$ is —$CH_3$;
  $R_7$ is —H or a $C_1$–$C_4$ straight or branched chain alkyl; and
  n is 4.

For use in the methods for causing immunosuppression, a more preferred subclass of the compounds of Formula (V) are those wherein:
  $R_1$ is —H;
  $R_2$ and $R_3$ is —$CH_3$.
  $R_7$ is —H, —$C_2H_5$, or -n-$C_4H_9$; and
  n is 4.

The invention further provides methods for treating or preventing an autoimmune disease in a patient comprising administering to a patient in need of such treatment or prevention an effective amount of a compound of Formula (V) or a pharmaceutically acceptable salt thereof, wherein, in the compound of Formula (V):
  each $R_1$ is independently selected from the group consisting of —H, —$CH_3$, —$CH_2C_6H_5$, —$C(O)OC(CH_3)_3$, and —$C(O)OCH_2C_6H_5$;
  $R_2$ is a $C_1$–$C_{10}$ straight chain alkyl, or —$CH_2C_6H_5$, the —$CH_2C_6H_5$ being unsubstituted or substituted on the phenyl with one or more methoxyl, halogen, methyl, nitro, trifluoromethyl, or methoxylcarbonyl groups;
  $R_3$ is —$CH_3$, —$CH_2CH_3$, or —$C_6H_5$;
  $R_7$ is —H, a $C_1$–$C_{10}$ straight chain alkyl, or —$CH(CH_3)_2$; and
  n is 4 to 8.

For use in the methods for treating or preventing an autoimmune disease, a preferred subclass of the compounds of Formula (V) are those wherein:
  $R_1$ is —H;
  $R_2$ is —$CH_3$, or —$CH_2C_6H_5$;
  $R_3$ is —$CH_3$;
  $R_7$ is —H or a $C_1$–$C_4$ straight or branched chain alkyl; and
  n is 4.

For use in the methods for treating or preventing an autoimmune disease, a more preferred subclass of the compounds of Formula (V) are those wherein:
  $R_1$ is —H;
  $R_2$ and $R_3$ is —$CH_3$;
  $R_7$ is —H, —$C_2H_5$, or -n-$C_4H_9$; and
  n is 4.

5.6. Formula VI

The present invention encompasses novel compounds having the general Formula (VI) and pharmaceutically acceptable salts thereof, wherein:

$R_2$ is a $C_1$–$C_{10}$ straight chain alkyl or —$CH_2C_6H_5$;

$R_3$ is a $C_1$–$C_{10}$ straight chain alkyl, —$CH(CH_3)_2$, —$CH(CH_3)CH_2CH_3$, —$CH(CH_3)CH_2CH_2CH_3$, —$CH(OH)CH_2CH_2CH_3$, —$CH(Cl)CH_2CH_2CH_3$, or —$CH_2C_6H_5$; and n is 1 to 5.

The compounds of Formula (VI) or a pharmaceutically acceptable salt thereof are useful for treating or preventing cancer or neoplastic disease in a patient in need of such treatment or prevention. The compounds of Formula (VI) or a pharmaceutically acceptable salt thereof are also useful for inhibiting the growth of a cancer cell or neoplastic cell. The compounds of Formula (VI) or a pharmaceutically acceptable salt thereof are useful for treating or preventing a viral infection in a patient in need of such treatment or prevention. The compounds of Formula (VI) or a pharmaceutically acceptable salt thereof are also useful for inhibiting the replication or infectivity of a virus. The compounds of Formula (VI) or a pharmaceutically acceptable salt thereof are also useful for causing immunosuppression in a patient in need thereof. The compounds of Formula (VI) or a pharmaceutically acceptable salt thereof are also useful for treating an auto immune disease in a patient in need of such treatment or prevention.

A preferred subclass of the compounds of Formula (VI) is that wherein:

$R_2$ is —$CH_3$, or —$CH_2C_6H_5$;

$R_3$ is —H or $C_1$–$C_4$ straight or branched chain alkyl; and n is 1.

A more preferred subclass of the compounds of Formula (VI) is that wherein:

$R_2$ is —$CH_3$;

$R_3$ is -n-$C_4H_9$; and n is 1.

The present invention also provides compositions comprising a pharmaceutically acceptable carrier and an effective amount of a compound of Formula (VI) or a pharmaceutically acceptable salt thereof, wherein, in the compound of Formula (VI):

$R_2$ is a $C_1$–$C_{10}$ straight chain alkyl or —$CH_2C_6H_5$;

$R_3$ is a $C_1$–$C_{10}$ straight chain alkyl, —$CH(CH_3)_2$, —$CH(CH_3)CH_2CH_3$, —$CH(CH_3)CH_2CH_2CH_3$, —$CH(OH)CH_2CH_2CH_3$, —$CH(Cl)CH_2CH_2CH_3$, or —$CH_2C_6H_5$; and n is 1 to 5.

The compositions comprising a pharmaceutically acceptable carrier and a compound of Formula (VI) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (VI) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (VI) or a pharmaceutically acceptable salt thereof are also useful for causing immunosuppression in a patient in need thereof. The compositions comprising a pharmaceutically acceptable carrier and a compound of Formula (VI) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (VI) or a pharmaceutically acceptable salt thereof is that wherein, in the compound of Formula (VI):

$R_2$ is —$CH_3$, or —$CH_2C_6H_5$;

$R_3$ is —H or $C_1$–$C_4$ straight or branched chain alkyl; and n is 1.

A more preferred subclass of the compositions comprising a pharmaceutically acceptable carrier and a compound of Formula (VI) or a pharmaceutically acceptable salt thereof is that wherein, in the compound of Formula (VI):

$R_2$ is —$CH_3$;

$R_3$ is -n-$C_4H_9$; and n is 1.

The invention further provides methods for treating or preventing cancer or neoplastic disease in a patient comprising administering to a patient in need of such treatment or prevention an effective- amount of a compound of Formula (VI) or a pharmaceutically acceptable salt thereof, wherein, in the compound of Formula (VI):

$R_2$ is a $C_1$–$C_{10}$ straight chain alkyl or —$CH_2C_6H_5$;

$R_3$ is a $C_1$–$C_{10}$ straight chain alkyl, —$CH(CH_3)_2$, —$CH(CH_3)CH_2CH_3$, —$CH(CH_3)CH_2CH_2CH_3$, —$CH(OH)CH_2CH_2CH_3$, —$CH(Cl)CH_2CH_2CH_3$, or —$CH_2C_6H_5$; and n is 1 to 5.

For use in the methods for treating or preventing cancer or neoplastic disease, a preferred subclass of the compounds of Formula (VI) is that wherein, in the compound of Formula (VI):

$R_2$ is —$CH_3$, or —$CH_2C_6H_5$;

$R_3$ is —H or $C_1$–$C_4$ straight or branched chain alkyl; and n is 1.

For use in the methods for treating or preventing cancer or neoplastic disease, a more preferred subclass of the compounds of Formula (VI) is that wherein, in the compound of Formula (VI):

$R_2$ is —$CH_3$;

$R_3$ is -n-$C_4H_9$; and n is 1.

The invention further provides methods for inhibiting the growth of a cancer cell or neoplastic cell comprising contacting a cancer cell or neoplastic cell with an effective amount of a compound having the general Formula (VI) or a pharmaceutically acceptable salt thereof, wherein, in the compound of Formula (VI):

$R_2$ is a $C_1$–$C_{10}$ straight chain alkyl or —$CH_2C_6H_5$;

$R_3$ is a $C_1$–$C_{10}$ straight chain alkyl, —$CH(CH_3)_2$, —$CH(CH_3)CH_2CH_3$, —$CH(CH_3)CH_2CH_2CH_3$, —$CH(OH)CH_2CH_2CH_3$, —$CH(Cl)CH_2CH_2CH_3$, or —$CH_2C_6H_5$; and n is 1 to 5.

For use in the methods for inhibiting the growth of a cancer or neoplastic cell, a preferred subclass of the compounds of Formula (VI) is that wherein, in the compound of Formula (VI):

$R_2$ is —$CH_3$, or —$CH_2C_6H_5$;

$R_3$ is —H or $C_1$–$C_4$ straight or branched chain alkyl; and n is 1.

For use in the methods for inhibiting the growth of a cancer or neoplastic cell, a more preferred subclass of the compounds of Formula (VI) is that wherein, in the compound of Formula (VI):

$R_2$ is —$CH_3$;

$R_3$ is -n-$C_4H_9$; and n is 1.

The invention further provides methods for treating or preventing a viral infection in a patient comprising administering to a patient in need of such treatment or prevention an effective amount of a compound of Formula (VI) or a pharmaceutically acceptable salt thereof, wherein, in the compound of Formula (VI):

$R_2$ is a $C_1$–$C_{10}$ straight chain alkyl or —$CH_2C_6H_5$;
$R_3$ is a $C_1$–$C_{10}$ straight chain alkyl, —$CH(CH_3)_2$, —$CH(CH_3)CH_2CH_3$, —$CH(CH_3)CH_2CH_2CH_3$, —$CH(OH)CH_2CH_2CH_3$, —$CH(Cl)CH_2CH_2CH_3$, or —$CH_2C_6H_5$; and
n is 1 to 5.

For use in the present methods for treating or preventing a viral infection, a preferred subclass of the compounds of Formula (VI) is that wherein, in the compound of Formula (VI):

$R_2$ is —$CH_3$, or —$CH_2C_6H_5$;
$R_3$ is —H or $C_1$–$C_4$ straight or branched chain alkyl; and
n is 1.

For use in the present methods for treating or preventing a viral infection, a more preferred subclass of the compounds of Formula (VI) is that wherein, in the compound of Formula (VI):

$R_2$ is —$CH_3$;
$R_3$ is -n-$C_4H_9$; and
n is 1.

The invention further provides methods for inhibiting the replication or infectivity of a virus comprising contacting a virus or a virus-infected cell with an effective amount of a compound having the general Formula (VI) or a pharmaceutically acceptable salt thereof, wherein, in the compound of Formula (VI):

$R_2$ is a $C_1$–$C_{10}$ straight chain alkyl or —$CH_2C_6H_5$;
$R_3$ is a $C_1$–$C_{10}$ straight chain alkyl, —$CH(CH_3)_2$, —$CH(CH_3)CH_2CH_3$, —$CH(CH_3)CH_2CH_2CH_3$, —$CH(OH)CH_2CH_2CH_3$, —$CH(Cl)CH_2CH_2CH_3$, or —$CH_2C_6H_5$; and
n is 1 to 5.

For use in the methods for inhibiting the replication or infectivity of a virus, a preferred subclass of the compounds of Formula (VI) are those wherein:

$R_2$ is —$CH_3$, or —$CH_2C_6H_5$;
$R_3$ is —H or $C_1$–$C_4$ straight or branched chain alkyl; and
n is 1.

For use in the methods for inhibiting the replication or infectivity of a virus, a more preferred subclass of the compounds of Formula (VI) are those wherein:

$R_2$ is —$CH_3$;
$R_3$ is -n-$C_4H_9$; and
n is 1.

The invention further provides methods for causing immunosuppression in a patient comprising administering to a patient in need thereof an effective amount of a compound of Formula (VI) or a pharmaceutically acceptable salt thereof, wherein, in the compound of Formula (VI):

$R_2$ is a $C_1$–$C_{10}$ straight chain alkyl or —$CH_2C_6H_5$;
$R_3$ is a $C_1$–$C_{10}$ straight chain alkyl, —$CH(CH_3)_2$, —$CH(CH_3)CH_2CH_3$, —$CH(CH_3)CH_2CH_2CH_3$, —$CH(OH)CH_2CH_2CH_3$, —$CH(Cl)CH_2CH_2CH_3$, or —$CH_2C_6H_5$; and
n is 1 to 5.

For use in the methods for causing immunosuppression, a preferred subclass of the compounds of Formula (VI) are those wherein:

$R_2$ is —$CH_3$, or —$CH_2C_6H_5$;
$R_3$ is —H or $C_1$–$C_4$ straight or branched chain alkyl; and
n is 1.

For use in the methods for causing immunosuppression, a more preferred subclass of the compounds of Formula (VI) are those wherein:

$R_2$ is —$CH_3$;
$R_3$ is -n-$C_4H_9$; and
n is 1.

The invention further provides methods for treating or preventing an autoimmune disease in a patient comprising administering to a patient in need of such treatment or prevention an effective amount of a compound of Formula (VI) or a pharmaceutically acceptable salt thereof, wherein, in the compound of Formula (VI):

$R_2$ is a $C_1$–$C_{10}$ straight chain alkyl or —$CH_2C_6H_5$;
$R_3$ is a $C_1$–$C_{10}$ straight chain alkyl, —$CH(CH_3)_2$, —$CH(CH_3)CH_2CH_3$, —$CH(CH_3)CH_2CH_2CH_3$, —$CH(OH)CH_2CH_2CH_3$, —$CH(Cl)CH_2CH_2CH_3$, or —$CH_2C_6H_5$; and
n is 1 to 5.

For use in the methods for treating or preventing an autoimmune disease, a preferred subclass of the compounds of Formula (VI) are those wherein:

$R_2$ is —$CH_3$, or —$CH_2C_6H_5$;
$R_3$ is —H or $C_1$–$C_4$ straight or branched chain alkyl; and
n is 1.

For use in the methods for treating or preventing an autoimmune disease, a more preferred subclass of the compounds of Formula (VI) are those wherein:

$R_2$ is —$CH_3$;
$R_3$ is -n-$C_4H_9$; and
n is 1.

5.7. Formula VII

The present invention encompasses novel compounds having the general Formula (VII) and pharmaceutically acceptable salts thereof, wherein:

$R_2$ is a $C_1$–$C_{10}$ straight chain alkyl or —$CH_2C_6H_5$; and
$R_4$ is —H or a $C_1$–$C_{15}$ straight chain alkyl.

The compounds of Formula (VII) or a pharmaceutically acceptable salt thereof are useful for treating or preventing cancer or neoplastic disease in a patient in need of such treatment or prevention. The compounds of Formula (VII) or a pharmaceutically acceptable salt thereof are also useful for inhibiting the growth of a cancer cell or neoplastic cell. The compounds of Formula (VII) or a pharmaceutically acceptable salt thereof are useful for treating or preventing a viral infection in a patient in need of such treatment or prevention. The compounds of Formula (VII) or a pharmaceutically acceptable salt thereof are also useful for inhibiting the replication or infectivity of a virus. The compounds of Formula (VII) or a pharmaceutically acceptable salt thereof are also useful for causing immunosuppression in a patient in need thereof. The compounds of Formula (VII) or a pharmaceutically acceptable salt thereof are also useful for treating an autoimmune disease in a patient in need of such treatment or prevention.

A preferred subclass of the compounds of Formula (VII) is that wherein:

$R_2$ is —$CH_3$ or —$CH_2C_6H_5$; and
$R_4$ is —H, —$CH_3$, or $(CH_2)_{14}CH_3$.

A more preferred subclass of the compounds of Formula (VII) is that wherein:

$R_2$ is —$CH_3$; and
$R_4$ is —H, —$CH_3$, or $(CH_2)_{14}CH_3$.

The present invention also provides compositions comprising a pharmaceutically acceptable carrier and an effective amount of a compound of Formula (VII) or a pharmaceutically acceptable salt thereof, wherein, in the compound of Formula (VII):

$R_2$ is a $C_1$–$C_{10}$ straight chain alkyl or —$CH_2C_6H_5$; and
$R_4$ is —H or a $C_1$–$C_{15}$ straight chain alkyl.

The compositions comprising a pharmaceutically acceptable carrier and a compound of Formula (VII) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (VII) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (VII) or a pharmaceutically acceptable salt thereof are also useful for causing immunosuppression in a patient in need thereof. The compositions comprising a pharmaceutically acceptable carrier and a compound of Formula (VII) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (VII) or a pharmaceutically acceptable salt thereof is that wherein, in the compound of Formula (VII):
$R_2$ is —$CH_3$ or —$CH_2C_6H_5$; and
$R_4$ is —H, —$CH_3$, or $(CH_2)_{14}CH_3$.

A more preferred subclass of the compositions comprising a pharmaceutically acceptable carrier and a compound of Formula (VII) or a pharmaceutically acceptable salt thereof is that wherein, in the compound of Formula (VII):
$R_2$ is —$CH_3$; and
$R_4$ is —H, —$CH_3$, or $(CH_2)_{14}CH_3$.

The invention further provides methods for treating or preventing cancer or neoplastic disease in a patient comprising administering to a patient in need of such treatment or prevention an effective amount of a compound of Formula (VII) or a pharmaceutically acceptable salt thereof, wherein, in the compound of Formula (VII):
$R_2$ is a $C_1$–$C_{10}$ straight chain alkyl or —$CH_2C_6H_5$; and
$R_4$ is —H or a $C_1$–$C_{15}$ straight chain alkyl.

For use in the methods for treating or preventing cancer or neoplastic disease, a preferred subclass of the compounds of Formula (VII) is that wherein, in the compound of Formula (VII):
$R_2$ is —$CH_3$ or —$CH_2C_6H_5$; and
$R_4$ is —H, —$CH_3$, or $(CH_2)_{14}CH_3$.

For use in the methods for treating or preventing cancer or neoplastic disease, a more preferred subclass of the compounds of Formula (VII) is that wherein, in the compound of Formula (VII):
$R_2$ is —$CH_3$; and
$R_4$ is —H, —$CH_3$, or $(CH_2)_{14}CH_3$.

The invention further provides methods for inhibiting the growth of a cancer cell or neoplastic cell comprising contacting a cancer cell or neoplastic cell with an effective amount of a compound having the general Formula (VII) or a pharmaceutically acceptable salt thereof, wherein, in the compound of Formula (VII):
$R_2$ is a $C_1$–$C_{10}$ straight chain alkyl or —$CH_2C_6H_5$; and
$R_4$ is —H or a $C_1$–$C_{15}$ straight chain alkyl.

For use in the methods for inhibiting the growth of a cancer or neoplastic cell, a preferred subclass of the compounds of Formula (VII) is that wherein, in the compound of Formula (VII):
$R_2$ is —$CH_3$ or —$CH_2C_6H_5$; and
$R_4$ is —H, —$CH_3$, or $(CH_2)_{14}CH_3$.

For use in the methods for inhibiting the growth of a cancer or neoplastic cell, a more preferred subclass of the compounds of Formula (VII) is that wherein, in the compound of Formula (VII):
$R_2$ is —$CH_3$; and
$R_4$ is —H, —$CH_3$, or $(CH_2)_{14}CH_3$.

The invention further provides methods for treating or preventing a viral infection in a patient comprising administering to a patient in need of such treatment or prevention an effective amount of a compound of Formula (VII) or a pharmaceutically acceptable salt thereof, wherein, in the compound of Formula (VII):
$R_2$ is a $C_1$–$C_{10}$ straight chain alkyl or —$CH_2C_6H_5$; and
$R_4$ is —H or a $C_1$–$C_{15}$ straight chain alkyl.

For use in the present methods for treating or preventing a viral infection, a preferred subclass of the compounds of Formula (VII) is that wherein, in the compound of Formula (VII):
$R_2$ is —$CH_3$ or —$CH_2C_6H_5$; and
$R_4$ is —H, —$CH_3$ or $(CH_2)_{14}CH_3$.

For use in the present methods for treating or preventing a viral infection, a more preferred subclass of the compounds of Formula (VII) is that wherein, in the compound of Formula (VII):
$R_2$ is —$CH_3$; and
$R_4$ is —H, —$CH_3$, or $(CH_2)_{14}CH_3$.

The invention further provides methods for inhibiting the replication or infectivity of a virus comprising contacting a virus or a virus-infected cell with an effective amount of a compound having the general Formula (VII) or a pharmaceutically acceptable salt thereof, wherein, in the compound of Formula (VII):
$R_2$ is a $C_1$–$C_{10}$ straight chain alkyl or —$CH_2C_6H_5$; and
$R_4$ is —H or a $C_1$–$C_{15}$ straight chain alkyl.

For use in the methods for inhibiting the replication or infectivity of a virus, a preferred subclass of the compounds of Formula (VII) are those wherein:
$R_2$ is —$CH_3$ or —$CH_2C_6H_5$; and
$R_4$ is —H, —$CH_3$, or $(CH_2)_{14}CH_3$.

For use in the methods for inhibiting the replication or infectivity of a virus, a more preferred subclass of the compounds of Formula (VII) are those wherein:
$R_2$ is —$CH_3$; and
$R_4$ is —H, —$CH_3$, or $(CH_2)_{14}CH_3$.

The invention further provides methods for causing immunosuppression in a patient comprising administering to a patient in need thereof an effective amount of a compound of Formula (VII) or a pharmaceutically acceptable salt thereof, wherein, in the compound of Formula (VII):
$R_2$ is a $C_1$–$C_{10}$ straight chain alkyl or —$CH_2C_6H_5$; and
$R_4$ is —H or a $C_1$–$C_{15}$ straight chain alkyl.

For use in the methods for causing immunosuppression, a preferred subclass of the compounds of Formula (VII) are those wherein:
$R_2$ is —$CH_3$ or —$CH_2C_6H_5$; and
$R_4$ is —H, —$CH_3$, or $(CH_2)_{14}CH_3$.

For use in the methods for causing immunosuppression, a more preferred subclass of the compounds of Formula (VII) are those wherein:
$R_2$ is —$CH_3$; and
$R_4$ is —H, —$CH_3$, or $(CH_2)_{14}CH_3$.

The invention further provides methods for treating or preventing an autoimmune disease in a patient comprising administering to a patient in need of such treatment or prevention an effective amount of a compound of Formula (VII) or a pharmaceutically acceptable salt thereof, wherein, in the compound of Formula (VII):

$R_2$ is a $C_1$–$C_{10}$ straight chain alkyl or —$CH_2C_6H_5$; and
$R_4$ is —H or a $C_1$–$C_{15}$ straight chain alkyl.

For use in the methods treating or preventing an autoimmune disease, a preferred subclass of the compounds of Formula (VII) are those wherein:
$R_2$ is —$CH_3$ or —$CH_2C_6H_5$; and
$R_4$ is —H, —$CH_3$, or $(CH_2)_{14}CH_3$.

For use in the methods for treating or preventing an autoimmune disease, a more preferred subclass of the compounds of Formula (VII) are those wherein:
$R_2$ is —$CH_3$; and
$R_4$ is —H, —$CH_3$, or $(CH_2)_{14}CH_3$.

5.8. Formula VIII

The present invention encompasses novel compounds having the general Formula (VIII) and pharmaceutically acceptable salts thereof, wherein:
$R_2$ is a $C_1$–$C_{10}$ straight chain alkyl or —$CH_2C_6H_5$;
$R_4$ is —H or a $C_1$–$C_{10}$ straight chain alkyl;
$R_5$ is —H or a $C_1$–$C_{10}$ straight chain alkyl; and
m is 1 to 4.

The compounds of Formula (VIII) or a pharmaceutically acceptable salt thereof are useful for treating or preventing cancer or neoplastic disease in a patient in need of such treatment or prevention. The compounds of Formula (VIII) or a pharmaceutically acceptable salt thereof are also useful for inhibiting the growth of a cancer cell or neoplastic cell. The compounds of Formula (VIII) or a pharmaceutically acceptable salt thereof are useful for treating or preventing a viral infection in a patient in need of such treatment or prevention. The compounds of Formula (VII) or a pharmaceutically acceptable salt thereof are also useful for inhibiting the replication or infectivity of a virus. The compounds of Formula (VIII) or a pharmaceutically acceptable salt thereof are also useful for causing immunosuppression in a patient in need thereof. The compounds of Formula (VIII) or a pharmaceutically acceptable salt thereof are also useful for treating an autoimmune disease in a patient in need of such treatment or prevention.

A preferred subclass of the compounds of Formula (VIII) is that wherein:
$R_2$ is —$CH_3$ or —$CH_2C_6H_5$;
$R_4$ and $R_5$ is —H or —$CH_3$; and
m is 2.

A more preferred subclass of the compounds of Formula (VIII) is that wherein:
$R_2$ and $R_5$ is —$CH_3$;
$R_4$ is —H or —$CH_3$; and
m is 2.

The present invention also provides compositions comprising a pharmaceutically acceptable carrier and an effective amount of a compound of Formula (VIII) or a pharmaceutically acceptable salt thereof, wherein, in the compound of Formula (VIII):
$R_2$ is a $C_1$–$C_{10}$ straight chain alkyl or —$CH_2C_6H_5$;
$R_5$ is —H or a $C_1$–$C_{10}$ straight chain alkyl;
$R_4$ is —H or a $C_1$–$C_{10}$ straight chain alkyl; and
m is 1 to 4.

The compositions comprising a pharmaceutically acceptable carrier and a compound of Formula (VIII) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (VIII) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (VIII) or a pharmaceutically acceptable salt thereof are also useful for causing immunosuppression in a patient in need thereof. The compositions comprising a pharmaceutically acceptable carrier and a compound of Formula (VIII) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (VIII) or a pharmaceutically acceptable salt thereof is that wherein, in the compound of Formula (VIII):
$R_2$ is —$CH_3$ or —$CH_2C_6H_5$;
$R_4$ and $R_5$ is —H or —$CH_3$; and
m is 2.

A more preferred subclass of the compositions comprising a pharmaceutically acceptable carrier and a compound of Formula (VIII) or a pharmaceutically acceptable salt thereof is that wherein, in the compound of Formula (VIII):
$R_2$ and $R_5$ is —$CH_3$;
$R_4$ is —H or —$CH_3$; and
m is 2.

The invention further provides methods for treating or preventing cancer or neoplastic disease in a patient comprising administering to a patient in need of such treatment or prevention an effective amount of a compound of Formula (VIII) or a pharmaceutically acceptable salt thereof, wherein, in the compound of Formula (VIII):
$R_2$ is a $C_1$–$C_{10}$ straight chain alkyl or —$CH_2C_6H_5$;
$R_4$ is —H or a $C_1$–$C_{10}$ straight chain alkyl;
$R_5$ is —H or a $C_1$–$C_{10}$ straight chain alkyl; and
m is 1 to 4.

For use in the methods for treating or preventing cancer or neoplastic disease, a preferred subclass of the compounds of Formula (VIII) is that wherein, in the compound of Formula (VIII):
$R_2$ is —$CH_3$ or —$CH_2C_6H_5$;
$R_4$ and $R_5$ is —H or —$CH_3$; and
m is 2.

For use in the methods for treating or preventing cancer or neoplastic disease, a more preferred subclass of the compounds of Formula (VIII) is that wherein, in the compound of Formula (VIII):
$R_2$ and $R_5$ is —$CH_3$;
$R_4$ is —H or —$CH_3$; and
m is 2.

The invention further provides methods for inhibiting the growth of a cancer cell or neoplastic cell comprising contacting a cancer cell or neoplastic cell with an effective amount of a compound having the general Formula (VIII) or a pharmaceutically acceptable salt thereof, wherein, in the compound of Formula (VIII):
$R_2$ is a $C_1$–$C_{10}$ straight chain alkyl or —$CH_2C_6H_5$;
$R_4$ is —H or a $C_1$–$C_{10}$ straight chain alkyl;
$R_5$ is —H or a $C_1$–$C_{10}$ straight chain alkyl; and
m is 1 to 4.

For use in the methods for inhibiting the growth of a cancer or neoplastic cell, a preferred subclass of the compounds of Formula (VIII) is that wherein, in the compound of Formula (VIII):

$R_2$ is —$CH_3$ or —$CH_2C_6H_5$;
$R_4$ and $R_5$ is —H or —$CH_3$; and
m is 2.

For use in the methods for inhibiting the growth of a cancer or neoplastic cell, a more preferred subclass of the compounds of Formula (VIII) is that wherein, in the compound of Formula (VIII):
$R_2$ and $R_5$ is —$CH_3$;
$R_4$ is —H or —$CH_3$; and
m is 2.

The invention further provides methods for treating or preventing a viral infection in a patient comprising administering to a patient in need of such treatment or prevention an effective amount of a compound of Formula (VIII) or a pharmaceutically acceptable salt thereof, wherein, in the compound of Formula (VIII):
$R_2$ is a $C_1$–$C_{10}$ straight chain alkyl or —$CH_2C_6H_5$;
$R_5$ is —H or a $C_1$–$C_{10}$ straight chain alkyl;
$R_4$ is —H or a $C_1$–$C_{10}$ straight chain alkyl; and
m is 1 to 4.

For use in the present methods for treating or preventing a viral infection, a preferred subclass of the compounds of Formula (VIII) is that wherein, in the compound of Formula (VIII):
$R_2$ is —$CH_3$ or —$CH_2C_6H_5$;
$R_4$ and $R_5$ is —H or —$CH_3$; and
m is 2.

For use in the present methods for treating or preventing a viral infection, a more preferred subclass of the compounds of Formula (VIII) is that wherein, in the compound of Formula (VIII):
$R_2$ and $R_5$ is —$CH_3$;
$R_4$ is —H or —$CH_3$; and
m is 2.

The invention further provides methods for inhibiting the replication or infectivity of a virus comprising contacting a virus or a virus-infected cell with an effective amount of a compound having the general Formula (VIII) or a pharmaceutically acceptable salt thereof, wherein, in the compound of Formula (VIII):
$R_2$ is a $C_1$–$C_{10}$ straight chain alkyl or —$CH_2C_6H_5$;
$R_4$ is —H or a $C_1$–$C_{10}$ straight chain alkyl;
$R_5$ is —H or a $C_1$–$C_{10}$ straight chain alkyl; and
m is 1 to 4.

For use in the methods for inhibiting the replication or infectivity of a virus, a preferred subclass of the compounds of Formula (VIII) are those wherein:
$R_2$ is —$CH_3$ or —$CH_2C_6H_5$;
$R_4$ and $R_5$ is —H or —$CH_3$; and
m is 2.

For use in the methods for inhibiting the replication or infectivity of a virus, a more preferred subclass of the compounds of Formula (VIII) are those wherein:
$R_2$ and $R_5$ is —$CH_3$;
$R_4$ is —H or —$CH_3$; and
m is 2.

The invention further provides methods for causing immunosuppression in a patient comprising administering to a patient in need thereof an effective amount of a compound of Formula (VIII) or a pharmaceutically acceptable salt thereof, wherein, in the compound of Formula (VIII):
$R_2$ is a $C_1$–$C_{10}$ straight chain alkyl or —$CH_2C_6H_5$;
$R_4$ is —H or a $C_1$–$C_{10}$ straight chain alkyl;
$R_5$ is —H or a $C_1$–$C_{10}$ straight chain alkyl; and
m is 1 to 4.

For use in the methods for causing immunosuppression, a preferred subclass of the compounds of Formula (VIII) are those wherein:
$R_2$ is —$CH_3$ or —$CH_2C_6H_5$;
$R_4$ and $R_5$ is —H or —$CH_3$; and
m is 2.

For use in the methods for causing immunosuppression, a more preferred subclass of the compounds of Formula (VIII) are those wherein:
$R_2$ and $R_5$ is —$CH_3$;
$R_4$ is —H or —$CH_3$; and
m is 2.

The invention further provides methods for treating or preventing an autoimmune disease in a patient comprising administering to a patient in need of such treatment or prevention an effective amount of a compound of Formula (VIII) or a pharmaceutically acceptable salt thereof, wherein, in the compound of Formula (VIII):
$R_2$ is a $C_1$–$C_{10}$ straight chain alkyl or —$CH_2C_6H_5$;
$R_4$ is —H or a $C_1$–$C_{10}$ straight chain alkyl;
$R_5$ is —H or a $C_1$–$C_{10}$ straight chain alkyl; and
m is 1 to 4.

For use in the methods for treating or preventing an autoimmune disease, a preferred subclass of the compounds of Formula (VIII) are those wherein:
$R_2$ is —$CH_3$ or —$CH_2C_6H_5$;
$R_4$ and $R_5$ is —H or —$CH_3$; and
m is 2.

For use in the methods for treating or preventing an autoimmune disease, a more preferred subclass of the compounds of Formula (VIII) are those wherein:
$R_2$ and $R_5$ is —$CH_3$;
$R_4$ is —H or —$CH_3$; and
m is 2.

5.9. Formula IX

The present invention encompasses novel compounds having the general Formula (IX) and pharmaceutically acceptable salts thereof, wherein:
$R_1$ is —H, —$CH_3$, —$SO_2$-4-methylphenyl, —$CH_2C_6H_5$, —$Si(R_5R_6R_7)$, —$CH_2OCH_2CH_2SiCH_3$, —$C(O)OC(CH_3)_3$, or —$C(O)CH_2C_6H_5$;
$R_2$ is —$CH_3$, —$CH_2CH_3$, —$CH_2CH_2CH_3$, or —$CH_2C_6H_5$;
$R_3$ is —H or Cl;
$R_4$ is —H or a $C_1$–$C_{10}$ straight chain alkyl;
$R_5$ is a $C_1$–$C_4$ straight or branched chain alkyl or —$C_6H_5$;
$R_6$ is a $C_1$–$C_3$ straight or branched chain alkyl;
$R_7$ is a $C_1$–$C_3$ straight or branched chain alkyl; and
n is 1 to 5.

The compounds of Formula (IX) or a pharmaceutically acceptable salt thereof are useful for treating or preventing cancer or neoplastic disease in a patient in need of such treatment or prevention. The compounds of Formula (IX) or a pharmaceutically acceptable salt thereof are also useful for inhibiting the growth of a cancer cell or neoplastic cell. The compounds of Formula (IX) or a pharmaceutically acceptable salt thereof are useful for treating or preventing a viral infection in a patient in need of such treatment or prevention. The compounds of Formula (IX) or a pharmaceutically acceptable salt thereof are also useful for inhibiting the replication or infectivity of a virus. The compounds of Formula (IX) or a pharmaceutically acceptable salt thereof are also useful for causing immunosuppression in a patient in need thereof. The compounds of Formula (IX) or a pharmaceutically acceptable salt thereof are also useful for treating an autoimmune disease in a patient in need of such treatment or prevention.

A preferred subclass of the compounds of Formula (IX) is that wherein:
$R_1$ is —H;
$R_2$ is —$CH_3$ or —$CH_2C_6H_5$;
$R_3$ is —H;
$R_4$ is —H or a $C_1$–$C_4$ straight or branched chain alkyl; and
n is 1 to 3.

A more preferred subclass of the compounds of Formula (IX) is that wherein:
$R_1$ is —H;
$R_2$ is —$CH_3$;
$R_3$ is —H;
$R_4$ is —$C_4H_9$; and
n is 1.

Another more preferred subclass of the compounds of Formula (IX) is that wherein:
$R_1$ is —H;
$R_2$ is —$CH_3$;
$R_3$ is —H;
$R_4$ is —$C_2H_5$; and
n is 3.

The present invention also provides compositions comprising a pharmaceutically acceptable carrier and an effective amount of a compound of Formula (IX) or a pharmaceutically acceptable salt thereof, wherein, in the compound of Formula (IX):
$R_1$ is —H, —$CH_3$, —$SO_2$-4-methylphenyl, —$CH_2C_6H_5$, —$Si(R_5R_6R_7)$, —$CH_2OCH_2CH_2SiCH_3$, —$C(O)OC(CH_3)_3$, or —$C(O)CH_2C_6H_5$;
$R_2$ is —$CH_3$, —$CH_2CH_3$, —$CH_2CH_2CH_3$, or —$CH_2C_6H_5$;
$R_3$ is —H or Cl;
$R_4$ is —H or a $C_1$–$C_{10}$ straight chain alky;
$R_5$ is a $C_1$–$C_4$ straight or branched chain alkyl or —$C_6H_5$;
$R_6$ is a $C_1$–$C_3$ straight or branched chain alkyl;
$R_7$ is a $C_1$–$C_3$ straight or branched chain alkyl; and
n is 1 to 5.

The compositions comprising a pharmaceutically acceptable carrier and a compound of Formula (IX) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (IX) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (IX) or a pharmaceutically acceptable salt thereof are also useful for causing immunosuppression in a patient in need thereof. The compositions comprising a pharmaceutically acceptable carrier and a compound of Formula (IX) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (IX) or a pharmaceutically acceptable salt thereof is that wherein, in the compound of Formula (IX):
$R_1$ is —H;
$R_2$ is —$CH_3$ or —$CH_2C_6H_5$;
$R_3$ is —H;
$R_4$ is —H or a $C_1$–$C_4$ straight or branched chain alkyl; and
n is 1 to 3.

A more preferred subclass of the compositions comprising a pharmaceutically acceptable carrier and a compound of Formula (IX) or a pharmaceutically acceptable salt thereof is that wherein, in the compound of Formula (I):
$R_1$ is —H;
$R_2$ is —$CH_3$;
$R_3$ is —H;
$R_4$ is —$C_4H_9$; and
n is 1.

Another more preferred subclass of the compositions comprising a pharmaceutically acceptable carrier and a compound of Formula (IX) or a pharmaceutically acceptable salt thereof is that wherein, in the compound of Formula (IX):
$R_1$ is —H;
$R_2$ is —$CH_3$;
$R_3$ is —H;
$R_4$ is —$C_2H_5$; and
n is 3.

The invention further provides methods for treating or preventing cancer or neoplastic disease in a patient comprising administering to a patient in need of such treatment or prevention an effective amount of a compound of Formula (IX) or a pharmaceutically acceptable salt thereof, wherein, in the compound of Formula (IX) $R_1$ is —H, —$CH_3$, —$SO_2$-4-methylphenyl, —$CH_2C_6H_5$, —$Si(R_5R_6R_7)$, —$CH_2OCH_2CH_2SiCH_3$, —$C(O)OC(CH_3)_3$, or —$C(O)CH_2C_6H_5$;
$R_2$ is —$CH_3$, —$CH_2CH_3$, —$CH_2CH_2CH_3$, or —$CH_2C_6H_5$;
$R_3$ is —H or Cl;
$R_4$ is —H or a $C_1$–$C_{10}$ straight chain alkyl;
$R_5$ is a $C_1$–$C_4$ straight or branched chain alkyl or —$C_6H_5$;
$R_6$ is a $C_1$–$C_3$ straight or branched chain alkyl;
$R_7$ is a $C_1$–$C_3$ straight or branched chain alkyl; and
n is 1 to 5.

For use in the methods for treating or preventing cancer or neoplastic disease, a preferred subclass of the compounds of Formula (IX) is that wherein, in the compound of Formula (IX):
$R_1$ is —H;
$R_2$ is —$CH_3$ or —$CH_2C_6H_5$;
$R_3$ is —H;
$R_4$ is —H or a $C_1$–$C_4$ straight or branched chain alkyl; and
n is 1 to 3.

For use in the methods for treating or preventing cancer or neoplastic disease, a more preferred subclass of the compounds of Formula (IX) is that wherein, in the compound of Formula (IX):
$R_1$ is —H;
$R_2$ is —$CH_3$;
$R_3$ is —H;
$R_4$ is —$C_4H_9$; and
n is 1.

For use in the methods for treating or preventing cancer or neoplastic disease, another more preferred subclass of the compounds of Formula (IX) is that wherein, in the compound of Formula (XI):
$R_1$ is —H;
$R_2$ is —$CH_3$;
$R_3$ is —H;
$R_4$ is —$C_2H_5$; and
n is 3.

The invention further provides methods for inhibiting the growth of a cancer cell or neoplastic cell comprising contacting a cancer cell or neoplastic cell with an effective amount of a compound having the general Formula (IX) or a pharmaceutically acceptable salt thereof, wherein, in the compound of Formula (IX):

$R_1$ is —H, —$CH_3$, —$SO_2$-4-methylphenyl, —$CH_2C_6H_5$, —$Si(R_5R_6R_7)$, —$CH_2OCH_2CH_2SiCH_3$, —$C(O)OC(CH_3)_3$, or —$C(O)CH_2C_6H_5$;

$R_2$ is —$CH_3$, —$CH_2CH_3$, —$CH_2CH_2CH_3$, or —$CH_2C_6H_5$;

$R_3$ is —H or Cl;

$R_4$ is —H or a $C_1$–$C_{10}$ straight chain alkyl;

$R_5$ is a $C_1$–$C_4$ straight or branched chain alkyl or —$C_6H_5$;

$R_6$ is a $C_1$–$C_3$ straight or branched chain alkyl;

$R_7$ is a $C_1$–$C_3$ straight or branched chain alkyl; and n is 1 to 5.

For use in the methods for inhibiting the growth of a cancer or neoplastic cell, a preferred subclass of the compounds of Formula (IX) is that wherein, in the compound of Formula (IX):

$R_1$ is —H;

$R_2$ is —$CH_3$ or —$CH_2C_6H_5$;

$R_3$ is —H;

$R_4$ is —H or a $C_1$–$C_4$ straight or branched chain alkyl; and n is 1 to 3.

For use in the methods for inhibiting the growth of a cancer or neoplastic cell, a more preferred subclass of the compounds of Formula (IX) is that wherein, in the compound of Formula (IX):

$R_1$ is —H;

$R_2$ is —$CH_3$;

$R_3$ is —H;

$R_4$ is —$C_4H_9$; and n is 1.

For use in the methods for inhibiting the growth of a cancer or neoplastic cell, another more preferred subclass of the compounds of Formula (IX) is that wherein, in the compound of Formula (IX):

$R_1$ is —H;

$R_2$ is —$CH_3$;

$R_3$ is —H;

$R_4$ is —$C_2H_5$; and n is 3.

The invention further provides methods for treating or preventing a viral infection in a patient comprising administering to a patient in need of such treatment or prevention an effective amount of a compound of Formula (IX) or a pharmaceutically acceptable salt thereof, wherein, in the compound of Formula (IX):

$R_1$ is —H, —$CH_3$, —$SO_2$-4-methylphenyl, —$CH_2C_6H_5$, —$Si(R_5R_6,R_7)$, —$CH_2OCH_2CH_2SiCH_3$, —$C(O)OC(CH_3)_3$, or —$C(O)CH_2C_6H_5$;

$R_2$ is —$CH_3$, —$CH_2CH_3$, —$CH_2CH_2CH_3$, or —$CH_2C_6H_5$;

$R_3$ is —H or Cl;

$R_4$ is —H or a $C_1$–$C_{10}$ straight chain alkyl;

$R_5$ is a $C_1$–$C_4$ straight or branched chain alkyl or —$C_6H_5$;

$R_6$ is a $C_1$–$C_3$ straight or branched chain alkyl;

$R_7$ is a $C_1$–$C_3$ straight or branched chain alkyl; and n is 1 to 5.

For use in the present methods for treating or preventing a viral infection, a preferred subclass of the compounds of Formula (IX) is that wherein, in the compound of Formula (IX):

$R_1$ is —H;

$R_2$ is —$CH_3$ or —$CH_2C_6H$;

$R_3$ is —H;

$R_4$ is —H or a $C_1$–$C_4$ straight or branched chain alkyl; and n is 1 to 3.

For use in the present methods for treating or preventing a viral infection, a more preferred subclass of the compounds of Formula (IX) is that wherein, in the compound of Formula (IX):

$R_1$ is —H;

$R_2$ is —$CH_3$;

$R_3$ is —H;

$R_4$ is —$C_4H_9$; and n is 1.

For use in the present methods for treating or preventing a viral infection, another more preferred subclass of the compounds of Formula (IX) is that wherein, in the compound of Formula (IX):

$R_1$ is —H;

$R_2$ is —$CH_3$;

$R_3$ is —H;

$R_4$ is —$C_2H_5$; and n is 3.

The invention further provides methods for inhibiting the replication or infectivity of a virus comprising contacting a virus or a virus-infected cell with an effective amount of a compound having the general Formula (IX) or a pharmaceutically acceptable salt thereof, wherein, in the compound of Formula (IX):

$R_1$ is —H, —$CH_3$, —$SO_2$-4-methylphenyl, —$CH_2C_6H_5$, —$Si(R_5R_6R_7)$, —$CH_2OCH_2CH_2SiCH_3$, —$C(O)OC(CH_3)_3$, or —$C(O)CH_2C_6H_5$;

$R_2$ is —$CH_3$, —$CH_2CH_3$, —$CH_2CH_2CH_3$, or —$CH_2C_6H_5$;

$R_3$ is —H or Cl;

$R_4$ is —H or a $C_1$–$C_{10}$ straight chain alkyl;

$R_5$ is a $C_1$–$C_4$ straight or branched chain alkyl or —$C_6H_5$;

$R_6$ is a $C_1$–$C_3$ straight or branched chain alkyl;

$R_7$ is a $C_1$–$C_3$ straight or branched chain alkyl; and n is 1 to 5.

For use in the methods for inhibiting the replication or infectivity of a virus, a preferred subclass of the compounds of Formula (IX) are those wherein:

$R_1$ is —H;

$R_2$ is —$CH_3$ or —$CH_2C_6H_5$;

$R_3$ is —H;

$R_4$ is —H or a $C_1$–$C_4$ straight or branched chain alkyl; and n is 1 to 3.

For use in the methods for inhibiting the replication or infectivity of a virus, a more preferred subclass of the compounds of Formula (IX) are those wherein:

$R_1$ is —H;

$R_2$ is —$CH_3$;

$R_3$ is —H;

$R_4$ is —$C_4H_9$; and n is 1.

For use in the methods for inhibiting the replication or infectivity of a virus, another more preferred subclass of the compounds of Formula (IX) are those wherein:

$R_1$ is —H;

$R_2$ is —$CH_3$;

$R_3$ is —H;

$R_4$ is —$C_2H_5$; and n is 3.

The invention further provides methods for causing immunosuppression in a patient comprising administering to a patient in need thereof an effective amount of a compound of Formula (IX) or a pharmaceutically acceptable salt thereof, wherein, in the compound of Formula (IX):

$R_1$ is —H, —$CH_3$, —$SO_2$-4-methylphenyl, —$CH_2C_6H_5$, —$Si(R_5R_6R_7)$, —$CH_2OCH_2CH_2SiCH_3$, —$C(O)OC(CH_3)_3$, or —$C(O)CH_2C_6H_5$;

$R_2$ is —$CH_3$, —$CH_2CH_3$, —$CH_2CH_2CH_3$, or —$CH_2C_6H_5$;

$R_3$ is —H or Cl;

$R_4$ is —H or a $C_1$–$C_{10}$ straight chain alkyl;

$R_5$ is a $C_1$–$C_4$ straight or branched chain alkyl or —$C_6H_5$;

$R_6$ is a $C_1$–$C_3$ straight or branched chain alkyl;

$R_7$ is a $C_1$–$C_3$ straight or branched chain alkyl; and n is 1 to 5.

For use in the methods for causing immunosuppression, a preferred subclass of the compounds of Formula (IX) are those wherein:

$R_1$ is —H;
$R_2$ is —$CH_3$ or —$CH_2C_6H_5$;
$R_3$ is —H;
$R_4$ is —H or a $C_1$–$C_4$ straight or branched chain alkyl; and
n is 1 to 3.

For use in the methods for causing immunosuppression, a more preferred subclass of the compounds of Formula (IX) are those wherein:

$R_1$ is —H;
$R_2$ is —$CH_3$;
$R_3$ is —H;
$R_4$ is —$C_4H_9$; and
n is 1.

For use in the methods for causing immunosuppression, another more preferred subclass of the compounds of Formula (IX) are those wherein:

$R_1$ is —H;
$R_2$ is —$CH_3$;
$R_3$ is —H;
$R_4$ is —$C_2H_5$; and
n is 3.

The invention further provides methods for treating or preventing an autoimmune disease in a patient comprising administering to a patient in need of such treatment or prevention an effective amount of a compound of Formula (IX) or a pharmaceutically acceptable salt thereof, wherein, in the compound of Formula (IX):

$R_1$ is —H, —$CH_3$, —$SO_2$-4-methylphenyl, —$CH_2C_6H_5$, —$Si(R_5R_6R_7)$, —$CH_2OCH_2CH_2SiCH_3$, —$C(O)OC(CH_3)_3$, or —$C(O)CH_2C_6H_5$;

$R_2$ is —$CH_3$, —$CH_2CH_3$, —$CH_2CH_2CH_3$, or —$CH_2C_6H_5$;

$R_3$ is —H or Cl;

$R_4$ is —H or a $C_1$–$C_{10}$ straight chain alkyl;

$R_5$ is a $C_1$–$C_4$ straight or branched chain alkyl or —$C_6H_5$;

$R_6$ is a $C_1$–$C_3$ straight or branched chain alkyl;

$R_7$ is a $C_1$–$C_3$ straight or branched chain alkyl; and n is 1 to 5.

For use in the methods for treating or preventing an autoimmune disease, a preferred subclass of the compounds of Formula (IX) are those wherein:

$R_1$ is —H;
$R_2$ is —$CH_3$ or —$CH_2C_6H_5$;
$R_3$ is —H;
$R_4$ is —H or a $C_1$–$C_4$ straight or branched chain alkyl; and
n is 1 to 3.

For use in the methods for treating or preventing an autoimmune disease, a more preferred subclass of the compounds of Formula (IX) are those wherein:

$R_1$ is —H;
$R_2$ is —$CH_3$;
$R_3$ is —H;
$R_4$ is —$C_4H_9$; and
n is 1.

For use in the methods for treating or preventing an autoimmune disease, another more preferred subclass of the compounds of Formula (IX) are those wherein:

$R_1$ is —H;
$R_2$ is —$CH_3$;
$R_3$ is —H;
$R_4$ is —$C_2H_5$; and
n is 3.

5.10. Formula X

The present invention encompasses novel compounds having the general Formula (X) and pharmaceutically acceptable salts thereof, wherein:

$R_1$ is —H, —$CH_3$, —$CH_2C_6H_5$, —$COCH_3$, —$C(O)OC(CH_3)_3$, or —$C(O)CH_2C_6H_5$;

$R_2$ is a $C_1$–$C_{10}$ straight chain alkyl or —$CH_2C_6H_5$, the —$CH_2C_6H_5$ being unsubstituted or substituted with one or more halo, methoxyl, methyl, methoxycarbonyl, or nitro groups;

$R_3$ is —H, —$CH_3$, —$CH_2C_6H_5$, or —$C(O)OC(CH_3)_3$;

$R_4$ is —H or —$CH_3$;

$R_5$ is —H, —$CH_3$, —$OCH_3$, —F, —Cl, —Br, —I, —CN, —$NH_2$; —$NH(C_1$–$C_3$ straight or branched chain alkyl), —$NHCOCH_3$, —$NO_2$, —COOH, —$COOR_6$, —OH, or —$OCH_2C_6H_5$; and $R_6$ is a $C_1$–$C_6$ straight chain alkyl.

The compounds of Formula (X) or a pharmaceutically acceptable salt thereof are useful for treating or preventing cancer or neoplastic disease in a patient in need of such treatment or prevention. The compounds of Formula (X) or a pharmaceutically acceptable salt thereof are also useful for inhibiting the growth of a cancer cell or neoplastic cell. The compounds of Formula (X) or a pharmaceutically acceptable salt thereof are useful for treating or preventing a viral infection in a patient in need of such treatment or prevention. The compounds of Formula (X) or a pharmaceutically acceptable salt thereof are also useful for inhibiting the replication or infectivity of a virus. The compounds of Formula (X) or a pharmaceutically acceptable salt thereof are also useful for causing immunosuppression in a patient in need thereof. The compounds of Formula (X) or a pharmaceutically acceptable salt thereof are also useful for treating an autoimmune disease in a patient in need of such treatment or prevention.

A preferred subclass of the compounds of Formula (X) is that wherein:

$R_1$ is —H;
$R_2$ is —$CH_3$ or —$CH_2C_6H_5$;
$R_3$ is —H;
$R_4$ is —H or —$CH_3$;
$R_5$ is —H, halogen, or —$COOR_6$; and
$R_6$ is —$CH_3$.

A more preferred subclass of the compounds of Formula (X) is that wherein:

$R_1$ is —H;
$R_2$ is —$CH_3$;
$R_3$ is —H;
$R_4$ is —H or —$CH_3$; and
$R_5$ is —H.

The present invention also provides compositions comprising a pharmaceutically acceptable carrier and an effective amount of a compound of Formula (X) or a pharmaceutically acceptable salt thereof, wherein, in the compound of Formula (X):

$R_1$ is —H, —CH$_3$, —CH$_2$C$_6$H$_5$, —COCH$_3$, —C(O)OC(CH$_3$)$_3$, or —C(O)CH$_2$C$_6$H$_5$;

$R_2$ is a C$_1$–C$_{10}$ straight chain alkyl or —CH$_2$C$_6$H$_5$, the —CH$_2$C$_6$H$_5$ being unsubstituted or substituted with one or more halo, methoxyl, methyl, methoxycarbonyl, or nitro groups;

$R_3$ is —H, —CH$_3$, —CH$_2$C$_6$H$_5$, or —C(O)OC(CH$_3$)$_3$;

$R_4$ is —H or —CH$_3$;

$R_5$ is —H, —CH$_3$, —OCH$_3$, —F, —Cl, —Br, —I, —CN, —NH$_2$; —NH(C$_1$–C$_3$ straight or branched chain alkyl), —NHCOCH$_3$, —NO$_2$, —COOH, —COOR$_6$, —OH, or —OCH$_2$C$_6$H$_5$; and $R_6$ is a C$_1$–C$_6$ straight chain alkyl.

The compositions comprising a pharmaceutically acceptable carrier and a compound of Formula (X) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (X) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (X) or a pharmaceutically acceptable salt thereof are also useful for causing immunosuppression in a patient in need thereof. The compositions comprising a pharmaceutically acceptable carrier and a compound of Formula (X) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (X) or a pharmaceutically acceptable salt thereof is that wherein, in the compound of Formula (X):

$R_1$ is —H;

$R_2$ is —CH$_3$ or —CH$_2$C$_6$H$_5$;

$R_3$ is —H;

$R_4$ is —H or —CH$_3$;

$R_5$ is —H, halogen, or —COOR$_6$; and $R_6$ is —CH$_3$.

A more preferred subclass of the compositions comprising a pharmaceutically acceptable carrier and a compound of Formula (X) or a pharmaceutically acceptable salt thereof is that wherein, in the compound of Formula (X):

$R_1$ is —H;

$R_2$ is —CH$_3$;

$R_3$ is —H;

$R_4$ is —H or —CH$_3$; and $R_5$ is —H.

The invention further provides methods for treating or preventing cancer or neoplastic disease in a patient comprising administering to a patient in need of such treatment or prevention an effective amount of a compound of Formula (X) or a pharmaceutically acceptable salt thereof, wherein, in the compound of Formula (X):

$R_1$ is —H, —CH$_3$, —CH$_2$C$_6$H$_5$, —COCH$_3$, —C(O)OC(CH$_3$)$_3$, or —C(O)CH$_2$C$_6$H$_5$;

$R_2$ is a C$_1$–C$_{10}$ straight chain alkyl or —CH$_2$C$_6$H$_5$, the —CH$_2$C$_6$H$_5$ being unsubstituted or substituted with one or more halo, methoxyl, methyl, methoxycarbonyl, or nitro groups;

$R_3$ is —H, —CH$_3$, —CH$_2$C$_6$H$_5$, or —C(O)OC(CH$_3$)$_3$;

$R_4$ is —H or —CH$_3$;

$R_5$ is —H, —CH$_3$, —OCH$_3$, —F, —Cl, —Br, —I, —CN, —NH$_2$; —NH(C$_1$–C$_3$ straight or branched chain alkyl), —NHCOCH$_3$, —NO$_2$, —COOH, —COOR$_6$, —OH, or —OCH$_2$C$_6$H$_5$; and $R_6$ is a C$_1$–C$_6$ straight chain alkyl.

For use in the methods for treating or preventing cancer or neoplastic disease, a preferred subclass of the compounds of Formula (X) is that wherein, in the compound of Formula (X):

$R_1$ is —H;

$R_2$ is —CH$_3$ or —CH$_2$C$_6$H$_5$;

$R_3$ is —H;

$R_4$ is —H or —CH$_3$;

$R_5$ is —H, halogen, or —COOR$_6$; and $R_6$ is —CH$_3$.

For use in the methods for treating or preventing cancer or neoplastic disease, a more preferred subclass of the compounds of Formula (X) is that wherein, in the compound of Formula (X):

$R_1$ is —H;

$R_2$ is —CH$_3$;

$R_3$ is —H;

$R_4$ is —H or —CH$_3$; and $R_5$ is —H.

The invention further provides methods for inhibiting the growth of a cancer cell or neoplastic cell comprising contacting a cancer cell or neoplastic cell with an effective amount of a compound having the general Formula (X) or a pharmaceutically acceptable salt thereof, wherein, in the compound of Formula (X):

$R_1$ is —H, —CH$_3$, —CH$_2$C$_6$H$_5$, —COCH$_3$, —C(O)OC(CH$_3$)$_3$, or —C(O)CH$_2$C$_6$H$_5$;

$R_2$ is a C$_1$–C$_{10}$ straight chain alkyl or —CH$_2$C$_6$H$_5$, the —CH$_2$C$_6$H$_5$ being unsubstituted or substituted with one or more halo, methoxyl, methyl, methoxycarbonyl, or nitro groups;

$R_3$ is —H, —CH$_3$, —CH$_2$C$_6$H$_5$, or —C(O)OC(CH$_3$)$_3$;

$R_4$ is —H or —CH$_3$;

$R_5$ is —H, —CH$_3$, —OCH$_3$, —F, —Cl, —Br, —I, —CN, —NH$_2$; —NH(C$_1$–C$_3$ straight or branched chain alkyl), —NHCOCH$_3$, —NO$_2$, —COOH, —COOR$_6$, —OH, or —OCH$_2$C$_6$H$_5$; and $R_6$ is a C$_1$–C$_6$ straight chain alkyl.

For use in the methods for inhibiting the growth of a cancer or neoplastic cell, a preferred subclass of the compounds of Formula (X) is that wherein, in the compound of Formula (X):

$R_1$ is —H;

$R_2$ is —CH$_3$ or —CH$_2$C$_6$H$_5$;

$R_3$ is —H;

$R_4$ is —H or —CH$_3$;

$R_5$ is —H, halogen, or —COOR$_6$; and $R_6$ is —CH$_3$.

For use in the methods for inhibiting the growth of a cancer or neoplastic cell, a more preferred subclass of the compounds of Formula (X) is that wherein, in the compound of Formula (X):

$R_1$ is —H;

$R_2$ is —CH$_3$;

$R_3$ is —H;

$R_4$ is —H or —CH$_3$; and $R_5$ is —H.

The invention further provides methods for treating or preventing a viral infection in a patient comprising administering to a patient in need of such treatment or prevention an effective amount of a compound of Formula (X) or a pharmaceutically acceptable salt thereof, wherein, in the compound of Formula (X):
$R_1$ is —H, —$CH_3$, —$CH_2C_6H_5$, —$COCH_3$, —C(O)OC$(CH_3)_3$, or —C(O)$CH_2C_6H_5$;
$R_2$ is a $C_1$–$C_{10}$ straight chain alkyl or —$CH_2C_6H_5$, the —$CH_2C_6H_5$ being unsubstituted or substituted with one or more halo, methoxyl, methyl, methoxycarbonyl, or nitro groups;
$R_3$ is —H, —$CH_3$, —$CH_2C_6H_5$, or —C(O)OC$(CH_3)_3$;
$R_4$ is —H or —$CH_3$;
$R_5$ is —H, —$CH_3$, —$OCH_3$, —F, —Cl, —Br, —I, —CN, —$NH_2$; —NH($C_1$–$C_3$ straight or branched chain alkyl), —NHCOCH$_3$, —NO$_2$, —COOH, —COOR$_6$, —OH, or —OCH$_2$C$_6$H$_5$; and
$R_6$ is a $C_1$–$C_6$ straight chain alkyl.

For use in the present methods for treating or preventing a viral infection, a preferred subclass of the compounds of Formula (X) is that wherein, in the compound of Formula (X):
$R_1$ is —H;
$R_2$ is —$CH_3$ or —$CH_2C_6H_5$;
$R_3$ is —H;
$R_4$ is —H or —$CH_3$;
$R_5$ is —H, halogen, or —COOR$_6$; and
$R_6$ is —$CH_3$.

For use in the present methods for treating or preventing a viral infection, a more preferred subclass of the compounds of Formula (X) is that wherein, in the compound of Formula (X):
$R_1$ is —H;
$R_2$ is —$CH_3$;
$R_3$ is —H;
$R_4$ is —H or —$CH_3$; and
$R_5$ is —H.

The invention further provides methods for inhibiting the replication or infectivity of a virus comprising contacting a virus or a virus-infected cell with an effective amount of a compound having the general Formula (X) or a pharmaceutically acceptable salt thereof, wherein, in the compound of Formula (X):
$R_1$ is —H, —$CH_3$, —$CH_2C_6H_5$, —$COCH_3$, —C(O)OC$(CH_3)_3$, or —C(O)$CH_2C_6H_5$;
$R_2$ is a $C_1$–$C_{10}$ straight chain alkyl or —$CH_2C_6H_5$, the —$CH_2C_6H_5$ being unsubstituted or substituted with one or more halo, methoxyl, methyl, methoxycarbonyl, or nitro groups;
$R_3$ is —H, —$CH_3$, —$CH_2C_6H_5$, or —C(O)OC$(CH_3)_3$;
$R_4$ is —H or —$CH_3$;
$R_5$ is —H, —$CH_3$, —$OCH_3$, —F, —Cl, —Br, —I, —CN, —$NH_2$; —NH($C_1$–$C_3$ straight or branched chain alkyl), —NHCOCH$_3$, —NO$_2$, —COOH, —COOR$_6$, —OH, or —OCH$_2$C$_6$H$_5$; and
$R_6$ is a $C_1$–$C_6$ straight chain alkyl.

For use in the methods for inhibiting the replication or infectivity of a virus, a preferred subclass of the compounds of Formula (X) are those wherein:
$R_1$ is —H;
$R_2$ is —$CH_3$ or —$CH_2C_6H_5$;
$R_3$ is —H;
$R_4$ is —H or —$CH_3$;
$R_5$ is —H, halogen, or —COOR$_6$; and
$R_6$ is —$CH_3$.

For use in the methods for inhibiting the replication or infectivity of a virus, a more preferred subclass of the compounds of Formula (X) are those wherein:
$R_1$ is —H;
$R_2$ is —$CH_3$;
$R_3$ is —H;
$R_4$ is —H or —$CH_3$; and
$R_5$ is —H.

The invention further provides methods for causing immunosuppression in a patient comprising administering to a patient in need thereof an effective amount of a compound of Formula (X) or a pharmaceutically acceptable salt thereof, wherein, in the compound of Formula (X):
$R_1$ is —H, —$CH_3$, —$CH_2C_6H_5$, —$COCH_3$, —C(O)OC$(CH_3)_3$, or —C(O)$CH_2C_6H_5$;
$R_2$ is a $C_1$–$C_{10}$ straight chain alkyl or —$CH_2C_6H_5$, the —$CH_2C_6H_5$ being unsubstituted or substituted with one or more halo, methoxyl, methyl, methoxycarbonyl, or nitro groups;
$R_3$ is —H, —$CH_3$, —$CH_2C_6H_5$, or —C(O)OC$(CH_3)_3$;
$R_4$ is —H or —$CH_3$;
$R_5$ is —H, —$CH_3$, —$OCH_3$, —F, —Cl, —Br, —I, —CN, —$NH_2$; —NH($C_1$–$C_3$ straight or branched chain alkyl), —NHCOCH$_3$, —NO$_2$, —COOH, —COOR$_6$, —OH, or —OCH$_2$C$_6$H$_5$; and
$R_6$ is a $C_1$–$C_6$ straight chain alkyl.

For use in the methods for causing immunosuppression, a preferred subclass of the compounds of Formula (X) are those wherein:
$R_1$ is —H;
$R_2$ is —$CH_3$ or —$CH_2C_6H_5$;
$R_3$ is —H;
$R_4$ is —H or —$CH_3$;
$R_5$ is —H, halogen, or —COOR$_6$; and
$R_6$ is —$CH_3$.

For use in the methods for causing immunosuppression, a more preferred subclass of the compounds of Formula (X) are those wherein:
$R_1$ is —H;
$R_2$ is —$CH_3$;
$R_3$ is —H;
$R_4$ is —H or —$CH_3$; and
$R_5$ is —H.

The invention further provides methods for treating or preventing an autoimmune disease in a patient comprising administering to a patient in need of such treatment or prevention an effective amount of a compound of Formula (X) or a pharmaceutically acceptable salt thereof, wherein, in the compound of Formula (X):
$R_1$ is —H, —$CH_3$, —$CH_2C_6H_5$, —$COCH_3$, —C(O)OC$(CH_3)_3$, or —C(O)$CH_2C_6H_5$;
$R_2$ is a $C_1$–$C_{10}$ straight chain alkyl or —$CH_2C_6H_5$, the —$CH_2C_6H_5$ being unsubstituted or substituted with one or more halo, methoxyl, methyl, methoxycarbonyl, or nitro groups;
$R_3$ is —H, —$CH_3$, —$CH_2C_6H_5$, or —C(O)OC$(CH_3)_3$;
$R_4$ is —H or —$CH_3$;
$R_5$ is —H, —$CH_3$, —$OCH_3$, —F, —Cl, —Br, —I, —CN, —$NH_2$; —NH($C_1$–$C_3$ straight or branched chain alkyl), —NHCOCH$_3$, —NO$_2$, —COOH, —COOR$_6$, —OH, or —OCH$_2$C$_6$H$_5$; and
$R_6$ is a $C_1$–$C_6$ straight chain alkyl.

For use in the methods for treating or preventing an autoimmune disease, a preferred subclass of the compounds of Formula (X) are those wherein:
$R_1$ is —H;
$R_2$ is —$CH_3$ or —$CH_2C_6H_5$;
$R_3$ is —H;
$R_4$ is —H or —$CH_3$;

$R_5$ is —H, halogen, or —COOR$_6$; and
$R_6$ is —CH$_3$.

For use in the methods for treating or preventing an autoimmune disease, a more preferred subclass of the compounds of Formula (X) are those wherein:
$R_1$ is —H;
$R_2$ is —CH$_3$;
$R_3$ is —H;
$R_4$ is —H or —CH$_3$; and
$R_5$ is —H.

5.11. Formula XI

The present invention encompasses novel compounds having the general Formula (XI) and pharmaceutically acceptable salts thereof, wherein:
$R_1$ is —H, —CH$_3$, —CH$_2$C$_6$H$_5$, —COCH$_3$, —C(O)OC(CH$_3$)$_3$, or —C(O)CH$_2$C$_6$H$_5$;
$R_2$ is a C$_1$–C$_{10}$ straight chain alkyl or —CH$_2$C$_6$H$_5$;
$R_3$ is —H, —CH$_3$, —CH$_2$C$_6$H$_5$, —C(O)OC(CH$_3$)$_3$, or —C(O)CH$_2$C$_6$H$_5$;
$R_4$ is —H or —CH$_3$;
$R_5$ is —H, a C$_1$–C$_{10}$ straight chain alkyl, —OR$_6$, —F, —Cl, —Br, —I, —CN, —COOH, —COOR$_6$, —NH$_2$; —NHCOR$_6$, —NO$_2$, —OH, or —OCH$_2$C$_6$H$_5$; and
$R_6$ is a C$_1$–C$_6$ straight chain alkyl.

The compounds of Formula (XI) or a pharmaceutically acceptable salt thereof are useful for treating or preventing cancer or neoplastic disease in a patient in need of such treatment or prevention. The compounds of Formula (XI) or a pharmaceutically acceptable salt thereof are also useful for inhibiting the growth of a cancer cell or neoplastic cell. The compounds of Formula (XI) or a pharmaceutically acceptable salt thereof are useful for treating or preventing a viral infection in a patient in need of such treatment or prevention. The compounds of Formula (XI) or a pharmaceutically acceptable salt thereof are also useful for inhibiting the replication or infectivity of a virus. The compounds of Formula (XI) or a pharmaceutically acceptable salt thereof are also useful for causing immunosuppression in a patient in need thereof. The compounds of Formula (XI) or a pharmaceutically acceptable salt thereof are also useful for treating an autoimmune disease in a patient in need of such treatment or prevention.

A preferred subclass of the compounds of Formula (XI) is that wherein:
$R_1$ is —H;
$R_2$ is —CH$_3$ or —CH$_2$C$_6$H$_5$;
$R_3$ is —H;
$R_4$ is —H or —CH$_3$;
$R_5$ is —H, —CH$_3$, halogen, or COOR$_6$; and
$R_6$ is —CH$_3$.

A more preferred subclass of the compounds of Formula (XI) is that wherein:
$R_1$ is —H;
$R_2$ is —CH$_3$;
$R_3$ is —H;
$R_4$ is —CH$_3$; and
$R_5$ is —H or Cl.

The present invention also provides compositions comprising a pharmaceutically acceptable carrier and an effective amount of a compound of Formula (XI) or a pharmaceutically acceptable salt thereof, wherein, in the compound of Formula (XI):
$R_1$ is —H, —CH$_3$, —CH$_2$C$_6$H$_5$, —COCH$_3$, —C(O)OC(CH$_3$)$_3$, or —C(O)CH$_2$C$_6$H$_5$;
$R_2$ is a C$_1$–C$_{10}$ straight chain alkyl or —CH$_2$C$_6$H$_5$;
$R_3$ is —H, —CH$_3$, —CH$_2$C$_6$H$_5$, —C(O)OC(CH$_3$)$_3$, or —C(O)CH$_2$C$_6$H$_5$;
$R_4$ is —H or —CH$_3$;
$R_5$ is —H, a C$_1$–C$_{10}$ straight chain alkyl, —OR$_6$, —F, —Cl, —Br, —I, —CN, —COOH, —COOR$_6$, —NH$_2$; —NHCOR$_6$, —NO$_2$, —OH, or —OCH$_2$C$_6$H$_5$; and
$R_6$ is a C$_1$–C$_6$ straight chain alkyl.

The compositions comprising a pharmaceutically acceptable carrier and a compound of Formula (XI) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (XI) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (XI) or a pharmaceutically acceptable salt thereof are also useful for causing immunosuppression in a patient in need thereof. The compositions comprising a pharmaceutically acceptable carrier and a compound of Formula (XI) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (XI) or a pharmaceutically acceptable salt thereof is that wherein, in the compound of Formula (XI):
$R_1$ is —H;
$R_2$ is —CH$_3$ or —CH$_2$C$_6$H$_5$;
$R_3$ is —H;
$R_4$ is —H or —CH$_3$;
$R_5$ is —H, —CH$_3$, halogen, or COOR$_6$; and
$R_6$ is —CH$_3$.

A more preferred subclass of the compositions comprising a pharmaceutically acceptable carrier and a compound of Formula (XI) or a pharmaceutically acceptable salt thereof is that wherein, in the compound of Formula (XI):
$R_1$ is —H;
$R_2$ is —CH$_3$;
$R_3$ is —H;
$R_4$ is —CH$_3$; and
$R_5$ is —H or Cl.

The invention further provides methods for treating or preventing cancer or neoplastic disease in a patient comprising administering to a patient in need of such treatment or prevention an effective amount of a compound of Formula (XI) or a pharmaceutically acceptable salt thereof, wherein, in the compound of Formula (XI):
$R_1$ is —H, —CH$_3$, —CH$_2$C$_6$H$_5$, —COCH$_3$, —C(O)OC(CH$_3$)$_3$, or —C(O)CH$_2$C$_6$H$_5$;
$R_2$ is a C$_1$–C$_{10}$ straight chain alkyl or —CH$_2$C$_6$H$_5$;
$R_3$ is —H, —CH$_3$, —CH$_2$C$_6$H$_5$, —C(O)OC(CH$_3$)$_3$, or —C(O)CH$_2$C$_6$H$_5$;
$R_4$ is —H or —CH$_3$;
$R_5$ is —H, a C$_1$–C$_{10}$ straight chain alkyl, —OR$_6$, —F, —Cl, —Br, —I, —CN, —COOH, —COOR$_6$, —NH$_2$; —NHCOR$_6$, —NO$_2$, —OH, or —OCH$_2$C$_6$H$_5$; and
$R_6$ is a C$_1$–C$_6$ straight chain alkyl.

For use in the methods for treating or preventing cancer or neoplastic disease, a preferred subclass of the compounds of Formula (XI) is that wherein, in the compound of Formula (XI):

$R_1$ is —H;
$R_2$ is —CH$_3$ or —CH$_2$C$_6$H$_5$;
$R_3$ is —H;
$R_4$ is —H or —CH$_3$;
$R_5$ is —H, —CH$_3$, halogen, or COOR$_6$; and
$R_6$ is —CH$_3$.

For use in the methods for treating or preventing cancer or neoplastic disease, a more preferred subclass of the compounds of Formula (XI) is that wherein, in the compound of Formula (XI):
$R_1$ is —H;
$R_2$ is —CH$_3$;
$R_3$ is —H;
$R_4$ is —CH$_3$; and
$R_5$ is —H or Cl.

The invention further provides methods for inhibiting the growth of a cancer cell or neoplastic cell comprising a contacting a cancer cell or neoplastic cell with an effective amount of a compound having the general Formula (XI) or a pharmaceutically acceptable salt thereof, wherein, in the compound of Formula (XI):
$R_1$ is —H, —CH$_3$, —CH$_2$C$_6$H$_5$, —COCH$_3$, —C(O)OC(CH$_3$)$_3$, or —C(O)CH$_2$C$_6$H$_5$;
$R_2$ is a C$_1$–C$_{10}$ straight chain alkyl or —CH$_2$C$_6$H$_5$;
$R_3$ is —H, —CH$_3$, —CH$_2$C$_6$H$_5$, —C(O)OC(CH$_3$)$_3$, or —C(O)CH$_2$C$_6$H$_5$;
$R_4$ is —H or —CH$_3$;
$R_5$ is —H, a C$_1$–C$_{10}$ straight chain alkyl, —OR$_6$, —F, —Cl, —Br, —I, —CN, —COOH, —COOR$_6$, —NH$_2$; —NHCOR$_6$, —NO$_2$, —OH, or —OCH$_2$C$_6$H$_5$; and
$R_6$ is a C$_1$–C$_6$ straight chain alkyl.

For use in the methods for inhibiting the growth of a cancer or neoplastic cell, a preferred subclass of the compounds of Formula (XI) is that wherein, in the compound of Formula (XI):
$R_1$ is —H;
$R_2$ is —CH$_3$ or —CH$_2$C$_6$H$_5$;
$R_3$ is —H;
$R_4$ is —H or —CH$_3$;
$R_5$ is —H, —CH$_3$, halogen, or COOR$_6$; and
$R_6$ is —CH$_3$.

For use in the methods for inhibiting the growth of a cancer or neoplastic cell, a more preferred subclass of the compounds of Formula (XI) is that wherein, in the compound of Formula (XI):
$R_1$ is —H;
$R_2$ is —CH$_3$;
$R_3$ is —H;
$R_4$ is —CH$_3$; and
$R_5$ is —H or Cl.

The invention further provides methods for treating or preventing a viral infection in a patient comprising administering to a patient in need of such treatment or prevention an effective amount of a compound of Formula (XI) or a pharmaceutically acceptable salt thereof, wherein, in the compound of Formula (XI):
$R_1$ is —H, —CH$_3$, —CH$_2$C$_6$H$_5$, —COCH$_3$, —C(O)OC(CH$_3$)$_3$, or —C(O)CH$_2$C$_6$H$_5$;
$R_2$ is a C$_1$–C$_{10}$ straight chain alkyl or —CH$_2$C$_6$H$_5$;
$R_3$ is —H, —CH$_3$, —CH$_2$C$_6$H$_5$, —C(O)OC(CH$_3$)$_3$, or —C(O)CH$_2$C$_6$H$_5$;
$R_4$ is —H or —CH$_3$;
$R_5$ is —H, a C$_1$–C$_{10}$ straight chain alkyl, —OR$_6$, —F, —Cl, —Br, —I, —CN, —COOH, —COOR$_6$, —NH$_2$; —NHCOR$_6$, —NO$_2$, —OH, or —OCH$_2$C$_6$H$_5$; and
$R_6$ is a C$_1$–C$_6$ straight chain alkyl.

For use in the present methods for treating or preventing a viral infection, a preferred subclass of the compounds of Formula (XI) is that wherein, in the compound of Formula (XI):
$R_1$ is —H;
$R_2$ is —CH$_3$ or —CH$_2$C$_6$H$_5$;
$R_3$ is —H;
$R_4$ is —H or —CH$_3$;
$R_5$ is —H, —CH$_3$, halogen, or COOR$_6$; and
$R_6$ is —CH$_3$.

For use in the present methods for treating or preventing a viral infection, a more preferred subclass of the compounds of Formula (XI) is that wherein, in the compound of Formula (XI):
$R_1$ is —H;
$R_2$ is —CH$_3$;
$R_3$ is —H;
$R_4$ is —CH$_3$; and
$R_5$ is —H or Cl.

The invention further provides methods for inhibiting the replication or infectivity of a virus comprising a contacting a virus or a virus-infected cell with an effective amount of a compound having the general Formula (XI) or a pharmaceutically acceptable salt thereof, wherein, in the compound of Formula (XI):
$R_1$ is —H, —CH$_3$, —CH$_2$C$_6$H$_5$, —COCH$_3$, —C(O)OC(CH$_3$)$_3$, or —C(O)CH$_2$C$_6$H$_5$;
$R_2$ is a C$_1$–C$_{10}$ straight chain alkyl or —CH$_2$C$_6$H$_5$;
$R_3$ is —H, —CH$_3$, —CH$_2$C$_6$H$_5$, —C(O)OC(CH$_3$)$_3$, or —C(O)CH$_2$C$_6$H$_5$;
$R_4$ is —H or —CH$_3$;
$R_5$ is —H, a C$_1$–C$_{10}$ straight chain alkyl, —OR$_6$, —F, —Cl, —Br, —I, —CN, —COOH, —COOR$_6$, —NH$_2$; —NHCOR$_6$, —NO$_2$, —OH, or —OCH$_2$C$_6$H$_5$; and
$R_6$ is a C$_1$–C$_6$ straight chain alkyl.

For use in the methods for inhibiting the replication or infectivity of a virus, a preferred subclass of the compounds of Formula (XI) are those wherein:
$R_1$ is —H;
$R_2$ is —CH$_3$ or —CH$_2$C$_6$H$_5$;
$R_3$ is —H;
$R_4$ is —H or —CH$_3$;
$R_5$ is —H, —CH$_3$, halogen, or COOR$_6$; and
$R_6$ is —CH$_3$.

For use in the methods for inhibiting the replication or infectivity of a virus, a more preferred subclass of the compounds of Formula (XI) are those wherein:
$R_1$ is —H;
$R_2$ is —CH$_3$;
$R_3$ is —H;
$R_4$ is —CH$_3$; and
$R_5$ is —H or Cl.

The invention further provides methods for causing immunosuppression in a patient comprising administering to a patient in need thereof an effective amount of a compound of Formula (XI) or a pharmaceutically acceptable salt thereof, wherein, in the compound of Formula (XI):
$R_1$ is —H, —CH$_3$, —CH$_2$C$_6$H$_5$, —COCH$_3$, —C(O)OC(CH$_3$)$_3$, or —C(O)CH$_2$C$_6$H$_5$;
$R_2$ is a C$_1$–C$_{10}$ straight chain alkyl or —CH$_2$C$_6$H$_5$;
$R_3$ is —H, —CH$_3$, —CH$_2$C$_6$H$_5$, —C(O)OC(CH$_3$)$_3$, or —C(O)CH$_2$C$_6$H$_5$;
$R_4$ is —H or —CH$_3$;
$R_5$ is —H, a C$_1$–C$_{10}$ straight chain alkyl, —OR$_6$, —F, —Cl, —Br, —I, —CN, —COOH, —COOR$_6$, —NH$_2$; —NHCOR$_6$, —NO$_2$, —OH, or —OCH$_2$C$_6$H$_5$; and
$R_6$ is a C$_1$–C$_6$ straight chain alkyl.

For use in the methods for causing immunosuppression, a preferred subclass of the compounds of Formula (XI) are those wherein:
$R_1$ is —H;
$R_2$ is —$CH_3$ or —$CH_2C_6H_5$;
$R_3$ is —H;
$R_4$ is —H or —$CH_3$;
$R_5$ is —H, —$CH_3$, halogen, or $COOR_6$; and
$R_6$ is —$CH_3$.

For use in the methods for causing immunosuppression, a more preferred subclass of the compounds of Formula (XI) are those wherein:
$R_1$ is —H;
$R_2$ is —$CH_3$;
$R_3$ is —H;
$R_4$ is —$CH_3$; and
$R_5$ is —H or Cl.

The invention further provides methods for treating or preventing an autoimmune disease in a patient comprising administering to a patient in need of such treatment or prevention an effective amount of a compound of Formula (XI) or a pharmaceutically acceptable salt thereof, wherein, in the compound of Formula (XI):
$R_1$ is —H, —$CH_3$, —$CH_2C_6H_5$, —$COCH_3$, —$C(O)OC(CH_3)_3$, or —$C(O)CH_2C_6H_5$;
$R_2$ is a $C_1$–$C_{10}$ straight chain alkyl or —$CH_2C_6H_5$;
$R_3$ is —H, —$CH_3$, —$CH_2C_6H_5$, —$C(O)OC(CH_3)_3$, or —$C(O)CH_2C_6H_5$;
$R_4$ is —H or —$CH_3$;
$R_5$ is —H, a $C_1$–$C_{10}$ straight chain alkyl, —$OR_6$, —F, —Cl, —Br, —I, —CN, —COOH, —$COOR_6$, —$NH_2$, —$NHCOR_6$, —$NO_2$, —OH, or —$OCH_2C_6H_5$; and
$R_6$ is a $C_1$–$C_6$ straight chain alkyl.

For use in the methods for treating or preventing an autoimmune disease, a preferred subclass of the compounds of Formula (XI) are those wherein:
$R_1$ is —H;
$R_2$ is —$CH_3$ or —$CH_2C_6H_5$;
$R_3$ is —H;
$R_4$ is —H or —$CH_3$;
$R_5$ is —H, —$CH_3$, halogen, or $COOR_6$; and
$R_6$ is —$CH_3$.

For use in the methods for treating or preventing an autoimmune disease, a more preferred subclass of the compounds of Formula (XI) are those wherein:
$R_1$ is —H;
$R_2$ is —$CH_3$;
$R_3$ is —H;
$R_4$ is —$CH_3$; and
$R_5$ is —H or Cl.

5.12. Formula XII

The present invention encompasses novel compounds having the general Formula (XII) or a pharmaceutically acceptable salt thereof, wherein:
$R_1$ is —H, —$CH_3$, —$CH_2C_6H_5$, or —$C(O)OC(CH_3)_3$;
$R_2$ is a $C_1$–$C_{10}$ straight chain alkyl or —$CH_2C_6H_5$;
$R_3$ is —H, —$SO_2CH_3$, —$SO_2C_6H_5$, —$C(O)OC(CH_3)_3$, —$COCH_3$, —$CO(CH_2)_4CH_3$, —$CO(CH_2)_8CH_3$, —$COC_6H_5$, —CO-4-($NHCOC_6H_5$)$C_6H_4$, —CO-2-pyridyl, —CO-2-napthyl, —CO-2-quinolyl, —CO-6-($NHCO(CH_2)_4CH_3$)-2-quinolyl, —CO-2-pyrrolyl, -2-CO-2-indolyl, —CO-1-methyl-2-indolyl, —CO-2-benzofuranyl, —CO-2-benzothiophenyl, —CO-3-methyl-2-indenyl, or —CO—$R_4$-2-indolyl; and $R_4$ is -5-$OCH_3$, -6-OH-7-$OCH_3$, -5-$NHCONH_2$, 5-$NHCOC_6H_5$, -5-NHCO-indolyl, -5-NHCO-2-benzofuranyl, -5-NHCO-5($NHCONH_2$)-2-indolyl, or -5-NHCO-5-($NHCOC_6H_5$)-2-indolyl.

The compounds of Formula (XII) or a pharmaceutically acceptable salt thereof are useful for treating or preventing cancer or neoplastic disease in a patient in need of such treatment or prevention. The compounds of Formula (XII) or a pharmaceutically acceptable salt thereof are also useful for inhibiting the growth of a cancer cell or neoplastic cell. The compounds of Formula (XII) or a pharmaceutically acceptable salt thereof are useful for treating or preventing a viral infection in a patient in need of such treatment or prevention. The compounds of Formula (XII) or a pharmaceutically acceptable salt thereof are also useful for inhibiting the replication or infectivity of a virus. The compounds of Formula (XII) or a pharmaceutically acceptable salt thereof are also useful for causing immunosuppression in a patient in need thereof. The compounds of Formula (XII) or a pharmaceutically acceptable salt thereof are also useful for treating an autoimmune disease in a patient in need of such treatment or prevention.

A preferred subclass of the compounds of Formula (XII) is that wherein:
$R_1$ is —H;
$R_2$ is —$CH_3$ or —$CH_2C_6H_5$;
$R_3$ is —H, —$COCH_3$, —CO-2-quinolyl, —CO-6-($NHCO(CH_2)_4CH_3$)-2-quinolyl, -2—CO-2-indolyl, or —CO—$R_4$-2-indolyl; and
$R_4$ is -5-NHCO-indolyl, -5-NHCO-2-benzofuranyl, or -5-NHCO-5($NHCONH_2$)-2-indolyl.

A more preferred subclass of the compounds of Formula (XII) is that wherein:
$R_1$ is —H;
$R_2$ is —$CH_3$;
$R_3$ is —H, —$COCH_3$, or —CO—$R_4$-2-indolyl; and
$R_4$ is -5-NHCO-indolyl.

The present invention also provides compositions comprising a pharmaceutically acceptable carrier and an effective amount of a compound of Formula (XII) or a pharmaceutically acceptable salt thereof, wherein, in the compound of Formula (XII):
$R_1$ is —H, —$CH_3$, —$CH_2C_6H_5$, or —$C(O)OC(CH_3)_3$;
$R_2$ is a $C_1$–$C_{10}$ straight chain alkyl or —$CH_2C_6H_5$;
$R_3$ is —H, —$SO_2CH_3$, —$SO_2C_6H_5$, —$C(O)OC(CH_3)_3$, —$COCH_3$, —$CO(CH_2)_4CH_3$, —$CO(CH_2)_8CH_3$, —$COC_6H_5$, —CO-4-($NHCOC_6H_5$)$C_6H_4$, —CO-2-pyridyl, —CO-2-napthyl, —CO-2-quinolyl, —CO-6-($NHCO(CH_2)_4CH_3$)-2-quinolyl, —CO-2-pyrrolyl, -2-CO-2-indolyl, —CO-1-methyl-2-indolyl, —CO-2-benzofuranyl, —CO-2-benzothiophenyl, —CO-3-methyl-2-indenyl, or —CO—$R_4$-2-indolyl; and $R_4$ is -5-$OCH_3$, -6-OH-7-$OCH_3$, -5-$NHCONH_2$, 5-$NHCOC_6H_5$, -5-NHCO-indolyl, -5-NHCO-2-benzofuranyl, -5-NHCO-5-($NHCONH_2$)-2-indolyl, or -5-NHCO-5-($NHCOC_6H_5$)-2-indolyl.

The compositions comprising a pharmaceutically acceptable carrier and a compound of Formula (XII) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (XII) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (XII) or a pharmaceutically acceptable salt thereof are also useful for causing immunosuppression in a patient in need thereof. The compositions comprising a pharmaceutically acceptable carrier and a compound of Formula (XII) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (XII) or a pharmaceutically acceptable salt thereof is that wherein, in the compound of Formula (XII):

$R_1$ is —H;
$R_2$ is —$CH_3$ or —$CH_2C_6H_5$;
$R_3$ is —H, —$COCH_3$, —CO-2-quinolyl, —CO-6-(NHCO($CH_2)_4CH_3$)-2-quinolyl, -2-CO-2-indolyl, or —CO—$R_4$-2-indolyl; and
$R_4$ is -5-NHCO-indolyl, -5-NHCO-2-benzofuranyl, or -5-NHCO-5($NHCONH_2$)-2-indolyl.

A more preferred subclass of the compositions comprising a pharmaceutically acceptable carrier and a compound of Formula (XII) or a pharmaceutically acceptable salt thereof is that wherein, in the compound of Formula (XII):

$R_1$ is —H;
$R_2$ is —$CH_3$;
$R_3$ is —H, —$COCH_3$, or —CO—$R_4$-2-indolyl; and;
$R_4$ is -5-NHCO-indolyl.

The invention further provides methods for treating or preventing cancer or neoplastic disease in a patient comprising administering to a patient in need of such treatment or prevention an effective amount of a compound of Formula (XII) or a pharmaceutically acceptable salt thereof, wherein, in the compound of Formula (XII):

$R_1$ is —H, —$CH_3$, —$CH_2C_6H_5$, or —$C(O)OC(CH_3)_3$;
$R_2$ is a $C_1$–$C_{10}$ straight chain alkyl or —$CH_2C_6H_5$;
$R_3$ is —H, —$SO_2CH_3$, —$SO_2C_6H_5$, —$C(O)OC(CH_3)_3$, —$COCH_3$, —$CO(CH_2)_4CH_3$, —$CO(CH_2)_8CH_3$, —$COC_6H_5$, —CO-4-($NHCOC_6H_5$)$C_6H_4$, —CO-2-pyridyl, —CO-2-napthyl, —CO-2-quinolyl, —CO-6-(NHCO($CH_2)_4$$CH_3$)-2-quinolyl, —CO-2-pyrrolyl, -2-CO-2-indolyl, —CO-1-methyl-2-indolyl, —CO-2-benzofuranyl, —CO-2-benzothiophenyl, —CO-3-methyl-2-indenyl, or —CO—$R_4$-2-indolyl; and
$R_4$ is -5-$OCH_3$, -6-OH-7-$OCH_3$, -5-$NHCONH_2$, 5-$NHCOC_6H_5$, -5-NHCO-indolyl, -5-NHCO-2-benzofuranyl, -5-NHCO-5($NHCONH_2$)-2-indolyl, or -5-NHCO-5-($NHCOC_6H_5$)-2-indolyl.

For use in the methods for treating or preventing cancer or neoplastic disease, a preferred subclass of the compounds of Formula (XII) is that wherein, in the compound of Formula (XII):

$R_1$ is —H;
$R_2$ is —$CH_3$ or —$CH_2C_6H_5$;
$R_3$ is —H, —$COCH_3$, —CO-2-quinolyl, —CO-6-(NHCO($CH_2)_4CH_3$)-2-quinolyl, -2-CO-2-indolyl, or —CO—$R_4$-2-indolyl; and
$R_4$ is -5-NHCO-indolyl, -5-NHCO-2-benzofuranyl, or -5-NHCO-5($NHCONH_2$)-2-indolyl.

For use in the methods for treating or preventing cancer or neoplastic disease, a more preferred subclass of the compounds of Formula (XII) is that wherein, in the compound of Formula (XII):

$R_1$ is —H;
$R_2$ is —$CH_3$;
$R_3$ is —H, —$COCH_3$, or —CO—$R_4$-2-indolyl; and;
$R_4$ is -5-NHCO-indolyl.

The invention further provides methods for inhibiting the growth of a cancer cell or neoplastic cell comprising contacting a cancer cell or neoplastic cell with an effective amount of a compound having the general Formula (XII) or a pharmaceutically acceptable salt thereof, wherein, in the compound of Formula (XII):

$R_1$ is —H, —$CH_3$, —$CH_2C_6H_5$, or —$C(O)OC(CH_3)_3$;
$R_2$ is a $C_1$–$C_{10}$ straight chain alkyl or —$CH_2C_6H_5$;
$R_3$ is —H, —$SO_2CH_3$, —$SO_2C_6H_5$, —$C(O)OC(CH_3)_3$, —$COCH_3$, —$CO(CH_2)_4CH_3$, —$CO(CH_2)_8CH_3$, —$COC_6H_5$, —CO-4-($NHCOC_6H_5$)$C_6H_4$, —CO-2-pyridyl, —CO-2-napthyl, —CO-2-quinolyl, —CO-6-(NHCO($CH_2)_4$$CH_3$)-2-quinolyl, —CO-2-pyrrolyl, -2-CO-2-indolyl, —CO-1-methyl-2-indolyl, —CO-2-benzofuranyl, —CO-2-benzothiophenyl, —CO-3-methyl-2-indenyl, or —CO—$R_4$-2-indolyl; and
$R_4$ is -5-$OCH_3$, -6-OH-7-$OCH_3$, -5-$NHCONH_2$, 5-$NHCOC_6H_5$, -5-NHCO-indolyl, -5-NHCO-2-benzofuranyl,-5-NHCO-5($NHCONH_2$)-2-indolyl, or -5-NHCO-5-($NHCOC_6H_5$)-2-indolyl.

For use in the methods for inhibiting the growth of a cancer or neoplastic cell, a preferred subclass of the compounds of Formula (XII) is that wherein, in the compound of Formula (XII):

$R_1$ is —H;
$R_2$ is —$CH_3$ or —$CH_2C_6H_5$;
$R_3$ is —H, —$COCH_3$, —CO-2-quinolyl, —CO-6-(NHCO($CH_2$ $_4CH_3$)-2-quinolyl, -2-CO-2-indolyl, or —CO—$R_4$-2-indolyl; and
$R_4$ is -5-NHCO-indolyl, -5-NHCO-2-benzofuranyl, or -5-NHCO-5($NHCONH_2$)-2-indolyl.

For use in the methods for inhibiting the growth of a cancer or neoplastic cell, a more preferred subclass of the compounds of Formula (XII) is that wherein, in the compound of Formula (XII):

$R_1$ is —H;
$R_2$ is —$CH_3$;
$R_3$ is —H, —$COCH_3$, or —CO—$R_4$-2-indolyl; and;
$R_4$ is -5-NHCO-indolyl.

The invention further provides methods for treating or preventing a viral infection in a patient comprising administering to a patient in need of such treatment or prevention an effective amount of a compound of Formula (XII) or a pharmaceutically acceptable salt thereof, wherein, in the compound of Formula (XII):

$R_1$ is —H, —$CH_3$, —$CH_2C_6H_5$, or —$C(O)OC(CH_3)_3$;
$R_2$ is a $C_1$–$C_{10}$ straight chain alkyl or —$CH_2C_6H_5$;
$R_3$ is —H, —$SO_2CH_3$, —$SO_2C_6H_5$, —$C(O)OC(CH_3)_3$, —$COCH_3$, —$CO(CH_2)_4CH_3$, —$CO(CH_2)_8CH_3$, —$COC_6H_5$, —CO-4-($NHCOC_6H_5$)$C_6H_4$, —CO-2-pyridyl, —CO-2-napthyl, —CO-2-quinolyl, —CO-6-(NHCO($CH_2)_4$$CH_3$)-2-quinolyl, —CO-2-pyrrolyl, -2-CO-2-indolyl, —CO-1-methyl-2-indolyl, —CO-2-benzofuranyl, —CO-2-benzothiophenyl, —CO-3-methyl-2-indenyl, or —CO—$R_4$-2-indolyl; and
$R_4$ is -5-$OCH_3$, -6-OH-7-$OCH_3$, -5-$NHCONH_2$, 5-$NHCOC_6H_5$, -5-NHCO-indolyl, -5-NHCO-2-benzofuranyl, -5-NHCO-5($NHCONH_2$)-2-indolyl, or -5-NHCO-5-($NHCOC_6H_5$)-2-indolyl.

For use in the present methods for treating or preventing a viral infection, a preferred subclass of the compounds of Formula (XII) is that wherein, in the compound of Formula (XII):

$R_1$ is —H;
$R_2$ is —$CH_3$ or —$CH_2C_6H_5$;

$R_3$ is —H, —COCH$_3$, —CO-2-quinolyl, —CO-6-(NHCO(CH$_2$ $_4$CH$_3$)-2-quinolyl, -2-CO-2-indolyl, or —CO—R$_4$-2-indolyl; and $R_4$ is -5-NHCO-indolyl, -5-NHCO-2-benzofuranyl, or -5-NHCO-5(NHCONH$_2$)-2-indolyl.

For use in the present methods for treating or preventing a viral infection, a more preferred subclass of the compounds of Formula (XII) is that wherein, in the compound of Formula (XIII):

$R_1$ is —H;
$R_2$ is —CH$_3$;
$R_3$ is —H, —COCH$_3$, or —CO—R$_4$-2-indolyl; and;
$R_4$ is -5-NHCO-indolyl.

The invention further provides methods for inhibiting the replication or infectivity of a virus comprising contacting a virus or a virus-infected cell with an effective amount of a compound having the general Formula (XII) or a pharmaceutically acceptable salt thereof, wherein, in the compound of Formula (XII):

$R_1$ is —H, —CH$_3$, —CH$_2$C$_6$H$_5$, or —C(O)OC(CH$_3$)$_3$;
$R_2$ is a C$_1$–C$_{10}$ straight chain alkyl or —CH$_2$C$_6$H$_5$;
$R_3$ is —H, —SO$_2$CH$_3$, —SO$_2$C$_6$H$_5$, —C(O)OC(CH$_3$)$_3$, —COCH$_3$, —CO(CH$_2$)$_4$CH$_3$, —CO(CH$_2$)$_8$CH$_3$, —COC$_6$H$_5$, —CO-4-(NHCOC$_6$H$_5$)C$_6$H$_4$, —CO-2-pyridyl, —CO-2-napthyl, —CO-2-quinolyl, —CO-6-(NHCO(CH$_2$)$_4$CH$_3$)-2-quinolyl, —CO-2-pyrrolyl, -2-CO-2-indolyl, —CO-1-methyl-2-indolyl, —CO-2-benzofuranyl, —CO-2-benzothiophenyl, —CO-3-methyl-2-indenyl, or —CO—R$_4$-2-indolyl; and $R_4$ is -5-OCH$_3$, -6-OH-7-OCH$_3$, -5-NHCONH$_2$, 5-NHCOC$_6$H$_5$, -5-NHCO-indolyl, -5-NHCO-2-benzofuranyl, -5-NHCO-5(NHCONH$_2$)-2-indolyl, or -5-NHCO-5-(NHCOC$_6$H$_5$)-2-indolyl.

For use in the methods for inhibiting the replication or infectivity of a virus, a preferred subclass of the compounds of Formula (XII) are those wherein:

$R_1$ is —H;
$R_2$ is —CH$_3$ or —CH$_2$C$_6$H$_5$;
$R_3$ is —H, —COCH$_3$, —CO-2-quinolyl, —CO-6-(NHCO(CH$_2$ $_4$CH$_3$)-2-quinolyl, -2-CO-2-indolyl, or —CO—R$_4$-2-indolyl; and $R_4$ is -5-NHCO-indolyl, -5-NHCO-2-benzofuranyl, or -5-NHCO-5(NHCONH$_2$)-2-indolyl.

For use in the methods for inhibiting the replication or infectivity of a virus, a more preferred subclass of the compounds of Formula (XII) are those wherein:

$R_1$ is —H;
$R_2$ is —CH$_3$;
$R_3$ is —H, —COCH$_3$, or —CO—R$_4$-2-indolyl; and
$R_4$ is -5-NHCO-indolyl.

The invention further provides methods for causing immunosuppression in a patient comprising administering to a patient in need thereof an effective amount of a compound of Formula (XII) or a pharmaceutically acceptable salt thereof, wherein, in the compound of Formula (XII):

$R_1$ is —H, —CH$_3$, —CH$_2$C$_6$H$_5$, or —C(O)OC(CH$_3$)$_3$;
$R_2$ is a C$_1$–C$_{10}$ straight chain alkyl or —CH$_2$C$_6$H$_5$;
$R_3$ is —H, —SO$_2$CH$_3$, —SO$_2$C$_6$H$_5$, —C(O)OC(CH$_3$)$_3$, —COCH$_3$, —CO(CH$_2$)$_4$CH$_3$, —CO(CH$_2$)$_8$CH$_3$, —COC$_6$H$_5$, —CO-4-(NHCOC$_6$H$_5$)C$_6$H$_4$, —CO-2-pyridyl, —CO-2-napthyl, —CO-2-quinolyl, —CO-6-(NHCO(CH$_2$)$_4$CH$_3$)-2-quinolyl, —CO-2-pyrrolyl, -2-CO-2-indolyl, —CO-1-methyl-2-indolyl, —CO-2-benzofuranyl, —CO-2-benzothiophenyl, —CO-3-methyl-2-indenyl, or —CO—R$_4$-2-indolyl; and $R_4$ is -5-OCH$_3$, -6-OH-7-OCH$_3$, -5-NHCONH$_2$, 5-NHCOC$_6$H$_5$, -5-NHCO-indolyl, -5-NHCO-2-benzofuranyl, -5-NHCO-5(NHCONH$_2$)-2-indolyl, or -5-NHCO-5-(NHCOC$_6$H$_5$)-2-indolyl.

For use in the methods for causing immunosuppression, a preferred subclass of the compounds of Formula (XII) are those wherein:

$R_1$ is —H;
$R_2$ is —CH$_3$ or —CH$_2$C$_6$H$_5$;
$R_3$ is —H, —COCH$_3$, —CO-2-quinolyl, —CO-6-(NHCO(CH$_2$ $_4$CH$_3$)-2-quinolyl, -2-CO-2-indolyl, or —CO—R$_4$-2-indolyl; and $R_4$ is -5-NHCO-indolyl, -5-NHCO-2-benzofuranyl, or -5-NHCO-5(NHCONH$_2$)-2-indolyl.

For use in the methods for causing immunosuppression, a more preferred subclass of the compounds of Formula (XII) are those wherein:

$R_1$ is —H;
$R_2$ is —CH$_3$;
$R_3$ is —H, —COCH$_3$, or —CO—R$_4$-2-indolyl; and;
$R_4$ is -5-NHCO-indolyl.

The invention further provides methods for treating or preventing an autoimmune disease in a patient comprising administering to a patient in need of such treatment or prevention an effective amount of a compound of Formula (XII) or a pharmaceutically acceptable salt thereof, wherein, in the compound of Formula (XII):

$R_1$ is —H, —CH$_3$, —CH$_2$C$_6$H$_5$, or —C(O)OC(CH$_3$)$_3$;
$R_2$ is a C$_1$–C$_{10}$ straight chain alkyl or —CH$_2$C$_6$H$_5$;
$R_3$ is —H, —SO$_2$CH$_3$, —SO$_2$C$_6$H$_5$, —C(O)OC(CH$_3$)$_3$, —COCH$_3$, —CO(CH$_2$)$_4$CH$_3$, —CO(CH$_2$)$_8$CH$_3$, —COC$_6$H$_5$, —CO-4-(NHCOC$_6$H$_5$)C$_6$H$_4$, —CO-2-pyridyl, —CO-2-napthyl, —CO-2-quinolyl, —CO-6-(NHCO(CH$_2$)$_4$CH$_3$)-2-quinolyl, —CO-2-pyrrolyl, -2-CO-2-indolyl, —CO-1-methyl-2-indolyl, —CO-2-benzofuranyl, —CO-2-benzothiophenyl, —CO-3-methyl-2-indenyl, or —CO—R$_4$-2-indolyl; and $R_4$ is -5-OCH$_3$, -6-OH-7-OCH$_3$, -5-NHCONH$_2$, 5-NHCOC$_6$H$_5$, -5-NHCO-indolyl, -5-NHCO-2-benzofuranyl, -5-NHCO-5(NHCONH$_2$)-2-indolyl, or -5-NHCO-5-(NHCOC$_6$H$_5$)-2-indolyl.

For use in the methods for treating or preventing an autoimmune disease, a preferred subclass of the compounds of Formula (XII) are those wherein:

$R_1$ is —H;
$R_2$ is —CH$_3$ or —CH$_2$C$_6$H$_5$;
$R_3$ is —H, —COCH$_3$, —CO-2-quinolyl, —CO-6-(NHCO(CH$_2$ $_4$CH$_3$)-2-quinolyl, -2-CO-2-indolyl, or —CO—R$_4$-2-indolyl; and $R_4$ is -5-NHCO-indolyl, -5-NHCO-2-benzofuranyl, or -5-NHCO-5(NHCONH$_2$)-2-indolyl.

For use in the methods treating or preventing an autoimmune disease, a more preferred subclass of the compounds of Formula (XII) are those wherein:

$R_1$ is —H;
$R_2$ is —CH$_3$;
$R_3$ is —H, —COCH$_3$, or —CO—R$_4$-2-indolyl; and
$R_4$ is -5-NHCO-indolyl.

5.13. Formula XIII

The present invention encompasses novel compounds having the general Formula (XIII) or a pharmaceutically acceptable salt thereof, wherein:

each $R_1$ is independently selected from the group consisting of —H, —CH$_3$, —CH$_2$C$_6$H$_5$, —C(O)OC(CH$_3$)$_3$, or —C(O)OCH$_2$C$_6$H$_5$;

$R_2$ is —H or a $C_1$–$C_{10}$ straight chain alkyl; and n is 1 to 4.

The compounds of Formula (XIII) or a pharmaceutically acceptable salt thereof are useful for treating or preventing cancer or neoplastic disease in a patient in need of such treatment or prevention. The compounds of Formula (XIII) or a pharmaceutically acceptable salt thereof are also useful for inhibiting the growth of a cancer cell or neoplastic cell. The compounds of Formula (XIII) or a pharmaceutically acceptable salt thereof are useful for treating or preventing a viral infection in a patient in need of such treatment or prevention. The compounds of Formula (XIII) or a pharmaceutically acceptable salt thereof are also useful for inhibiting the replication or infectivity of a virus. The compounds of Formula (XIII) or a pharmaceutically acceptable salt thereof are also useful for causing immunosuppression in a patient in need thereof. The compounds of Formula (XII) or a pharmaceutically acceptable salt thereof are also useful for treating an autoimmune disease in a patient in need of such treatment or prevention.

A preferred subclass of the compounds of Formula (XIII) is that wherein:

$R_1$ is —H;

$R_2$ is —H or —CH$_3$; and n is 1 to 4.

A more preferred subclass of the compounds of Formula (XIII) is that wherein:

$R_1$ is —H;

$R_2$ is —H or —CH$_3$; and n is 2.

The present invention also provides compositions comprising a pharmaceutically acceptable carrier and an effective amount of a compound of Formula (XIII) or a pharmaceutically acceptable salt thereof, wherein, in the compound of Formula (XIII):

each $R_1$ is independently selected from the group consisting of —H, —CH$_3$, —CH$_2$C$_6$H$_5$, —C(O)OC(CH$_3$)$_3$, or —C(O)OCH$_2$C$_6$H$_5$;

$R_2$ is —H or a $C_1$–$C_{10}$ straight chain alkyl; and n is 1 to 4.

The compositions comprising a pharmaceutically acceptable carrier and a compound of Formula (XIII) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (XIII) or a pharmaceutically acceptable salt thereof are useful for treating or preventing a viral infection in a patient in need of such treatment or prevention. These compositions are also useful for inhibiting the replication or infectivity of a virus. The compositions comprising a pharmaceutically acceptable carrier and a compound of Formula (XIII) or a pharmaceutically acceptable salt thereof are also useful for causing immunosuppression in a patient in need thereof. The compositions comprising a pharmaceutically acceptable carrier and a compound of Formula (XIII) or a pharmaceutically acceptable salt thereof are also useful for treating an autoimmune disease in a patient in need of such treatment or prevention.

A preferred subclass of the compositions comprising a pharmaceutically acceptable carrier and a compound of Formula (XIII) or a pharmaceutically acceptable salt thereof is that wherein, in the compound of Formula (XIII):

$R_1$ is —H;

$R_2$ is —H or —CH$_3$; and n is 1 to 4.

A more preferred subclass of the compositions comprising a pharmaceutically acceptable carrier and a compound of Formula (XIII) or a pharmaceutically acceptable salt thereof is that wherein, in the compound of Formula (XIII):

$R_1$ is —H;

$R_2$ is —H or —CH$_3$; and n is 2.

The invention further provides methods for treating or preventing cancer or neoplastic disease in a patient comprising administering to a patient in need of such treatment or prevention an effective amount of a compound of Formula (XIII) or a pharmaceutically acceptable salt thereof, wherein, in the compound of Formula (XIII):

each $R_1$ is independently selected from the group consisting of —H, —CH$_3$, —CH$_2$C$_6$H$_5$, —C(O)OC(CH$_3$)$_3$, or —C(O)OCH$_2$C$_6$H$_5$;

$R_2$ is —H or a $C_1$–$C_{10}$ straight chain alkyl; and n is 1 to 4.

For use in the methods for treating or preventing cancer or neoplastic disease, a preferred subclass of the compounds of Formula (XIII) is that wherein, in the compound of Formula (XIII):

$R_1$ is —H;

$R_2$ is —H or —CH$_3$; and n is 1 to 4.

For use in the methods for treating or preventing cancer or neoplastic disease, a more preferred subclass of the compounds of Formula (XIII) is that wherein, in the compound of Formula (XIII):

$R_1$ is —H;

$R_2$ is —H or —CH$_3$; and n is 2.

The invention further provides methods for inhibiting the growth of a cancer cell or neoplastic cell comprising contacting a cancer cell or neoplastic cell with an effective amount of a compound having the general Formula (XIII) or a pharmaceutically acceptable salt thereof, wherein, in the compound of Formula (XIII):

each $R_1$ is independently selected from the group consisting of —H, —CH$_3$, —CH$_2$C$_6$H$_5$, —C(O)OC(CH$_3$)$_3$, or —C(O)OCH$_2$C$_6$H$_5$;

$R_2$ is —H or a $C_1$–$C_{10}$ straight chain alkyl; and n is 1 to 4.

For use in the methods for inhibiting the growth of a cancer or neoplastic cell, a preferred subclass of the compounds of Formula (XIII) is that wherein, in the compound of Formula (XIII):

$R_1$ is —H;

$R_2$ is —H or —CH$_3$; and n is 1 to 4.

For use in the methods for inhibiting the growth of a cancer or neoplastic cell, a more preferred subclass of the compounds of Formula (XIII) is that wherein, in the compound of Formula (XIII):

$R_1$ is —H;

$R_2$ is —H or —CH$_3$; and n is 2.

The invention further provides methods for treating or preventing a viral infection in a patient comprising administering to a patient in need of such treatment or prevention an effective amount of a compound of Formula (XIII) or a pharmaceutically acceptable salt thereof, wherein, in the compound of Formula (XIII):

each $R_1$ is independently selected from the group consisting of —H, —$CH_3$, —$CH_2C_6H_5$, —$C(O)OC(CH_3)_3$, or —$C(O)OCH_2C_6H_5$;

$R_2$ is —H or a $C_1$–$C_{10}$ straight chain alkyl; and n is 1 to 4.

For use in the present methods for treating or preventing a viral infection, a preferred subclass of the compounds of Formula (XIII) is that wherein, in the compound of Formula (XIII):

$R_1$ is —H;

$R_2$ is —H or —$CH_3$; and n is 1 to 4.

For use in the present methods for treating or preventing a viral infection, a more preferred subclass of the compounds of Formula (XIII) is that wherein, in the compound of Formula (XIII):

$R_1$ is —H;

$R_2$ is —H or —$CH_3$; and n is 2.

The invention further provides methods for inhibiting the replication or infectivity of a virus comprising contacting a virus or a virus-infected cell with an effective amount of a compound having the general Formula (XIII) or a pharmaceutically acceptable salt thereof, wherein, in the compound of Formula (XIII):

each $R_1$ is independently selected from the group consisting of —H, —$CH_3$, —$CH_2C_6H_5$, —$C(O)OC(CH_3)_3$, or —$C(O)OCH_2C_6H_5$;

$R_2$ is —H or a $C_1$–$C_{10}$ straight chain alkyl; and n is 1 to 4.

For use in the methods for inhibiting the replication or infectivity of a virus, a preferred subclass of the compounds of Formula (XIII) are those wherein:

$R_1$ is —H;

$R_2$ is —H or —$CH_3$; and n is 1 to 4.

For use in the methods for inhibiting the replication or infectivity of a virus, a more preferred subclass of the compounds of Formula (XIII) are those wherein:

$R_1$ is —H;

$R_2$ is —H or —$CH_3$; and n is 2.

The invention further provides methods for causing immunosuppression in a patient comprising administering to a patient in need thereof an effective amount of a compound of Formula (XIII) or a pharmaceutically acceptable salt thereof, wherein, in the compound of Formula (XIII):

each $R_1$ is independently selected from the group consisting of —H, —$CH_3$, —$CH_2C_6H_5$, —$C(O)OC(CH_3)_3$, or —$C(O)OCH_2C_6H_5$;

$R_2$ is —H or a $C_1$–$C_{10}$ straight chain alkyl; and n is 1 to 4.

For use in the methods for causing immunosuppression, a preferred subclass of the compounds of Formula (XIII) are those wherein:

$R_1$ is —H;

$R_2$ is —H or —$CH_3$; and n is 1 to 4.

For use in the methods for causing immunosuppression, a more preferred subclass of the compounds of Formula (XIII) are those wherein:

$R_1$ is —H;

$R_2$ is —H or —$CH_3$; and n is 2.

The invention further provides methods for treating or preventing an autoimmune disease in a patient comprising administering to a patient in need of such treatment or prevention an effective amount of a compound of Formula (XIII) or a pharmaceutically acceptable salt thereof, wherein, in the compound of Formula (XIII):

each $R_1$ is independently selected from the group consisting of —H, —$CH_3$, —$CH_2C_6H_5$, —$C(O)OC(CH_3)_3$, or —$C(O)OCH_2C_6H_5$;

$R_2$ is —H or a $C_1$–$C_{10}$ straight chain alkyl; and n is 1 to 4.

For use in the methods for treating or preventing an autoimmune disease, a preferred subclass of the compounds of Formula (XIII) are those wherein:

$R_1$ is —H;

$R_2$ is —H or —$CH_3$; and n is 1 to 4.

For use in the methods for treating or preventing an autoimmune disease, a more preferred subclass of the compounds of Formula (XIII) are those wherein:

$R_1$ is —H;

$R_2$ is —H or —$CH_3$; and n is 2.

5.14. Racemates and Enantiomers of Formula (I–V) Compounds

As used herein, the term "Pyrrole-Type compounds" means, collectively, the compounds of Formulas (I–XIII) and racemates and enantiomers thereof, and pharmaceutically acceptable salts thereof.

5.15. Synthesis of the Pyrrole-Type Compounds

The compounds of the invention can be obtained via conventional organic syntheses, e.g., as described below. Schemes A–O indicate methods by which compounds of the invention may be obtained.

5.15.1. The Compounds of Formula (I)

The compounds of Formula (I) can be obtained using conventional organic synthesis or by the following illustrative method shown in Scheme A:

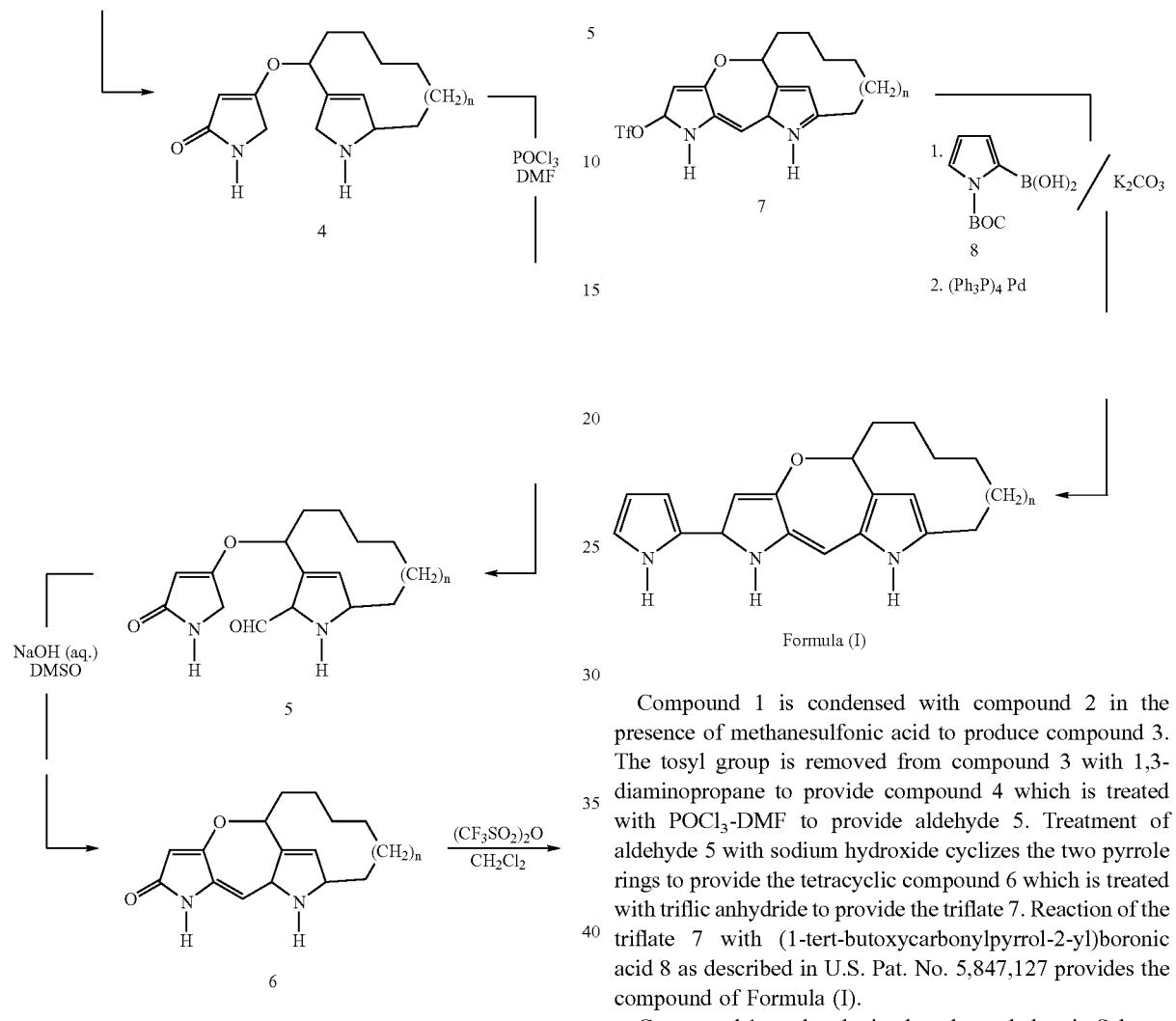

Compound 1 is condensed with compound 2 in the presence of methanesulfonic acid to produce compound 3. The tosyl group is removed from compound 3 with 1,3-diaminopropane to provide compound 4 which is treated with POCl$_3$-DMF to provide aldehyde 5. Treatment of aldehyde 5 with sodium hydroxide cyclizes the two pyrrole rings to provide the tetracyclic compound 6 which is treated with triflic anhydride to provide the triflate 7. Reaction of the triflate 7 with (1-tert-butoxycarbonylpyrrol-2-yl)boronic acid 8 as described in U.S. Pat. No. 5,847,127 provides the compound of Formula (I).

Compound 1 can be obtained as shown below in Scheme A.1.

Scheme A.1

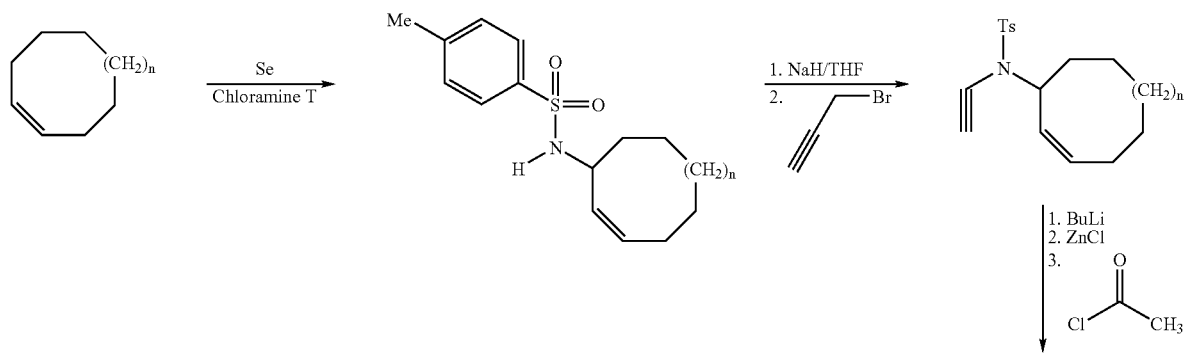

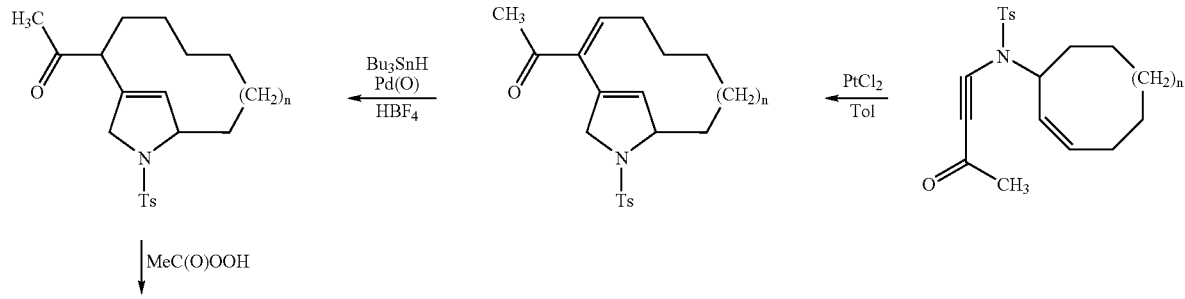

The methods shown in Scheme A.1 for the formation of compound 1 have been described in A. Fürstner et al., J. Am. Chem. Soc., 1998, 120, 8305–8314.

(1-tert-butoxycarbonylpyrrol-2-yl)boronic acid 8 is prepared according to the method in R. D'Alessio et al., Synlett, 1966, 513–514.

5.15.2. The Compounds of Formula (II)

The compounds of Formula (II) can be obtained using conventional organic synthesis or by the following illustrative method shown in Scheme B:

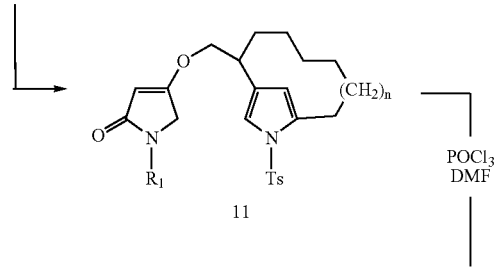

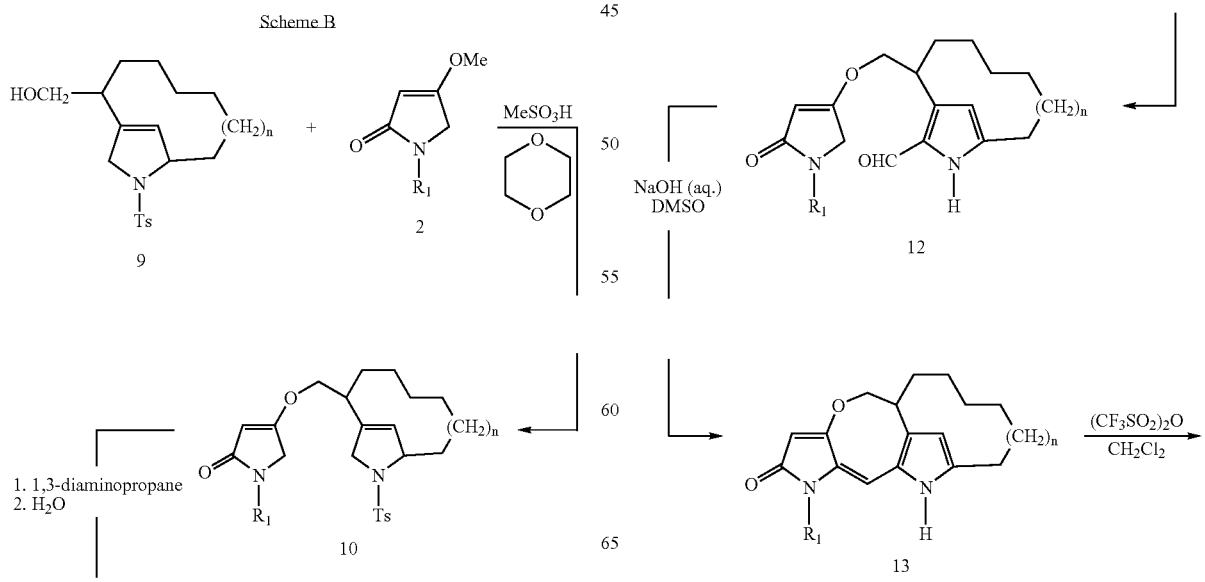

-continued

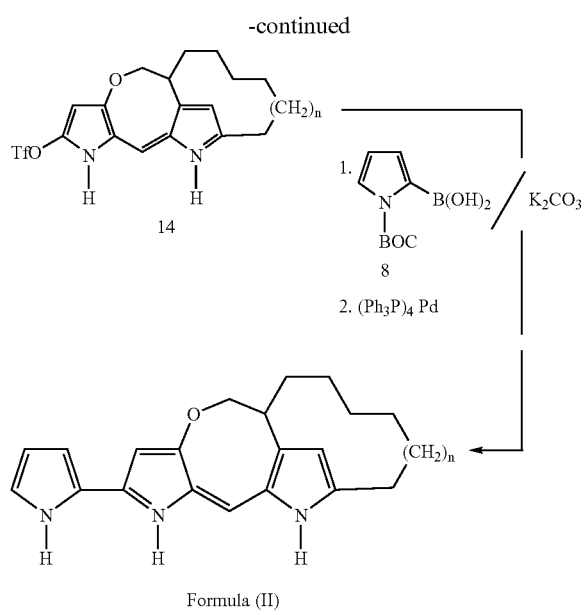

Compound 9 is condensed with compound 2 in the presence of methanesulfonic acid to provide compound 10. The tosyl group is removed from compound 10 with 1,3-diaminopropane to provide compound 11 which is treated with $POCl_3$-DMF to provide aldehyde 12. Treatment of aldehyde 12 with sodium hydroxide cyclizes the two pyrrole rings to provide the tetracyclic compound 13 which is treated with triflic anhydride to provide the triflate 14. Reaction of the triflate 14 with (1-tert-butoxycarbonylpyrrol-2-yl)boronic acid 8 as described in U.S. Pat. No. 5,847,127 provides the compound of Formula (II).

Compound 9 can be obtained as shown below in Scheme B.1.

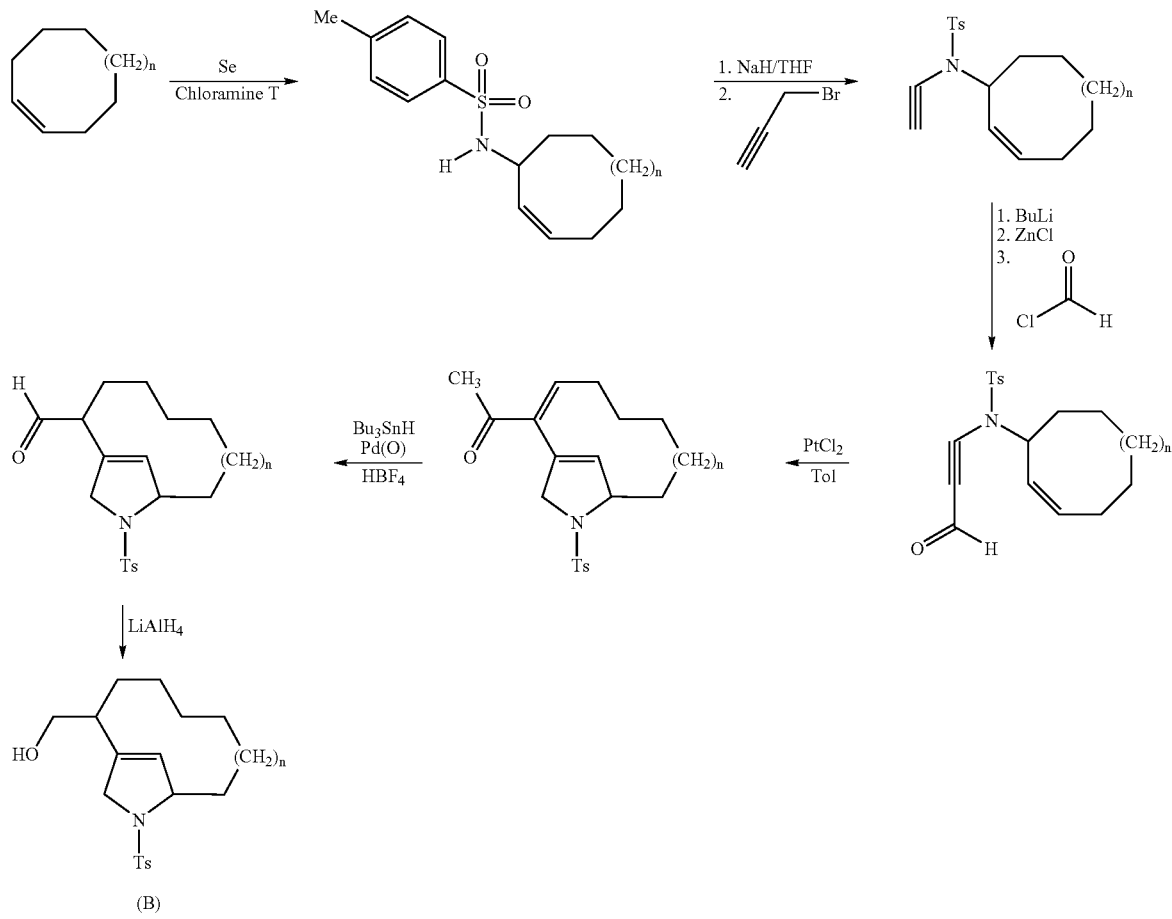

The methods shown in Scheme B.1. for the formation of compound 9 have been described in A. Fürstner et al., J. Am. Chem. Soc., 1998, 120, 8305–8314.

(1-tert-butoxycarbonylpyrrol-2-yl)boronic acid 8 is prepared according to the method in R. D'Alessio et al., Synlett, 1966, 513–514.

5.15.3. The Compounds of Formula (III)

The compounds of Formula (III) can be obtained using conventional organic synthesis or by the following illustrative methods shown in Schemes C and D:

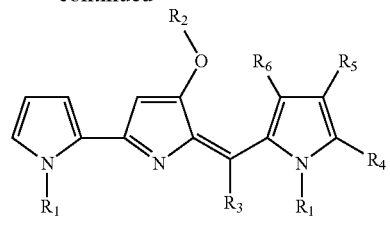

Formula (III)

Compound 15 is prepared according to the method of D. L. Boger et al., J. Org. Chem, 1988, 53, 1405–1415 and converted to the dipyrrole carboxylic ester 16 by treatment with lithium methoxide in methanol and then to the lithium salt of the dipyrrole carboxylic acid 17 by treatment with lithium hydroxide in methanol. The lithium salt of the dipyrrole carboxylic acid 17 is treated with an alkyl lithium or phenyl lithium ($R_3Li$) to provide the dipyrrole ketone 18 which is then coupled with the pyrrole 19 according to the method of D. L Boger et al., J. Org. Chem, 1988, 53, 1405–1415 to provide the compound of Formula (III).

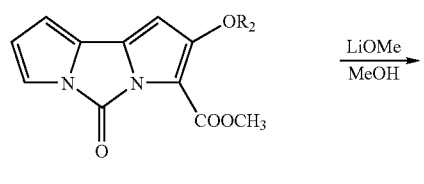

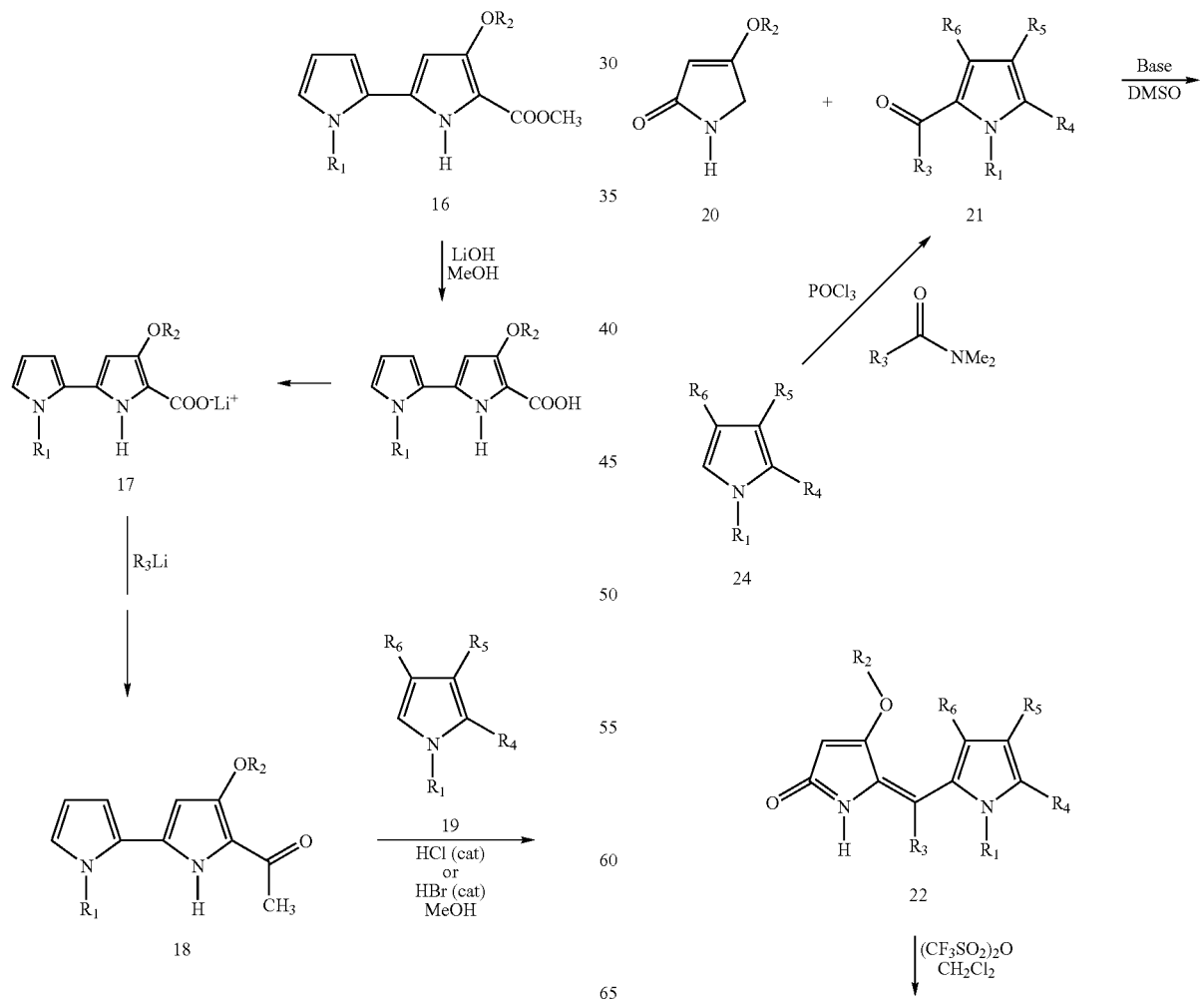

-continued

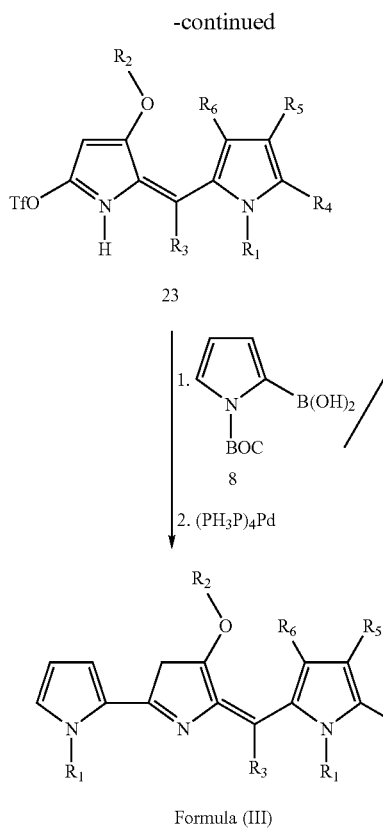

Formula (III)

Compound 20 is coupled with pyrrole 21 to provide compound 22 which is treated with triflic anhydride to provide the triflate 23. Pyrrole 21 is prepared by treating pyrrole 24 with $POCl_3$ and $R_3C(O)N(CH_3)_2$. The triflate 23 is then coupled with (1-tert-butoxycarbonylpyrrol-2-yl)boronic acid 8 according to the method in U.S. Pat. No. 5,847,127 to provide the compound of Formula (III).

Compound 20 is prepared according to the procedure in L. Duc et al., Synthesis, 1992, 391–394.

(1-tert-butoxycarbonylpyrrol-2-yl)boronic acid 8 is prepared according to the method in R. D'Alessio et al., Synlett, 1966, 513–514.

5.15.4. The Compounds of Formula (IV)

The compounds of Formula (IV) can be obtained using conventional organic synthesis or by the methods shown in Schemes E and F:

Scheme E.

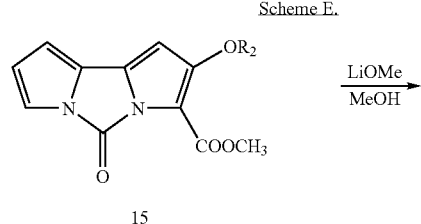

15

-continued

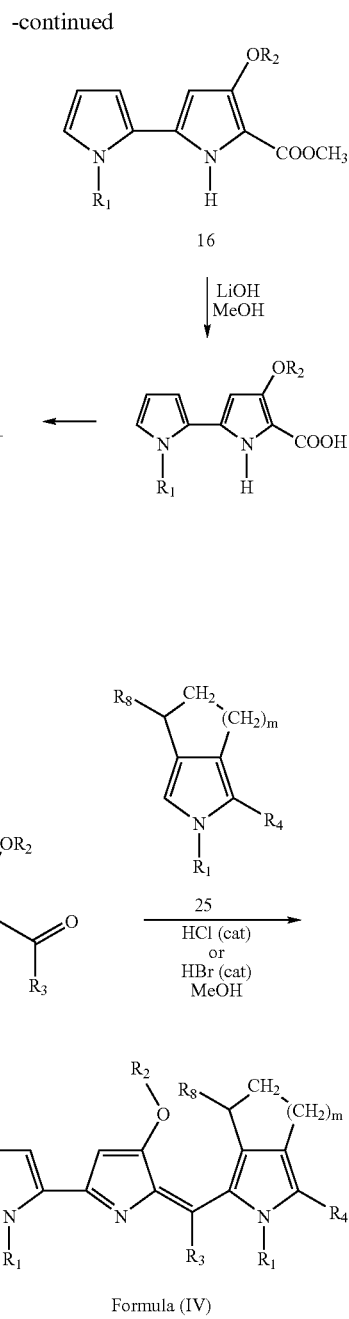

Formula (IV)

Compound 15 is prepared according to the method of D. L. Boger et al., J. Org. Chem, 1988, 53, 1405–1415 and converted to the dipyrrole carboxylic ester 16 by treatment with lithium methoxide in methanol and then to the lithium salt of the dipyrrole carboxylic acid 17 by treatment with lithium hydroxide in methanol. The lithium salt of the dipyrrole carboxylic acid 17 is then treated with an alkyl lithium or phenyl lithium ($R_3Li$) to provide the dipyrrole ketone 18 which is coupled with pyrrole 25 according to the method of D. L. Boger et al., J. Org. Chem, 1988, 53, 1405–1415 to provide the compound of Formula (IV).

Pyrrole 25 can be obtained starting with the appropriate substituted cycloalkanone 26 as shown in Scheme E.1.

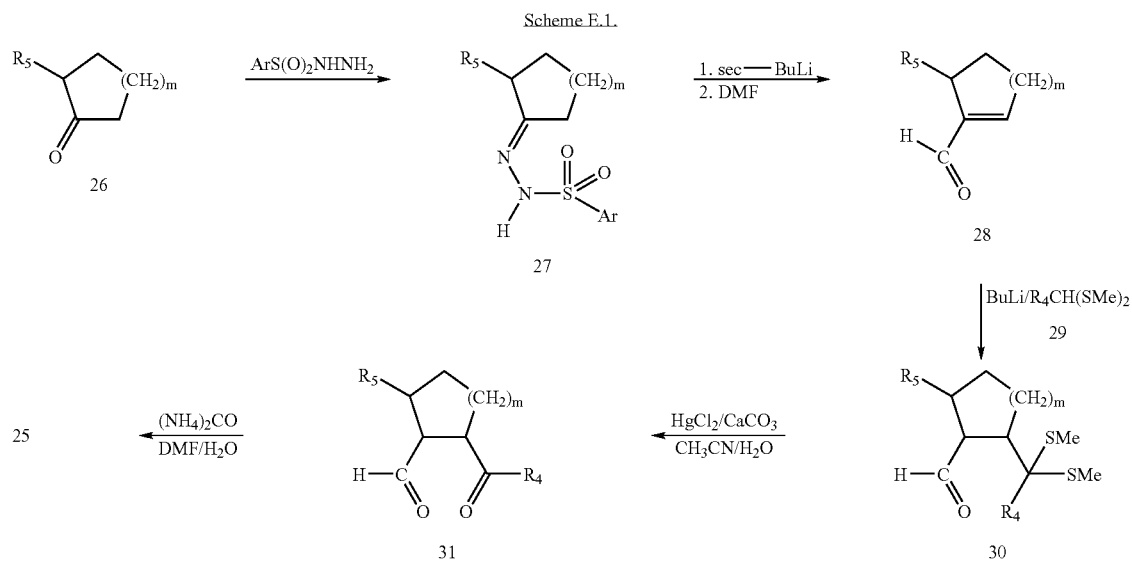

Scheme E.1.

The reaction of cycloalkanone 26 with 2,4,6-tri-i-propylphenylsulfonyl hydrazine gives the corresponding hydrazone 27. Compound 27 is reacted with sec-butyllithium and N,N-dimethylformamide (DMF) to give the α,β-unsaturated aldehyde 28. The anion of a dimethylthioacetaldehyde reagent 29 is generated using n-butyllithium and adds to the conjugated system of 28 producing 30. The group $R_4$ in 30 may be hydrogen or a $C_1$–$C_{12}$ alkyl. Reaction of 30 with mercury(II) chloride and calcium carbonate converts the dimethylthiocarbonyl 30 into a carbonyl group generating 31. Compound 31 reacts with ammonium carbonate in DMF providing the pyrrole 25. The methods shown in Scheme E.1 for the chemical transformation of compound 26 into compound 25 have been described by H. H. Wasserman and J. M. Fukuyama, Tetrahedron Lett. 25, 1387–1388, 1984.

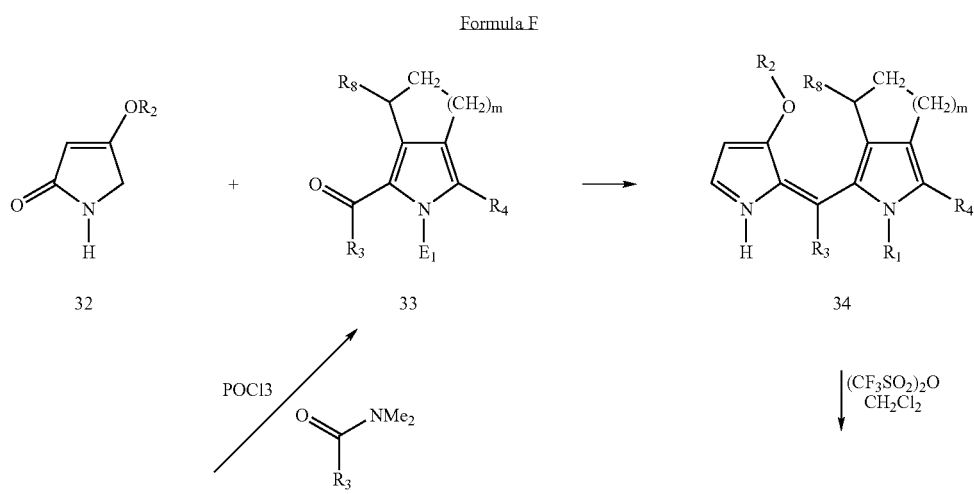

Formula F

-continued

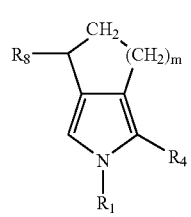

36

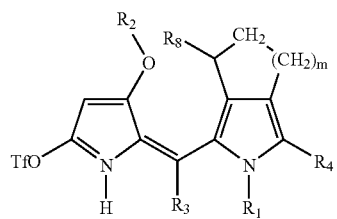

35

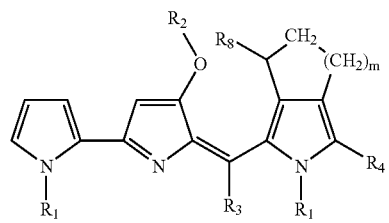

Formula (IV)

Compound 32 is coupled with pyrrole 33 to provide compound 34 which is treated with triflic anhydride to provide the triflate 35. Pyrrole 33 is prepared by treating pyrrole 36 with $POCl_3$ and $R_3C(O)N(CH_3)_2$. The triflate 35 is then coupled with (1-tert-butoxycarbonylpyrrol-2-yl)boronic acid 8 according to the method in U.S. Pat. No. 5,847,127 to provide the compound of Formula (IV).

Compound 32 is prepared according to the procedure in L. Duc et al., Synthesis, 1992, 391–394.

(1-tert-butoxycarbonylpyrrol-2-yl)boronic acid 8 is prepared according to the method in R. D'Alessio et al., Synlett, 1966, 513–514. Pyrrole 33 can be obtained starting with the appropriate substituted cycloalkanone 26 as shown in Scheme E.1.

5.15.5. The Compounds of Formula (V)

The compounds of Formula (V) can be obtained using conventional organic synthesis or by the methods shown in Schemes G and H:

Scheme G

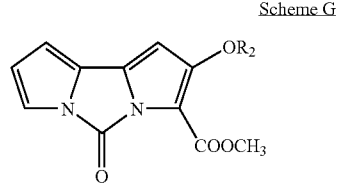

15

-continued

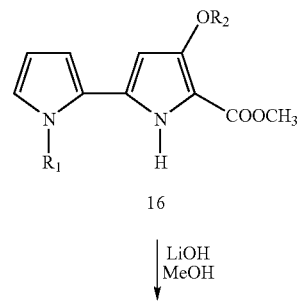

16

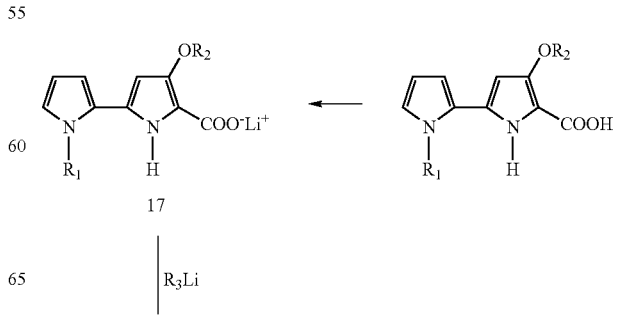

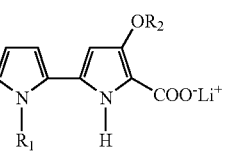

17

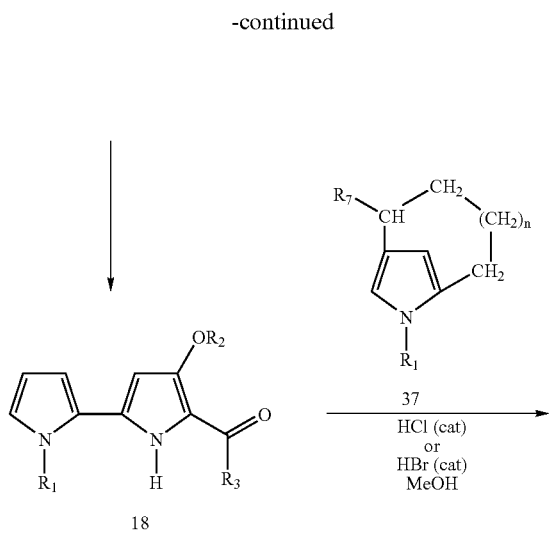

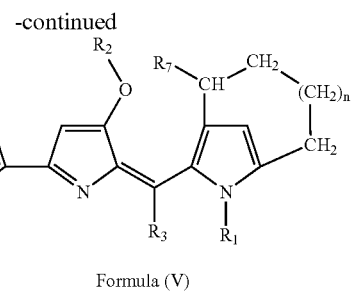

Formula (V)

Compound 15 is prepared according to the method of D. L. Boger et al., J. Org. Chem, 1988, 53, 1405–1415 and converted to the dipyrrole carboxylic ester 16 by treatment with lithium methoxide in methanol and then to the lithium salt of the dipyrrole carboxylic acid 17 by treatment with lithium hydroxide in methanol. The lithium salt of the dipyrrole carboxylic acid 17 is then treated with methyl lithium or benzyl lithium ($R_3Li$) to provide the dipyrrole ketone 18 which is coupled with the pyrrole 37 according to the method of D. L. Boger et al., J. Org. Chem, 1988, 53, 1405–1415 to provide the compound of Formula (V).

Scheme G.1.
The methods used for the synthesis of pyrroles of structure 37 are outlined in Scheme G.1.

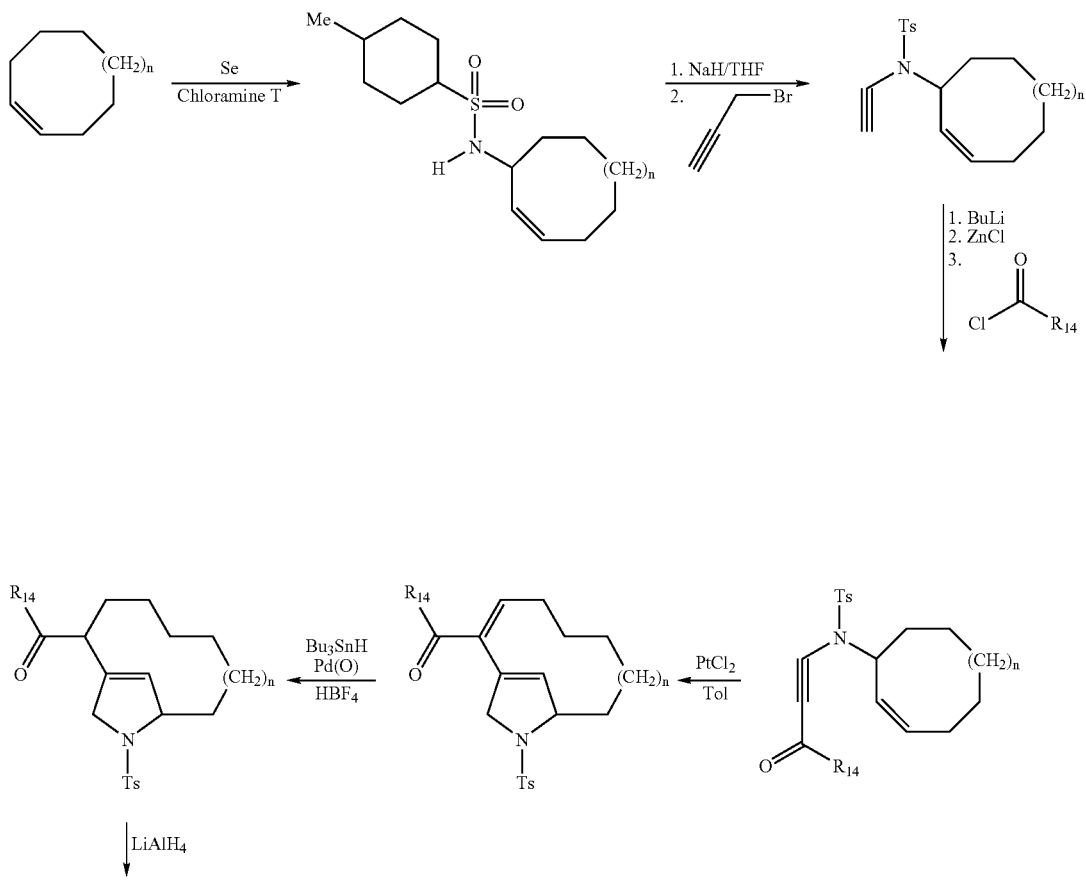

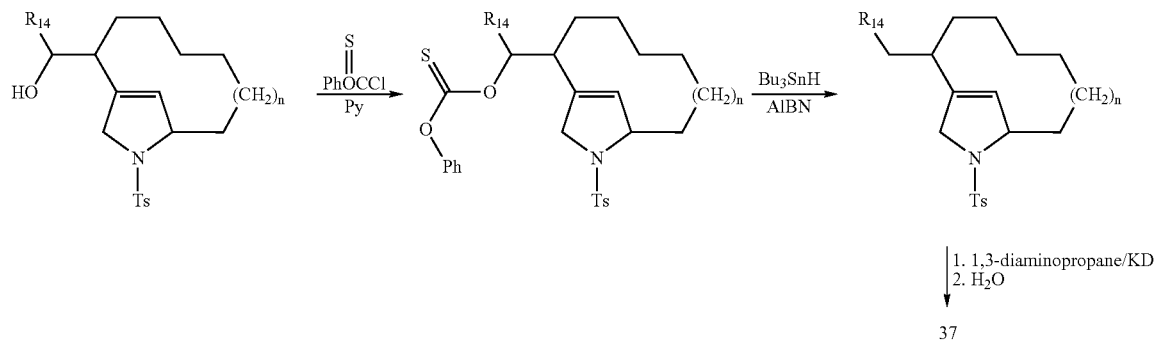

In Scheme G.1., $R_{14}$ is $R_7$ less its α-carbon. These methods have been described by A. Fürstner et al., J. Am. Chem. Soc. 120, 8305–8314, 1998. Compounds 37 where m is 2–5 are prepared by replacing cis-cyclooctene (m=1) with cis-cyclononene, cis-cyclodecene, cis-cycloundecene, and cis-cyclododecene (m=2, 3, 4, and 5, respectively). The structure of the $R_7$ group (—H, a $C_1$–$C_{10}$ straight chain alkyl, or —CH(CH$_3$)$_2$,) in compounds 37 is determined by the choice of the acid chloride, $R_{14}$C(O)Cl. Acid chlorides are prepared from their corresponding carboxylic acids by using thionyl chloride, oxalyl chloride, and/or other methods known in the art.

Scheme H

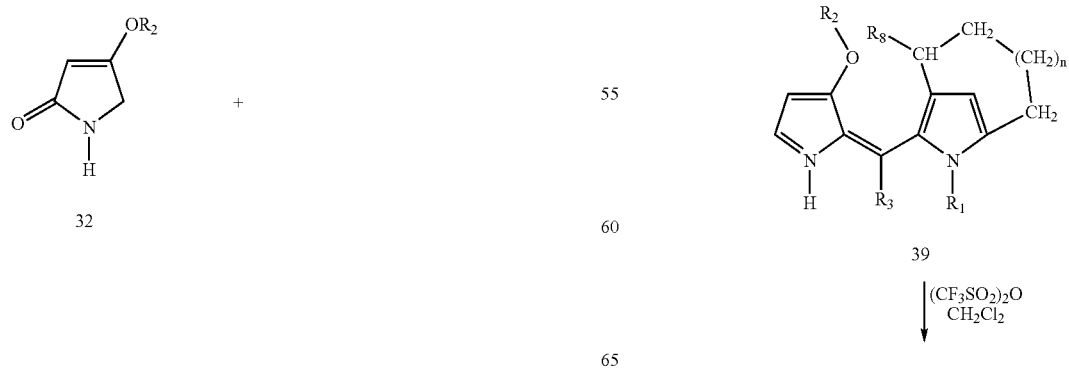

32

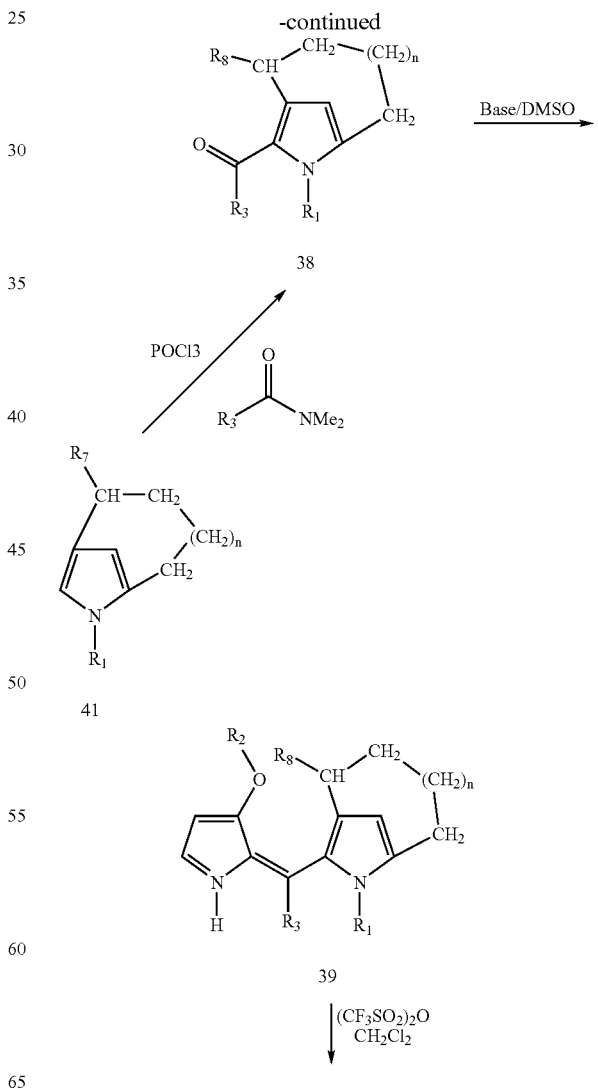

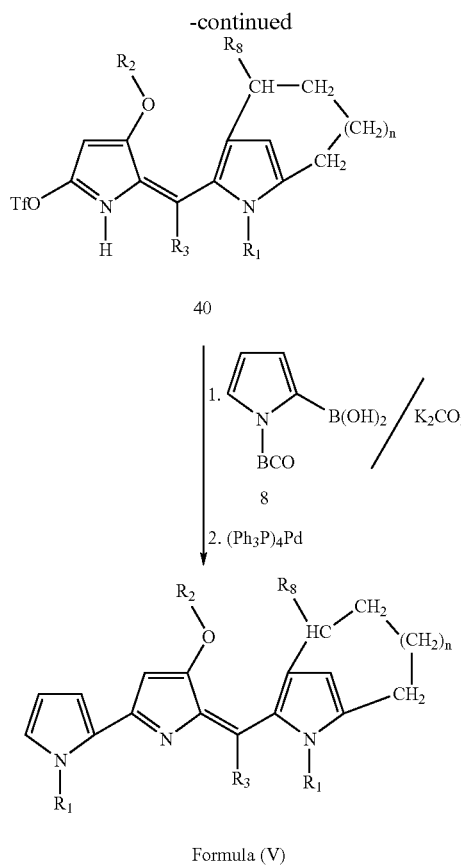

Formula (V)

Compound 32 is coupled with pyrrole 38 to provide the compound 39 which is treated with triflic anhydride to provide triflate 40. Pyrrole 38 is prepared by treating pyrrole 41 with $POCl_3$ and $R_3C(O)N(CH_3)_2$. The triflate 40 is then coupled with (1-tert-butoxycarbonylpyrrol-2-yl)boronic acid 8 according to the method in U.S. Pat. No. 5,847,127 to provide the compound of Formula (V).

Compound 32 is prepared according to the procedure in L. Duc et al., Synthesis, 1992, 391–394.

(1-tert-butoxycarbonylpyrrol-2-yl)boronic acid 8 is prepared according to the method in R. D'Alessio et al., Synlett, 1966, 513–514.

5.15.6. The Compounds of Formula (VI, VII, and VIII)

The compounds of Formula (VI), (VII), and (VIII) can be obtained using conventional organic synthesis or by the methods shown in Scheme I.1.:

Scheme I.1.

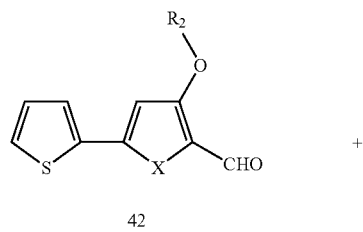

42

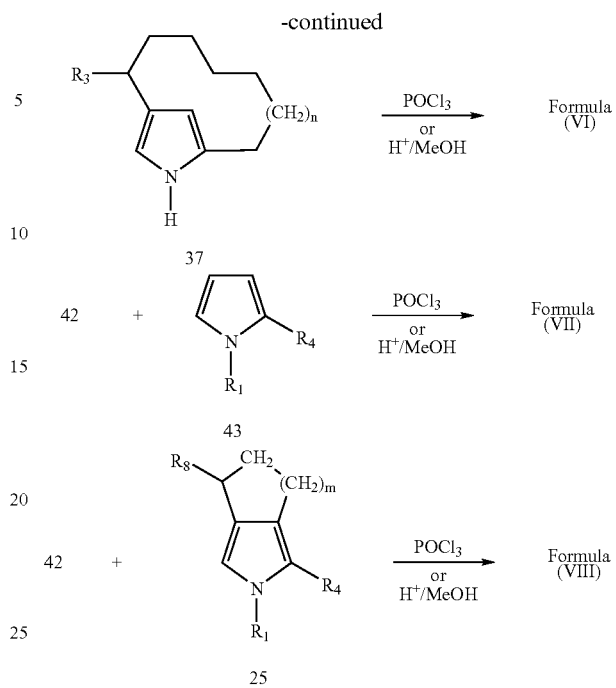

Compound 42 is condensed with pyrrole 37 to provide the compound of Formula (VI), with pyrrole 43 to provide the compound of Formula (VII), or pyrrole 25 to provide the compound of Formula (VIII).

Compound 42 is obtained by the procedure described in A. J. Blake et al., J. Chem. Soc., Chem. Comm., 1990, 734–736.

Pyrrole 37 is obtained as shown in Scheme G.1. In Scheme G.1., $R_{14}$ is $R_3$ less its α-carbon. The methods of Scheme G.1. for the formation of compound 37 have been described in A. Furstner et al., J. Am. Chem. Soc., 1998, 120, 8305–8314.

Pyrrole 25 can be obtained starting with the appropriate substituted cycloalkanone 26 as shown in Scheme E.1. The methods shown in Scheme E.1 for the chemical transformation of compound 26 into compound 25 have been described by H. H. Wasserman and J. M. Fukuyama, Tetr. Lett. 25, 1387–1388, 1984.

Pyrroles 43 are commercially available or can be readily prepared from commercially available starting materials using methods well known to those of ordinary skill in the art (See, e.g., G. P. Bear, "The Synthesis of 1-H-Pyrroles" in "Pyrroles," vol. 1, edited by R. A. Jones, Wiley, NY, 1990, 105–294.; J. H. Liu et al., J. Org. Chem., 2000, 65, 3274–3283; D. Enders et al., Tetr. Lett., 1995, 35, 8007–8010; and J. Tang and J. G. Verkade, J. Org. Chem., 1994, 59, 7793–7802; and B. Franck et al., Liebigs Ann. Chemie, 1994, 503–510).

5.15.6.1 The Compounds of Formula (VII)

In one embodiment, the compounds of Formula (VII), wherein $R_2$ and $R_4$ are defined above for the compounds of Formula (VII), can be obtained using conventional organic synthesis or by the methods shown in Scheme I.2. below:

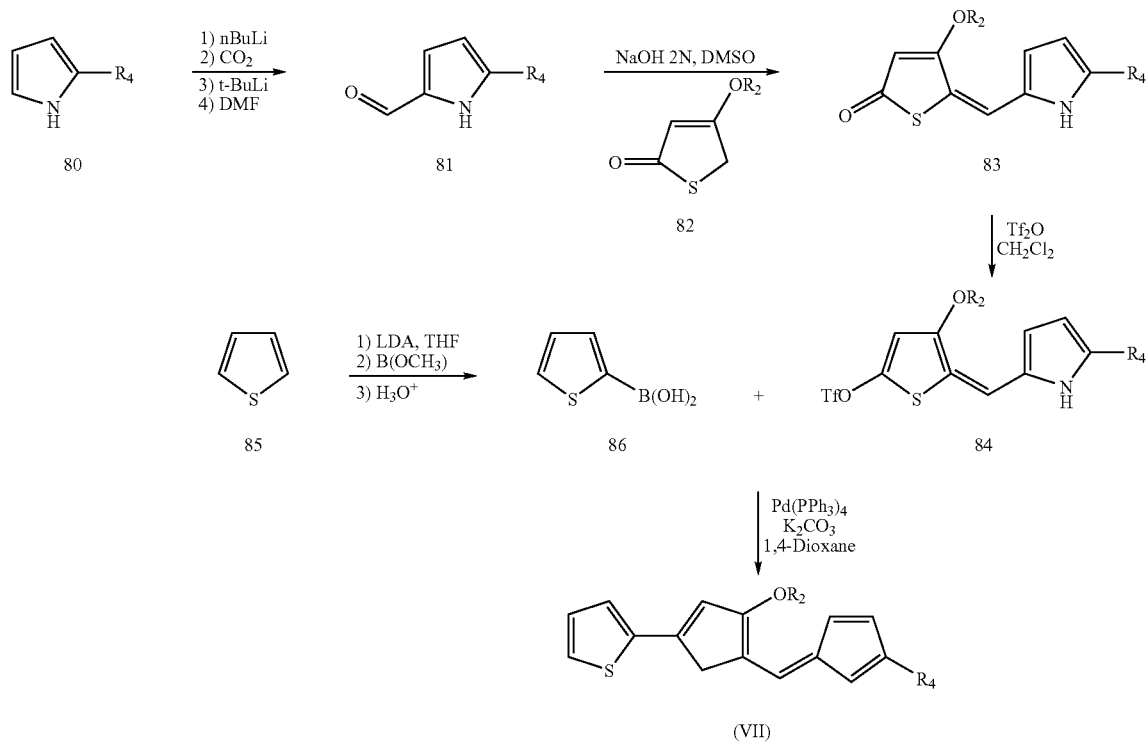

The aldehydic pyrrole 81 and the heterocyclic boronate 86 are prepared as shown in Scheme I.2. Compound 81 is then coupled with synthetically or commercially accessible 82 to give Compound 83, which is then converted to the triflate 84. A compound of Formula (VII) is obtained from Suzuki coupling of the boronate 86 and the triflate 84.

5.15.7. The Compounds of Formula (IX)

The compounds of Formula (IX) can be obtained using conventional organic synthesis or by the methods shown in Scheme J:

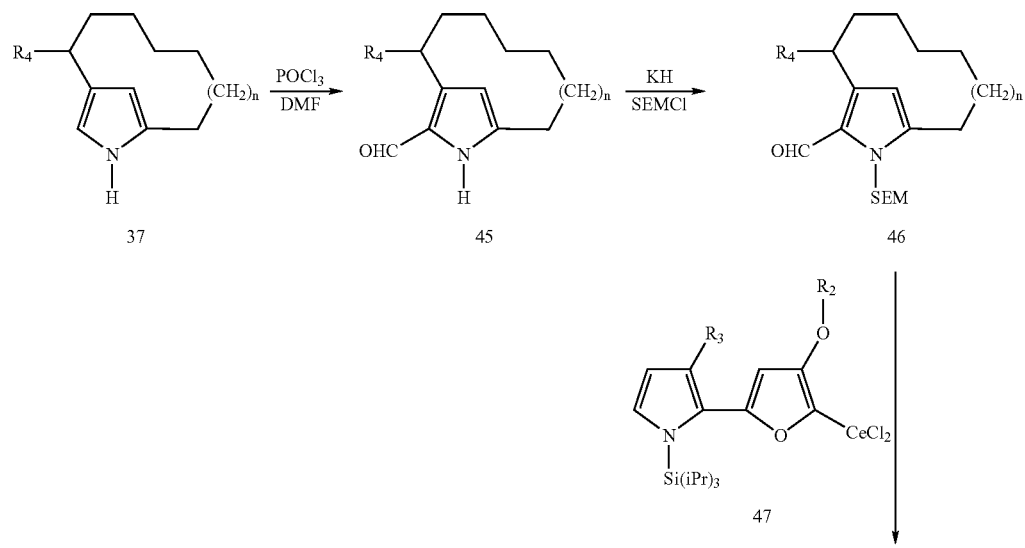

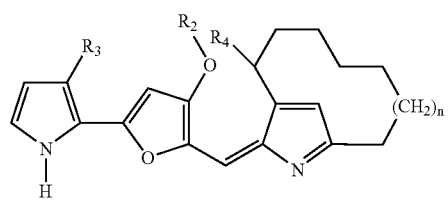

Formula (IX)

TBAF / THF ←

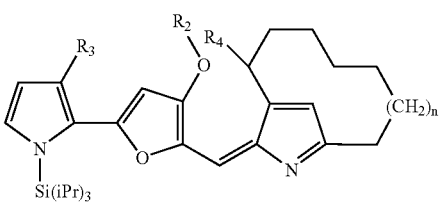

48

Pyrrole 37 is converted to aldehyde 45 with POCl₃ in DMF and then to compound 46 by treatment with potassium hydride and SEMCl. Compound 46 is reacted with compound 47, prepared using the method described in A. Furstner et al., J. Amer. Chem. Soc., 1998, 120, 2817–2825, to provide compound 48. The tri-isopropylsilyl group is removed from compound 48 using tetra-butylammonium fluoride (TBAF) in tetrahydrofuran to provide the compound of Formula (IX).

Pyrrole 44 can be obtained using the method shown in Scheme G.1. The methods of Scheme G.1. for the formation of compound 37 have been described in A. Furstner et al., J. Am. Chem. Soc., 1998, 120, 8305–8314.

5.15.8. The Compounds of Formula (X)

The compounds of Formula (X) can be obtained using conventional organic synthesis or by the methods shown in Scheme K:

Dipyrrole aldehyde 49 is condensed with compound 50 using POCl₃ or H⁺ in an organic solvent, such as methanol, to provide the compound of Formula (X).

Dipyrrole aldehyde 49 can be prepared by the method of D. L. Boger et al., J. Org. Chem, 1988, 53, 1405–1415. Compound 50 can be prepared from commercially available starting materials using methods well known to those of ordinary skill in the art (See, e.g., B. Robinson, "The Fischer Indole Synthesis," Wiley, NY, 1983; H. Ishii, Accts. Chem. Res., 1981, 14, 275–283; and D. C. Soderberg et al., J. Org. Chem., 1999, 64, 9731–9734).

Representative examples of the synthesis of compounds of Formula (X) are provided in Scheme K.1. and K.2. below:

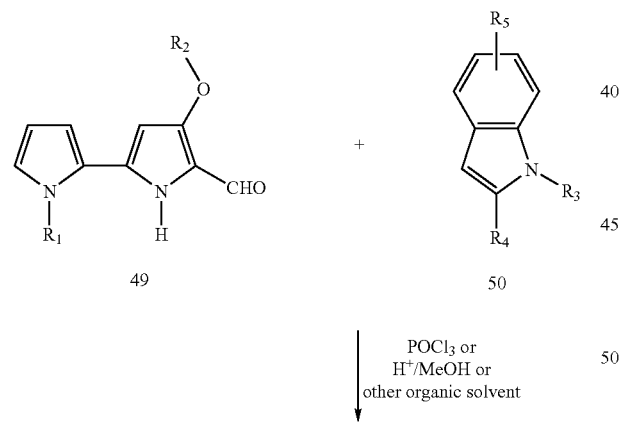

Formula (X)

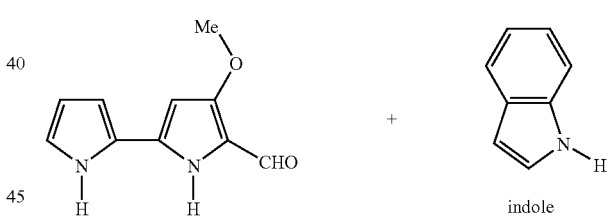

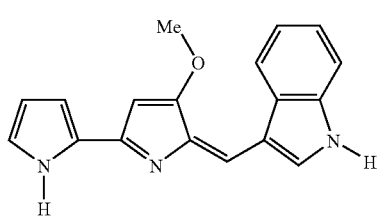

Scheme K.2

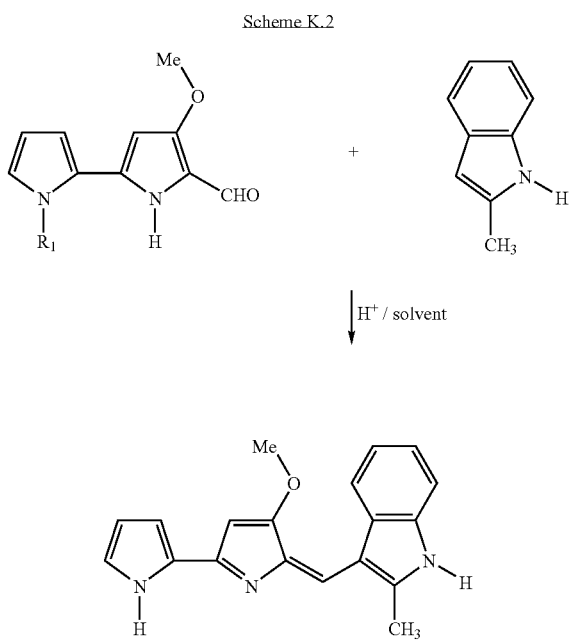

5.15.9. The Compounds of Formula (XI)

The compounds of Formula (XI) can be obtained using conventional organic synthesis or by the methods shown in Scheme L:

Scheme L

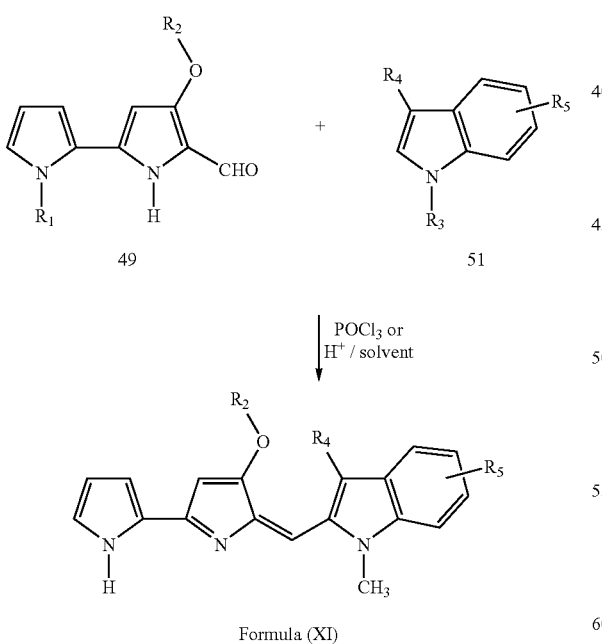

Formula (XI)

Dipyrrole aldehyde 49 is condensed with compound 51 using POCl₃ or H⁺ to provide the compound of Formula (XI).

Dipyrrole aldehyde 49 can be prepared by the method of D. L. Boger et al., J. Org. Chem, 1988, 53, 1405–1415.

Compound 51 can be prepared from commercially available starting materials using methods well known to those of ordinary skill in the art (See, e.g., B. Robinson, "The Fischer Indole Synthesis," Wiley, NY, 1983; H. Ishii, Accts. Chem. Res., 1981, 14, 275–283; D. C. Soderberg et al., J. Org. Chem., 1999, 64, 9731–9734, Anderson and Loader, Synthesis, 1985, 353–364; and E. Abel et al., Chem. Comm., 2000, 433–434).

Specific examples of the synthesis of compounds of Formula (XI) are provided in Scheme L.1., L.2, and L.3. below:

Scheme L.1.

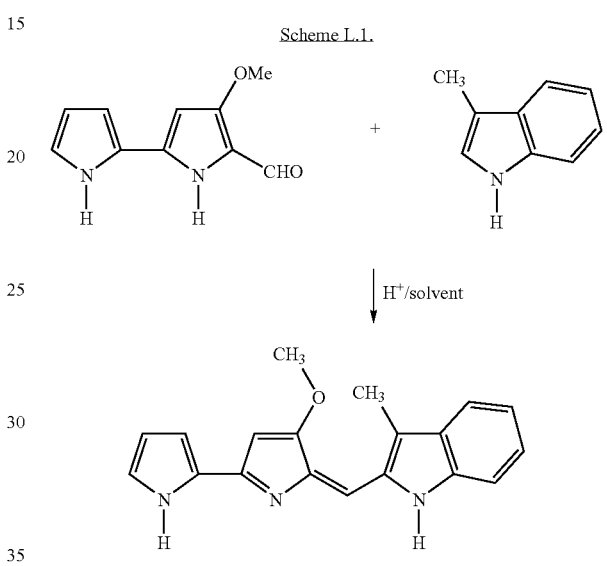

Scheme L.2.

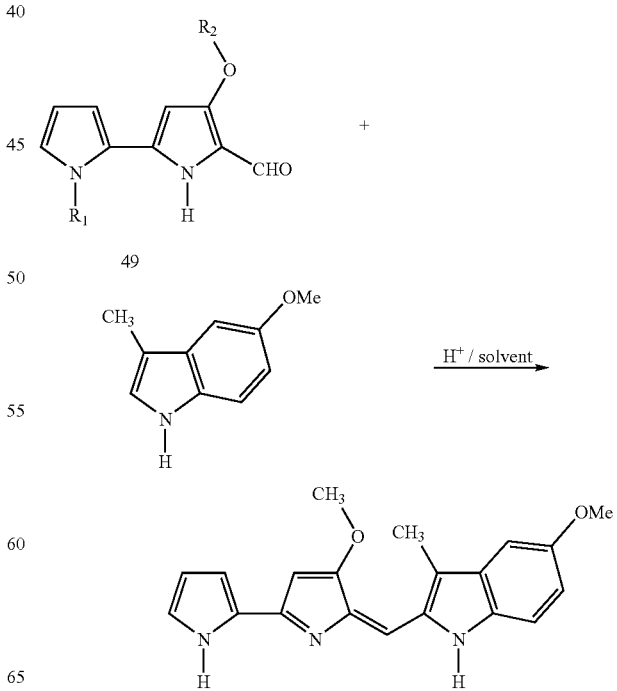

Scheme L.3.
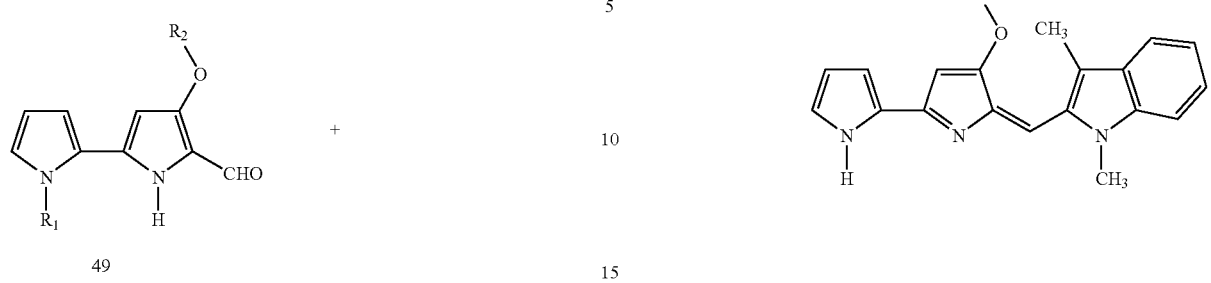
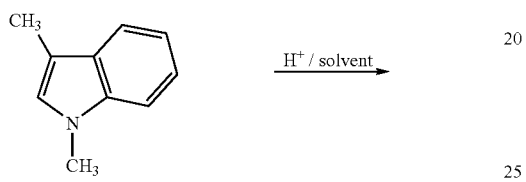
5.15.10. The Compounds of Formula (XII)
The compounds of Formula (XII) can be obtained using conventional organic synthesis or, except for $R_3$=to —H, —SO$_2$CH$_3$, and —SO$_2$C$_6$H$_5$, by the methods shown in Scheme M:
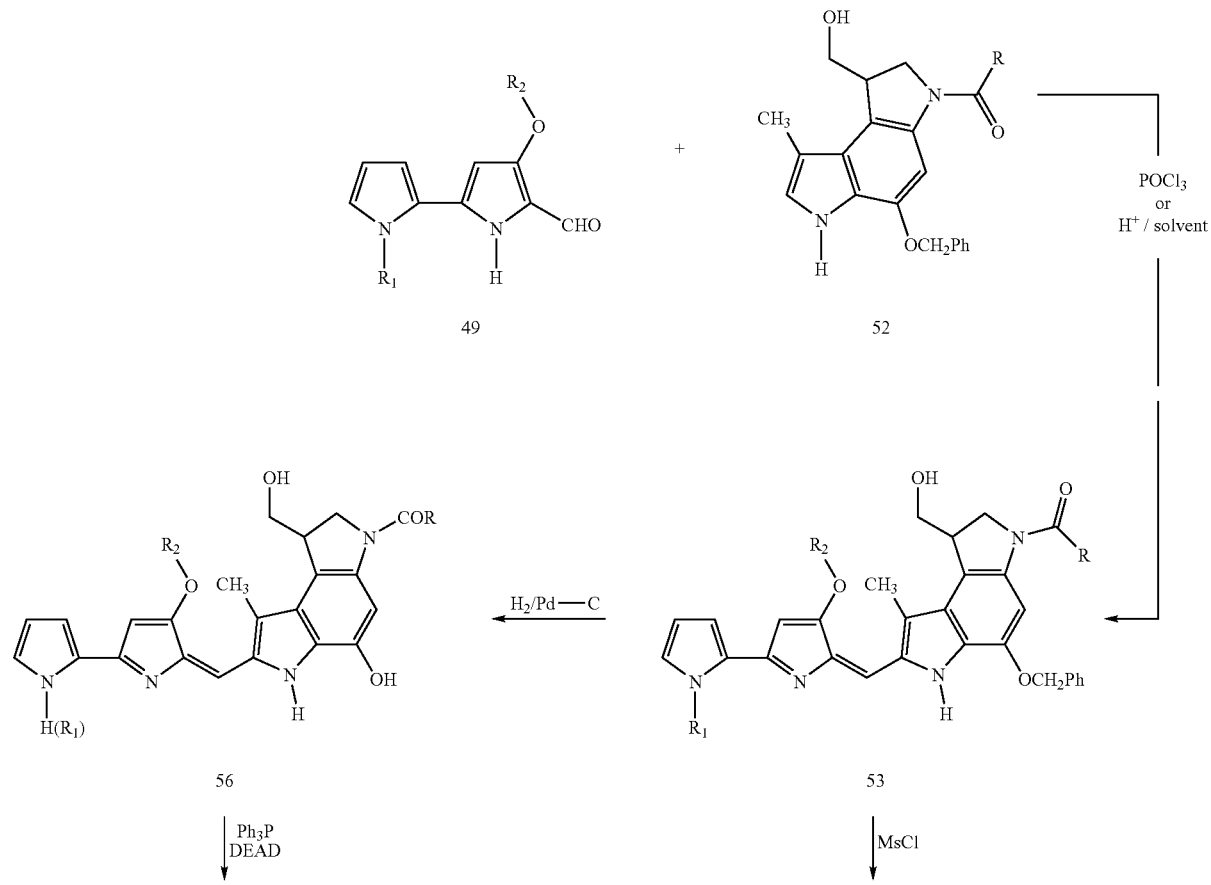

-continued

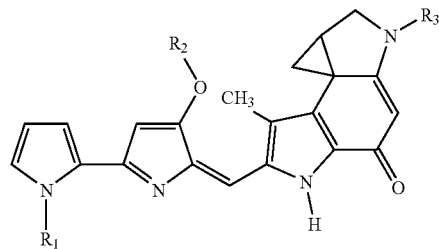

Formula (XII)
(except where R₃ = H, SO₂Me, and SO₂C₆H₅)

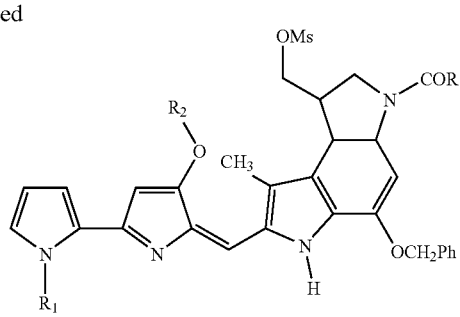

54

H₂/Pd—C
or TMSI
or BBr₃

Et₃N

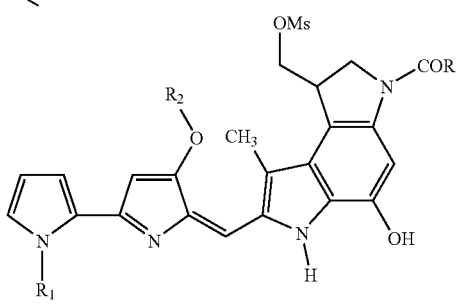

55

Dipyrrole aldehyde 49 is condensed with compound 52 using POCl₃ or H⁺ to provide compound 53. Compound 53 is then treated with methanesulfonyl chloride to provide the mesylate 54 which is hydrogenated over palladium and charcoal, treated with iodotrimethylsilane, or treated with boron tribromide to remove the benzyl group and provide compound 55. Treatment of compound 55 with triethylamine provides the compound of Formula (XII). Alternatively, the benzyl group can be removed from compound 53 by hydrogenolysis to provide compound 56 which can be treated with triphenylphosphine and DEAD to provide the compound of Formula (XII).

Dipyrrole aldehyde 49 can be prepared by the method of D. L. Boger et al., J. Org. Chem, 1988, 53, 1405–1415. Compound 52 can be prepared by the method of M. A. Warpehoski et al., J. Med. Chem., 1988, 31, 590–603.

Compounds of Formula (XII), wherein R₃ is —H are prepared by the following reaction:

-continued

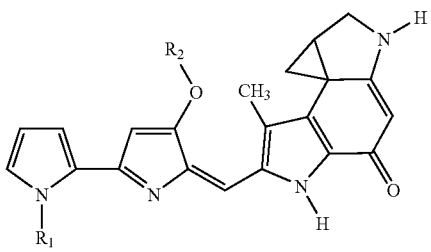

Formula (XII)
where R₃ = H

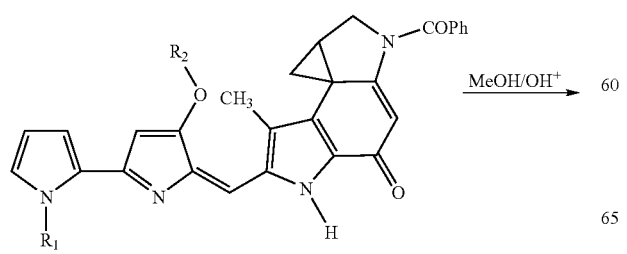

MeOH/OH⁺

Compounds of Formula (XII), wherein R₃ is —SO₂CH₃ or —SO₂C₆H₅ can be prepared by the methods shown in Scheme N:

Scheme N

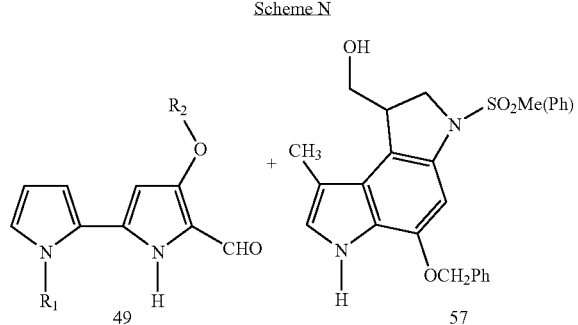

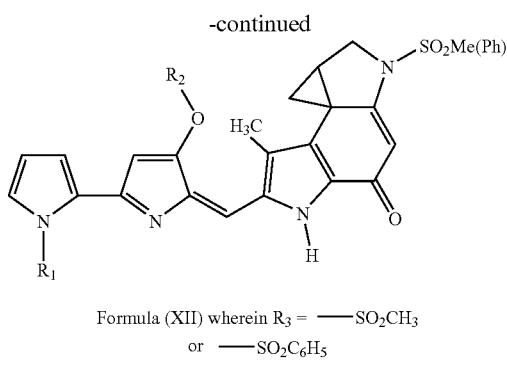

Formula (XII) wherein $R_3 = $ —$SO_2CH_3$
or —$SO_2C_6H_5$

Compound 57 is condensed with compound 49, prepared by the method of D. L. Boger et al., J. Org. Chem, 1988, 53, 1405–1415, to provide compound 58. Compound 58 is treated with methanesulfonyl chloride; hydrogenated over palladium and charcoal, reacted with trimethylsilane, or reacted with tribromoborane; and treated with triethylamine to provide a compound of Formula (XII), wherein $R_3$ is —$SO_2CH_3$ or —$SO_2C_6H_5$.

Compound 57 can be prepared by the method of M. A. Warpehoski et al., J. Med. Chem., 1988, 31, 590–603.

5.15.11. The Compounds of Formula (XIII)

The compounds of Formula (XIII) can be obtained using conventional organic synthesis or by the methods shown in Scheme O:

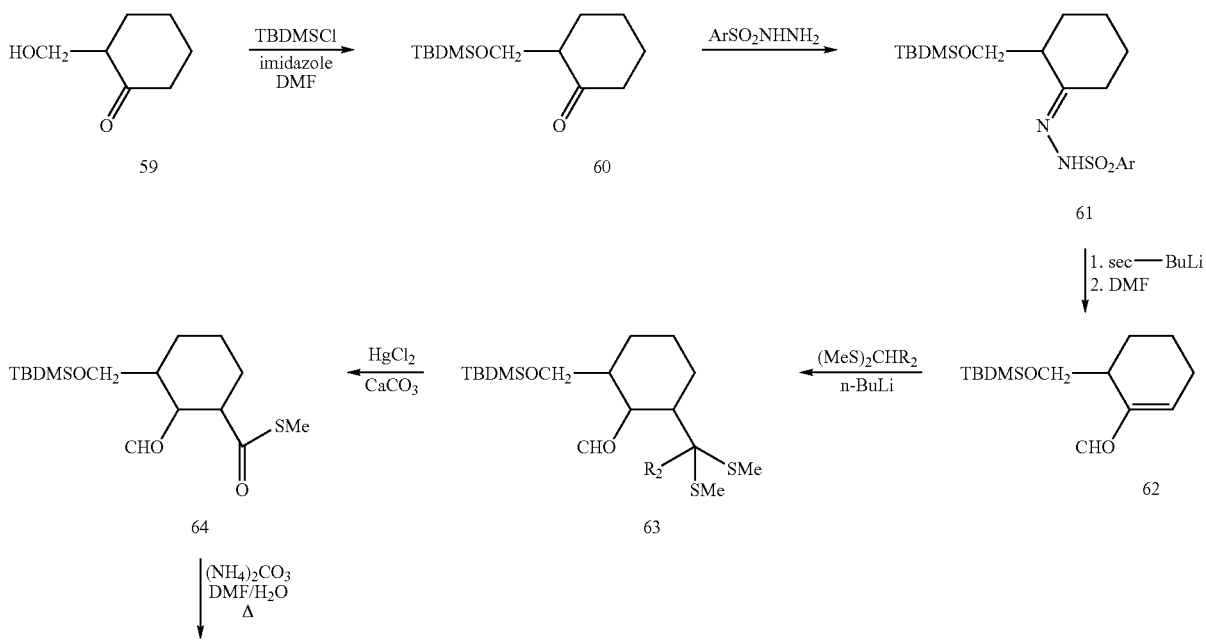

-continued
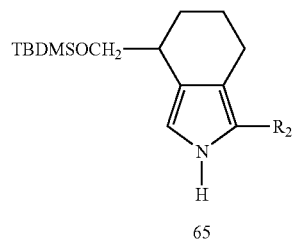
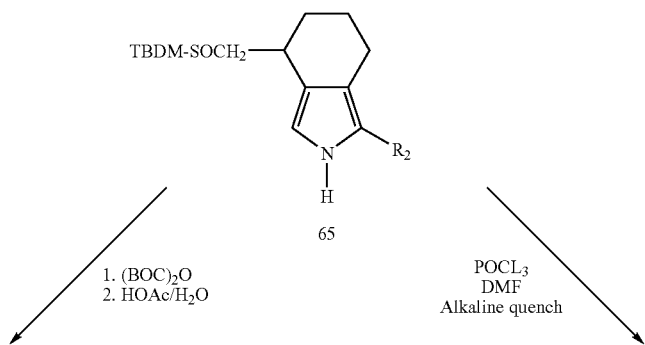
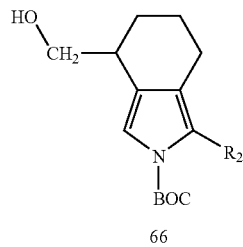
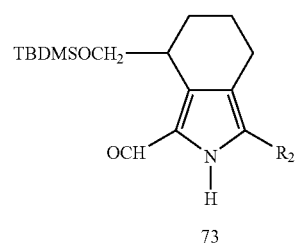
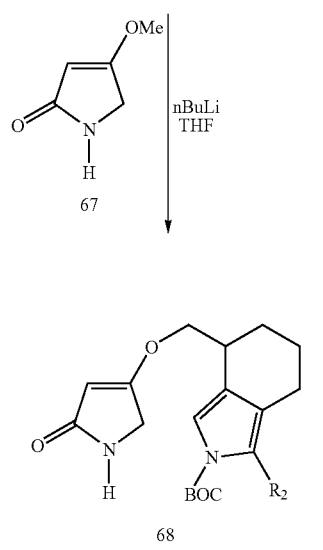
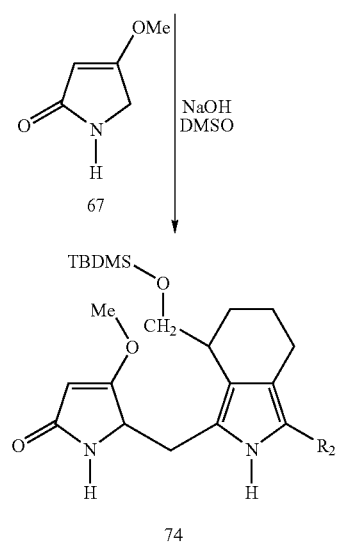

-continued
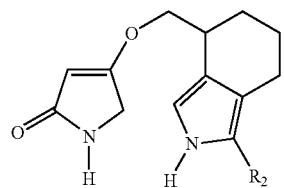
69
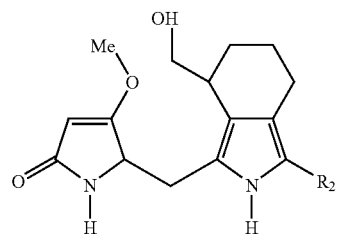
75
| POCl₃
| DMF
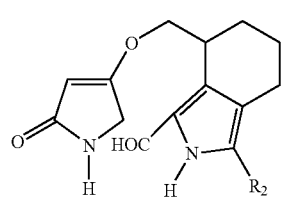
70
NaOH
DMSO
CH₃SO₃H
dioxane
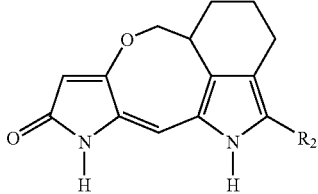
71
Tf₂O
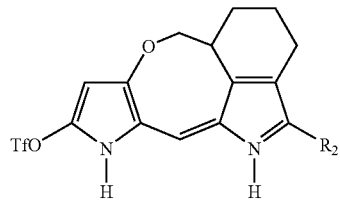
72
Pd(O)
K₂CO₃
[pyrrole-B(OH)₂, N-BOC]
8

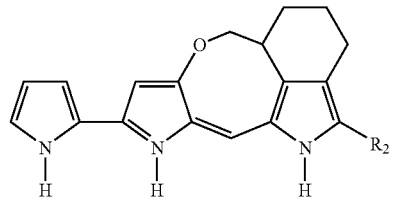

Formula (XIII)

Compound 59 is treated with tert-butyldimethylsilyl chloride in the presence of imidazole to provide compound 60 which is then treated with ArSO₂NHNH₂ to provide compound 61. Treatment of compound 61 with sec-butyl lithium provides the unsaturated aldehyde 62 which is reacted with (MeS)₂CHR₂ in the presence of n-butyl lithium to provide compound 63 which is converted with mercury (II) chloride to the dicarbonyl compound 64. Dicarbonyl compound 64 is then treated with ammonium carbonate to provide compound 65. Reaction of compound 65 with (BOC)₂O followed by treatment with aqueous acetic acid provides compound 66. Compound 66 is reacted with commercially available pyrrolinone 67, in the presence of n-butyl lithium to provide compound 68. The BOC group is removed from compound 68 to provide compound 69 which is treated with POCl₃-DMF to provide aldehyde 70. Aldehyde 70 is then reacted with sodium hydroxide in DMSO to provide compound 71 which is reacted with triflic anhydride to provide triflate 72. Triflate 72 is reacted with (1-tert-butoxycarbonylpyrrol-2-yl)boronic acid 8, prepared according to the method in R. D'Alessio et al., Synlett, 1966, 513–514, to provide the compound of Formula (XIII).

Alternatively, compound 71 can be prepared by treating compound 65 with POCl₃-DMF followed by an alkaline quench to provide compound 73 which is reacted with pyrrolinone 67 in the presence of sodium hydroxide in DMSO to provide compound 74 which is treated with aqueous sodium acetate to provide compound 75. Compound 75 is treated with trimethylsulfonic acid to provide compound 71.

Once the compounds of Formula (I)–(XIII) have been synthesized, they can be purified or substantially purified, using conventional chromatography, recrystallization or other purification techniques known to those skilled in the art.

5.15.12. Illustrative Pyrrole-Type Compounds

Illustrative compounds of Formula (III) are:

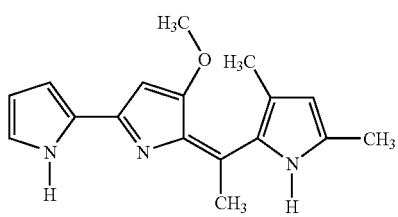

5'-[1-(3,5-Dimethyl-1H-pyrrol-2-yl)-ethylidene]-4'-methoxy-1H,5'H-[2,2']bipyrrolyl;

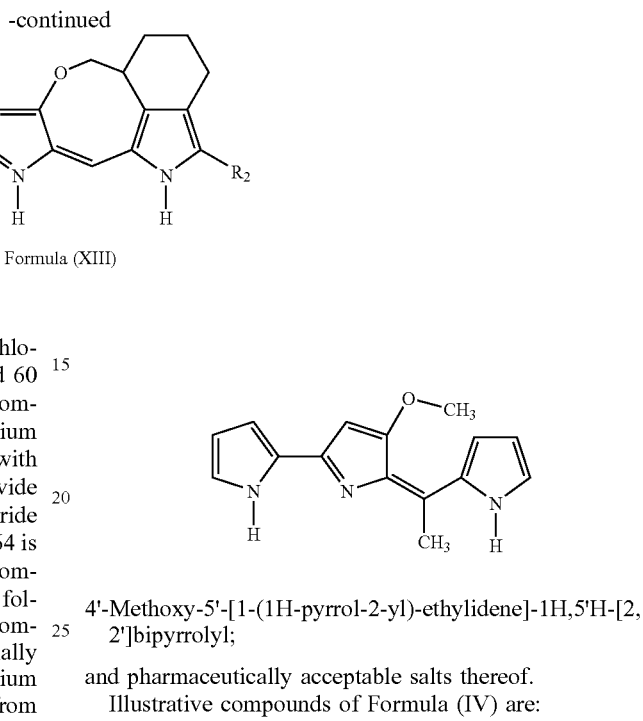

4'-Methoxy-5'-[1-(1H-pyrrol-2-yl)-ethylidene]-1H,5'H-[2,2']bipyrrolyl;

and pharmaceutically acceptable salts thereof.

Illustrative compounds of Formula (IV) are:

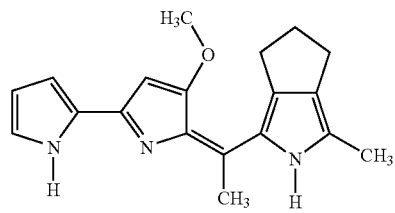

4'-Methoxy-5'-[1-(2,4,5,6-tetrahydro-cyclopenta[c]pyrrol-1-yl)-ethylidene]-1H, 5'H-[2,2']bipyrrolyl;

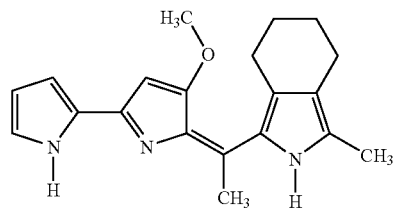

1-[1-(4-Methoxy-1'H-[2,2']bipyrrolyl-5-ylidene)-ethyl]-4,5,6,7-tetrahydro-2H-isoindole;

and pharmaceutically acceptable salts thereof.

An illustrative compound of Formula (VII) is:

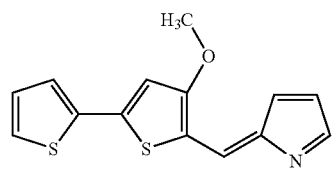

2-(4-Methoxy-[2,2']bithiophenyl-5-ylmethylene]-2H-pyrrole;

and pharmaceutically acceptable salts thereof.

Illustrative compounds of Formula (VIII) are:

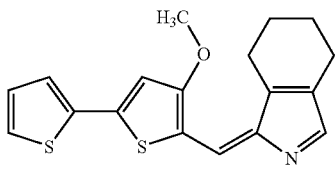

1-(4-Methoxy-[2,2']bithiophenyl-5-ylmethylene)-4,5,6,7-tetrahydro-1H-isoindole;

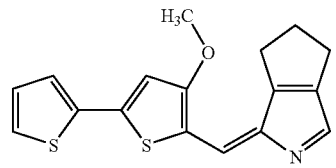

1-(4-Methoxy-[2,2']bithiophenyl-5-ylmethylene)-1,4,5,6-tetrahydro-cyclopenta[c]pyrrole;

and pharmaceutically acceptable salts thereof.

An illustrative compound of Formula (XI) is:

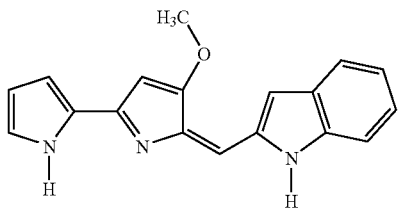

2-(4-Methoxy-1'H-[2,2']bipyrrolyl-5-ylidenemethyl)-1H-indole;

and pharmaceutically acceptable salts thereof.

5.16. Therapeutic/Prophylactic Administration and Compositions

As used herein, the novel compounds of the present invention, the compounds of the present compositions, the compounds of the present methods, and pharmaceutically acceptable salts of these compounds are referred to collectively herein as "Pyrrole-Type compounds".

Due to the activity of the Pyrrole-Type compounds, the Pyrrole-Type compounds are advantageously useful in veterinary and human medicine. For example, the Pyrrole-Type compounds are useful for the treatment or prevention of cancer or neoplastic disease or inhibiting the growth of a cancer cell or neoplastic cell. The Pyrrole-Type compounds are also useful for the treatment or prevention of a viral infection or inhibiting the replication or infectivity of a virus. The Pyrrole-Type compounds are also useful for causing immunosuppression. The Pyrrole-Type compounds are also useful for treating or preventing an autoimmune disease.

When administered to a subject, e.g., an animal for veterinary use or to a human for clinical use, or when made to contact a cell or tissue, the Pyrrole-Type compounds are preferably in isolated form. By "isolated" it is meant that prior to administration or contacting, a Pyrrole-Type compound is separated from other components of a synthetic organic chemical reaction mixture or natural product source, e.g., plant matter, tissue culture, bacterial broth, etc. Preferably, the Pyrrole-Type compounds are isolated via conventional techniques, e.g., extraction followed by chromatography, recrystalization, or another conventional technique. When in isolated form, the Pyrrole-Type compounds are at least 90%, preferably at least 95%, of a single Pyrrole-Type compound by weight of that which is isolated. "Single Pyrrole-Type compound" means an enantiomer or a racemate of a Pyrrole-Type compound.

The invention provides methods of treatment and prophylaxis by administration to a subject of an effective amount of a Pyrrole-Type compound. The subject is preferably an animal, including, but not limited to an animal such a cow, horse, sheep, pig, chicken, turkey, quail, cat, dog, mouse, rat, rabbit, guinea pig, etc., and is more preferably a mammal, and most preferably a human.

The present compositions, which comprise one or more Pyrrole-Type compounds, may be administered by any convenient route, for example by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a Pyrrole-Type compound of the invention. In certain embodiments, more than one Pyrrole-Type compound of the invention is administered to a subject. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer or viral infection).

In specific embodiments, it may be desirable to administer one or more Pyrrole-Type compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a viral infection, tissue or organ transplant, or autoimmune response.

In certain embodiments, it may be desirable to introduce one or more Pyrrole-Type compounds of the invention into the central nervous system by any suitable route, including intraventricular and intrathecal injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Pyrrole-Type compounds can be formulated as a suppository, with traditional binders and carriers such as triglycerides.

In another embodiment, the Pyrrole-Type compounds of the invention can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the Pyrrole-Type compounds can be delivered in a controlled release system. In one embodiment, a pump may be used (see Langer, supra; Sefton. CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled-release system can be placed in proximity of the target of the Pyrrole-Type compounds, e.g., the brain, thus requiring only a fraction of the systemic dose (see, e.g., Goodson, in Medical Applications of Controlled Release, supra, vol. 2, pp. 115–138 (1984)). Other controlled-release systems discussed in the review by Langer (Science 249:1527–1533 (1990)) may be used.

The present compositions will contain an effective amount of a Pyrrole-Type compound, preferably in purified form, together with a suitable amount of a pharmaceutically acceptable carrier so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which a Pyrrole-Type compound is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, auxiliary, stabilizing, thickening, lubricating and coloring agents may be used. When administered to a subject, the Pyrrole-Type compounds and pharmaceutically acceptable carriers are preferably sterile. Water is a preferred carrier when the Pyrrole-Type compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "Remington's Pharmaceutical Sciences" by E. W. Martin.

The phrase "pharmaceutically acceptable salt(s)," as used herein includes but are not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically or cosmetically acceptable salts with various amino acids, in addition to the acids mentioned above. Compounds, included in the present compositions, that are acidic in nature are capable of forming base salts with various pharmacologically or cosmetically acceptable cations. Examples of such salts include alkali metal or alkaline earth metal salts and, particularly, calcium, magnesium, sodium lithium, zinc, potassium, and iron salts.

In a preferred embodiment, the Pyrrole-Type compounds are formulated in accordance with routine procedures as a pharmaceutical composition adapted for intravenous administration to human beings. Typically, Pyrrole-Type compounds for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the Pyrrole-Type compound is to be administered by infusion, it can be dispensed, for example, with an infusion bottle containing sterile pharmaceutical grade water or saline. Where the Pyrrole-Type compound is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered Pyrrole-Type compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard carriers such as mannitol, lactose, starch, magnesium stearate, sodium saccharine, cellulose, magnesium carbonate, etc. Such carriers are preferably of pharmaceutical grade.

The amount of the Pyrrole-Type compound that will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for intravenous administration are generally about 10 micrograms–1 milligram, preferably about 20–500 micrograms of Pyrrole-Type compound per kilogram body weight. In specific preferred embodiments of the invention, the i.v. dose is 10–40, 30–60, 60–100, or 100–200 micrograms per kilogram body weight. In other embodiments, the i.v. dose is 75–150, 150–250, 250–375 or 375–500 micrograms per kilogram body weight. Suitable dosage ranges for intranasal administration are generally about 0.01 pg/kg body weight to 1 mg/kg body weight. Suppositories generally contain active ingredient in the range of 0.5% to 10% by weight. Oral compositions preferably contain 10% to 95% active ingredient. In specific preferred embodiments of the invention, suitable dose ranges for oral administration are generally about 0.1 micrograms–10 milligrams, preferably about 0.75 micrograms–1 milligram, and more preferably about 1–500 micrograms of active compound per kilogram body weight. In specific preferred embodiments, the oral dose is 1–10, 10–30, 30–90, or 90–150 micrograms per kilogram body weight. In other embodiments, the oral dose is 150–250, 250–325, 325–450 or 450–1000 micrograms per kilogram body weight. Effective doses may be extrapolated from dose-response curves derived from in vitro or animal model test systems. Such animal models and systems are well known in the art.

The invention also provides pharmaceutical packs or kits comprising one or more containers filled with one or more Pyrrole-Type compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In certain preferred embodiment, e.g., when administered for the treatment or prevention of cancer, the kit may also contain one or more chemotherapeutic agents useful for treating cancer or a neoplastic disease to be administered in combination with a Pyrrole-Type compound of the invention. In certain preferred embodiments, e.g., when administered for the treatment or prevention of viral or autoimmune disease, the kit may contain one or more Pyrrole-Type compound(s) of the invention and one or more anti-viral or immunosuppressant agents.

The Pyrrole-Type compounds of the invention are preferably assayed in vitro, and then in vivo, for the desired therapeutic or prophylactic activity, prior to use in humans. For example, in vitro assays can be used to determine whether administration of a specific Pyrrole-Type compound or combination of Pyrrole-Type compounds is preferred.

In one embodiment, a patient tissue sample is grown in culture, and contacted or otherwise administered with a Pyrrole-Type compound, and the effect of such Pyrrole-Type compound upon the tissue sample is observed and compared to a non-contacted tissue. In other embodiments, a cell culture model is used in which the cells of the cell culture are contacted or otherwise administered with a Pyrrole-Type compound, and the effect of such Pyrrole-Type compound upon the tissue sample is observed and compared to a non-contacted cell culture. Generally, a lower level of proliferation or survival of the contacted cells compared to the non-contracted cells indicates that the Pyrrole-Type compound is effective to treat a the patient. Such Pyrrole-Type compounds may also be demonstrated effective and safe using animal model systems.

Other methods will be known to the skilled artisan and are within the scope of the invention.

5.17. Inhibition of Cancer and Neoplastic Cells and Disease

The Pyrrole-Type compounds may be demonstrated to inhibit tumor cell proliferation, cell transformation and tumorigenesis in vitro and in vivo using a variety of assays known in the art, or described herein. Such assays may use cells of a cancer cell line, or cells from a patient. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and MRNA and activity can be determined by any method well known in the art. For example, protein can be quantitated by known immunodiagnostic methods such as Western blotting or immunoprecipitation using commercially available antibodies (for example, many cell cycle marker antibodies are from Santa Cruz Inc.). mRNA can be quantitated by methods that are well known and routine in the art, for example by northern analysis, RNase protection, the polymerase chain reaction in connection with the reverse transcription, etc. Cell viability can be assessed by using trypan-blue staining or other cell death or viability markers known in the art. Differentiation can be assessed visually based on changes in morphology, etc.

The present invention provides for cell cycle and cell proliferation analysis by a variety of techniques known in the art, including but not limited to the following:

As one example, bromodeoxyuridine (BRDU) incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., 1986, Int. J. Cancer 38, 369; Campana et al., 1988, J. Immunol. Meth. 107, 79).

Cell proliferation may also be examined using ($^3$H)-thymidine incorporation (see e.g., Chen, J., 1996, Oncogene 13:1395–403; Jeoung, J., 1995, J. Biol. Chem. 270:18367–73). This assay allows for quantitative characterization of S-phase DNA synthesis. In this assay, cells synthesizing DNA will incorporate ($^3$H)-thymidine into newly synthesized DNA. Incorporation may then be measured by standard techniques in the art such as by counting of radioisotope in a Scintillation counter (e.g. Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, Curr. Biol. 6:189–199; Vassilev et al., 1995, J. Cell Sci. 108:1205–15).

Cell proliferation may be measured by counting samples of a cell population over time (e.g daily cell counts). Cells may be counted using a hemacytometer and light microscopy (e.g. HyLite hemacytometer, Hausser Scientific). Cell number may be plotted against time in order to obtain a growth curve for the population of interest. In a preferred embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g. cells in S-phase) will exhibit a ploidy value higher than 2N and up to 4N DNA content. Ploidy value and cell-cycle kinetics may be further measured using propidum iodide assay (see e.g. Turner, T., et al., 1998, Prostate 34:175–81). Alternatively, the DNA ploidy may be determined by quantitation of DNA Feulgen staining (which binds to DNA in a stoichiometric manner) on a computerized microdensitometrystaining system (see e.g., Bacus, S., 1989, Am. J. Pathol.135:783–92). In an another embodiment, DNA content may be analyzed by preparation of a chromosomal spread (Zabalou, S., 1994, Hereditas. 120: 127–40; Pardue, 1994, Meth. Cell Biol. 44:333–351).

The expression of cell-cycle proteins (e.g., CycA. CycB, CycE, CycD, cdc2, Cdk4/6, Rb, p21, p27, etc.) provide crucial information relating to the proliferative state of a cell or population of cells. For example, identification in an anti-proliferation signaling pathway may be indicated by the induction of p21$^{cip1}$. Increased levels of p21 expression in cells results in delayed entry into G1 of the cell cycle (Harper et al., 1993, Cell 75:805–816; Li et al., 1996, Curr. Biol. 6:189–199). p21 induction may be identified by immunostaining using a specific anti-p21 antibody available commercially (e.g. Santa Cruz). Similarly, cell-cycle proteins may be examined by Western blot analysis using commercially available antibodies. In another embodiment, cell populations are synchronized prior to detection of a cell cycle protein. Cell cycle proteins may also be detected by FACS (fluorescence-activated cell sorter) analysis using antibodies against the protein of interest.

Detection of changes in length of the cell cycle or speed of cell cycle may also be used to measure inhibition of cell proliferation by the Pyrrole-Type compounds of the invention. In one embodiment the length of the cell cycle is determined by the doubling time of a population of cells (e.g., using cells contacted or not contacted with one or more Pyrrole-Type compounds of the invention). In another embodiment, FACS analysis is used to analyze the phase of cell cycle progression, or purify G1, S, and G2/M fractions (see e.g., Delia, D. et al., 1997, Oncogene 14:2137–47).

Lapse of cell cycle checkpoint(s), and/or induction of cell cycle checkpoint(s), may be examined by the methods described herein, or by any method known in the art. Without limitation, a cell cycle checkpoint is a mechanism which ensures that a certain cellular events occur in a particular order. Checkpoint genes are defined by mutations that allow late events to occur without prior completion of an early event (Weinert, T., and Hartwell, L., 1993, Genetics, 134:63–80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g. progression into mitosis without complete replication of the genomic DNA).

In addition to the effects of expression of a particular cell cycle protein, activity and post-translational modifications of proteins involved in the cell cycle can play an integral role in the regulation and proliferative state of a cell. The invention provides for assays involved in detecting post-translational modifications (e.g. phosphorylation) by any method known in the art. For example, antibodies that detect phosphorylated tyrosine residues are commercially available, and may be used in Western blot analysis to detect proteins with such modifications. In another example, modifications such as myristylation, may be detected on thin layer chromatography or reverse phase h.p.l.c. (see e.g., Glover, C., 1988, Biochem. J. 250:485–91; Paige, L., 1988, Biochem J.; 250:485–91).

Activity of signaling and cell cycle proteins and/or protein complexes is often mediated by a kinase activity. The present invention provides for analysis of kinase activity by assays such as the histone H1 assay (see e.g., Delia, D. et al., 1997, Oncogene 14:2137–47).

The Pyrrole-Type compounds can also be demonstrated to alter cell proliferation in cultured cells in vitro using methods which are well known in the art. Specific examples of cell culture models include, but are not limited to, for lung cancer, primary rat lung tumor cells (Swafford et al., 1997, Mol. Cell. Biol., 17:1366–1374) and large-cell undifferentiated cancer cell lines (Mabry et al., 1991, Cancer Cells, 3:53–58); colorectal cell lines for colon cancer (Park and Gazdar, 1996, J. Cell Biochem. Suppl. 24:131–141); multiple established cell lines for breast cancer (Hambly et al., 1997, Breast Cancer Res. Treat. 43:247–258; Gierthy et al., 1997, Chemosphere 34:1495–1505; Prasad and Church, 1997, Biochem. Biophys. Res. Commun. 232:14–19); a number of well-characterized cell models for prostate cancer (Webber et al., 1996, Prostate, Part 1, 29:386–394; Part 2, 30:58–64; and Part 3, 30:136–142; Boulikas, 1997, Anticancer Res. 17:1471–1505); for genitourinary cancers, continuous human bladder cancer cell lines (Ribeiro et al., 1997, Int. J. Radiat. Biol. 72:11–20); organ cultures of transitional cell carcinomas (Booth et al., 1997, Lab Invest. 76:843–857) and rat progression models (Vet et al., 1997, Biochim. Biophys Acta 1360:39–44); and established cell lines for leukemias and lymphomas (Drexler, 1994, Leuk. Res. 18:919–927, Tohyama, 1997, Int. J. Hematol. 65:309–317).

The Pyrrole-Type compounds can also be demonstrated to inhibit cell transformation (or progression to malignant phenotype) in vitro. In this embodiment, cells with a transformed cell phenotype are contacted with one or more Pyrrole-Type compounds, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, *General Virology,* 3d Ed., John Wiley & Sons, New York, pp. 436–446).

Loss of invasiveness or decreased adhesion may also be used to demonstrate the anti-cancer effects of the Pyrrole-Type compounds. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell-cell adhesion. Such E-cadherin-mediated adhesion can result in phenotypic reversion and loss of invasiveness (Hordijk et al., 1997, Science 278: 1464–66).

Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464–66).

Alternatively, loss of invasiveness may be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see e.g., Ohnishi, T., 1993, Biochem. Biophys. Res. Commun.193:518–25).

The Pyrrole-Type compounds can also be demonstrated to inhibit tumor formation in vivo. A vast number of animal models of hyperproliferative disorders, including tumorigenesis and metastatic spread, are known in the art (see Table 317-1, Chapter 317, "Principals of Neoplasia," in *Harrison's Principals of Internal Medicine,* 13th Edition, Isselbacher et al., eds., McGraw-Hill, New York, p. 1814, and Lovejoy et al., 1997, J. Pathol. 181:130–135). Specific examples include for lung cancer, transplantation of tumor nodules into rats (Wang et al., 1997, Ann. Thorac. Surg. 64:216–219) or establishment of lung cancer metastases in SCID mice depleted of NK cells (Yono and Sone, 1997, Gan To Kagaku Ryoho 24:489–494); for colon cancer, colon cancer transplantation of human colon cancer cells into nude mice (Gutman and Fidler, 1995, World J. Surg. 19:226–234), the cotton top tamarin model of human ulcerative colitis (Warren, 1996, Aliment. Pharmacol. Ther. 10 Supp 12:45–47) and mouse models with mutations of the adenomatous polyposis tumor suppressor (Polakis, 1997, Biochim. Biophys. Acta 1332:F127–F147); for breast cancer, transgenic models of breast cancer (Dankort and Muller, 1996, Cancer Treat. Res. 83:71–88; Amundadittir et al., 1996, Breast Cancer Res. Treat. 39:119–135) and chemical induction of tumors in rats (Russo and Russo, 1996, Breast Cancer Res. Treat. 39:7–20); for prostate cancer, chemically-induced and transgenic rodent models, and human xenograft models (Royai et al., 1996, Semin. Oncol. 23:35–40); for genitourinary cancers, induced bladder neoplasm in rats and mice (Oyasu, 1995, Food Chem. Toxicol 33:747–755) and xenografts of human transitional cell carcinomas into nude rats (Jarrett et al., 1995, J. Endourol. 9:1–7); and for hematopoietic cancers, transplanted allogeneic marrow in animals (Appelbaum, 1997, Leukemia 11 (Suppl. 4):S15–S17). Further, general animal models applicable to many types of cancer have been described, including, but not restricted to, the p53-deficient mouse model (Donehower, 1996, Semin. Cancer Biol. 7:269–278), the Min mouse (Shoemaker et al., 1997, Biochem. Biophys. Acta, 1332:F25–F48), and immune responses to tumors in rat (Frey, 1997, Methods, 12:173–188).

For example, a Pyrrole-Type compound can be administered to a test animal, preferably a test animal predisposed to develop a type of tumor, and the test animal subsequently examined for a decreased incidence of tumor formation in comparison with controls not administered the Pyrrole-Type compound. Alternatively, a Pyrrole-Type compound can be administered to test animals having tumors (e.g., animals in which tumors have been induced by introduction of malignant, neoplastic, or transformed cells, or by administration of a carcinogen) and subsequently examining the tumors in the test animals for tumor regression in comparison to controls not administered the Pyrrole-Type compound.

5.17.1. Treatment of Prevention of Cancer or a Neoplastic Disease in Combination with Chemotherapy or Radiotherapy Cancer or a neoplastic disease, including, but not limited to, neoplasms, tumors, metastases, or any disease or disorder characterized by uncontrolled cell growth, can be treated or prevented by administration of a composition comprising a pharmaceutically acceptable carrier and a Pyrrole-Type compound or a pharmaceutically acceptable salt thereof. The compositions can comprise one or more Pyrrole-Type compounds, or a pharmaceutically acceptable salt thereof.

In certain embodiments, one or more Pyrrole-Type compounds of the invention are used to treat or prevent cancer or neoplastic disease in combination with one or more anti-cancer, chemotherapeutic agents including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a preferred embodiment, one or more Pyrrole-Type compound of the invention is used to treat or prevent cancer or neoplastic disease in combination with one or more chemotherapeutic or other anti-cancer agents including, but not limited to, those presented in Table 1.

TABLE 1

| CHEMOTHERAPEUTICS AND OTHER ANTI-CANCER AGENTS | |
|---|---|
| Radiation: | γ-radiation |
| Alkylating agents | |
| Nitrogen mustards: | cyclophosphamide |
| | Ifosfamide |
| | trofosfamide |
| | Chlorambucil |
| Nitrosoureas: | carmustine (BCNU) |
| | Lomustine (CCNU) |
| Alkylsulphonates: | busulfan |
| | Treosulfan |
| Triazenes: | Dacarbazine |
| Platinum containing compounds: | Cisplatin |
| | carboplatin |
| Plant Alkaloids | |
| Vinca alkaloids: | vincristine |
| | Vinblastine |
| | Vindesine |
| | Vinorelbine |
| Taxoids: | paclitaxel |
| | Docetaxol |
| DNA Topoisomerase Inhibitors | |
| Epipodophyllins: | etoposide |
| | Teniposide |
| | Topotecan |
| | 9-aminocamptothecin |
| | campto irinotecan |
| | crisnatol |
| mytomycins: | |
| mytomycin C | Mytomycin C |
| Anti-metabolites | |
| Anti-folates: | |
| DHFR inhibitors: | methotrexate |
| | Trimetrexate |
| IMP dehydrogenase Inhibitors: | mycophenolic acid |
| | Tiazofurin |
| | Ribavirin |
| | EICAR |
| Ribonucleotide reductase Inhibitors: | hydroxyurea |
| | deferoxamine |
| Pyrimidine analogs: | |
| Uracil analogs | 5-Fluorouracil |
| | Floxuridine |
| | Doxifluridine |
| | Ratitrexed |
| Cytosine analogs | cytarabine (ara C) |
| | Cytosine arabinoside |
| | fludarabine |
| Purine analogs: | mercaptopurine |
| | Thioguanine |
| Hormonal therapies: | |
| Receptor antagonists: | |
| Anti-estrogens | Tamoxifen |
| | Raloxifene |
| | megestrol |
| LHRH agonists: | goserelin |
| | Leuprolide acetate |
| Anti-androgens: | flutamide |
| | bicalutamide |
| Retinoids/Deltoids | |
| Vitamin D3 analogs: | EB 1089 |
| | CB 1093 |
| | KH 1060 |
| Photodyamic therapies: | vertoporfin (BPD-MA) |
| | Phthalocyanine |
| | photosensitizer Pc4 |

TABLE 1-continued

| CHEMOTHERAPEUTICS AND OTHER ANTI-CANCER AGENTS | |
|---|---|
| | Demethoxy-hypocrellin A (2BA-2-DMHA) |
| Cytokines: | Interferon-α |
| | Interferon-γ |
| | Tumor necrosis factor |
| Others: | |
| Isoprenylation inhibitors: | Lovastatin |
| Dopaminergic neurotoxins: | 1-methyl-4-phenylpyridinium ion |
| Cell cycle inhibitors: | staurosporine |
| Actinomycins: | Actinomycin D |
| | Dactinomycin |
| Bleomycins: | bleomycin A2 |
| | Bleomycin B2 |
| | Peplomycin |
| Anthracyclines: | daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | verapamil |
| $Ca^{2+}$ ATPase inhibitors: | thapsigargin |

In other embodiments, a composition comprising one or more Pyrrole-Type compounds is administered along with radiation therapy and/or with one or a combination of chemotherapeutic agents, preferably with one or more chemotherapeutic agents with which treatment of the cancer has not been found to be refractory. The Pyrrole-Type compound can be administered to a patient that has also undergone surgery as treatment for the cancer.

In another specific embodiment, the invention provides a method to treat or prevent cancer that has shown to be refractory to treatment with a chemotherapy and/or radiation therapy.

In a specific embodiment, a composition comprising one or more Pyrrole-Type compounds is administered concurrently with chemotherapy or radiation therapy. In another specific embodiment, chemotherapy or radiation therapy is administered prior or subsequent to administration of a present composition, preferably at least an hour, five hours, 12 hours, a day, a week, a month, more preferably several months (e.g., up to three months), subsequent to administration of a therapeutic of the invention.

The chemotherapy or radiation therapy administered concurrently with, or prior or subsequent to, the administration of a present composition can be accomplished by any method known in the art. The chemotherapeutic agents are preferably administered in a series of sessions, any one or a combination of the chemotherapeutic agents listed above can be administered. With respect to radiation therapy, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, may also be administered to expose tissues to radiation.

Additionally, the invention provides methods of treatment of cancer or neoplastic disease with a present composition as an alternative to chemotherapy or radiation therapy where the chemotherapy or the radiation therapy has proven or may prove too toxic, e.g., results in unacceptable or unbearable side effects, for the subject being treated. The subject being treated with the present compositions may, optionally, be treated with other cancer treatments such as surgery, radiation therapy or chemotherapy, depending on which treatment is found to be acceptable or bearable.

5.17.2. Cancer and Neoplastic Disease Treatable or Preventable

Cancers or neoplastic diseases and related disorders that can be treated or prevented by administration of the present compositions include but are not limited to those listed in Table 2 (for a review of such disorders, see Fishman et al., 1985, *Medicine*, 2d Ed., J.B. Lippincott Co., Philadelphia):

TABLE 2

| CANCERS AND NEOPLASTIC DISORDERS |
|---|
| Leukemia |
|     acute leukemia |
|     acute lymphocytic leukemia |
|     acute myelocytic leukemia |
|         myeloblastic |
|         promyelocytic |
|         myelomonocytic |
|         monocytic |
|         erythroleukemia |
|     chronic leukemia |
|         chronic myelocytic (granulocytic) leukemia |
|         chronic lymphocytic leukemia |
| Polycythemia vera |
| Lymphoma |
|     Hodgkin's disease |
|     non-Hodgkin's disease |
| Multiple myeloma |
| Waldenstrom's macroglobulinemia |
| Heavy chain disease |
| Solid tumors |
|     sarcomas and carcinomas |
|         fibrosarcoma |
|         myxosarcoma |
|         liposarcoma |
|         chondrosarcoma |
|         osteogenic sarcoma |
|         chordoma |
|         angiosarcoma |
|         endotheliosarcoma |
|         lymphangiosarcoma |
|         lymphangioendotheliosarcoma |
|         synovioma |
|         mesothelioma |
|         Ewing's tumor |
|         leiomyosarcoma |
|         rhabdomyosarcoma |
|         colon carcinoma |
|         pancreatic cancer |
|         breast cancer |
|         ovarian cancer |
|         prostate cancer |
|         squamous cell carcinoma |
|         basal cell carcinoma |
|         adenocarcinoma |
|         sweat gland carcinoma |
|         sebaceous gland carcinoma |
|         papillary carcinoma |
|         papillary adenocarcinomas |
|         cystadenocarcinoma |
|         medullary carcinoma |
|         bronchogenic carcinoma |
|         renal cell carcinoma |
|         hepatoma |
|         bile duct carcinoma |
|         choriocarcinoma |
|         seminoma |
|         embryonal carcinoma |
|         Wilms' tumor |
|         cervical cancer |

TABLE 2-continued

| CANCERS AND NEOPLASTIC DISORDERS |
|---|
|         uterine cancer |
|         testicular tumor |
|         lung carcinoma |
|         small cell lung carcinoma |
|         bladder carcinoma |
|         epithelial carcinoma |
|         glioma |
|         astrocytoma |
|         medulloblastoma |
|         craniopharyngioma |
|         ependymoma |
|         pinealoma |
|         hemangioblastoma |
|         acoustic neuroma |
|         oligodendroglioma |
|         meningioma |
|         melanoma |
|         neuroblastoma |
|         retinoblastoma |

In specific embodiments, cancer, malignancy or dysproliferative changes (such as metaplasias and dysplasias), or hyperproliferative disorders, are treated or prevented in the ovary, breast, colon, lung, skin, pancreas, prostate, bladder, or uterus. In other specific embodiments, sarcoma, melanoma, or leukemia is treated or prevented.

In a highly preferred embodiment, the present compositions are used to treat or prevent cancers including prostate (more preferably hormone-insensitive), Neuroblastoma, Lymphoma (preferably follicular or Diffuse Large B-cell), Breast (preferably Estrogen-receptor positive), Colorectal, Endometrial, Ovarian, Lymphoma (preferably non-Hodgkin's), Lung (preferably Small cell), or Testicular (preferably germ cell).

In a preferred embodiment, the present compositions are used to inhibit the growth of a cell derived from a cancer or neoplasm such as prostate (more preferably hormone-insensitive), Neuroblastoma, Lymphoma (preferably follicular or Diffuse Large B-cell), Breast (preferably Estrogen-receptor positive), Colorectal, Endometrial, Ovarian, Lymphoma (preferably non-Hodgkin's), Lung (preferably Small cell), or Testicular (preferably germ cell).

In specific embodiments of the invention, the present compositions are used to inhibit the growth of a cell, said cell being derived from a cancer or neoplasm in Table 2 or herein.

5.17.3. Demonstration of Inhibition of Viruses and Viral Infections

The Pyrrole-Type compounds may be demonstrated to inhibit the replication or infectivity of a virus or a virus-infected cell in vitro or in vivo using a variety of assays known in the art, or described herein. In certain embodiments, such assays may use cells of a cell line, or cells from a patient. In specific embodiments, the cells may be infected with a virus prior to the assay, or during the assay. The cells may be contacted with a virus. In certain other embodiments, the assays may employ cell-free viral cultures.

In one embodiment, a Pyrrole-Type compound is demonstrated to have activity in treating or preventing viral disease by contacting cultured cells that exhibit an indicator of a viral reaction (e.g., formation of inclusion bodies) in vitro with the Pyrrole-Type compound, and comparing the level of said indicator in the cells contacted with the Pyrrole-Type compound with said level of said indicator in cells not so contacted, wherein a lower level in said contacted cells indicates that the Pyrrole-Type compound has activity in treating or preventing viral disease. Cell models that can be used for such assays include, but are not limited to, viral infection of T lymphocytes (Selin et al., 1996, J. Exp. Med. 183:2489–2499); hepatitis B infection of dedifferentiated hepatoma cells (Raney et al., 1997, J. Virol. 71:1058–1071); viral infection of cultured salivary gland epithelial cells (Clark et al., 1994, Autoimmunity 18:7–14); synchronous HIV-1 infection of CD4$^+$ lymphocytic cell lines (Wainberg et al., 1997, Virology 233:364–373); viral infection of respiratory epithelial cells (Stark et al., 1996, Human Gene Ther. 7:1669–1681); and amphotrophic retroviral infection of NIH-3T3 cells (Morgan et al., 1995, J. Virol. 69:6994–7000).

In another embodiment, a Pyrrole-Type compound can be demonstrated to have activity in treating or preventing viral disease by administering said Pyrrole-Type compound to a test animal having symptoms of a viral infection, such as characteristic respiratory symptoms in animal models, or which test animal does not exhibit a viral reaction and is subsequently challenged with an agent that elicits an viral reaction, and measuring the change in the viral reaction after the administration of said Pyrrole-Type compound, wherein a reduction in said viral reaction or a prevention of said viral reaction indicates that the Pyrrole-Type compound has activity in treating or preventing viral disease. Animal models that can be used for such assays include, but are not limited to, guinea pigs for respiratory viral infections (Kudlacz and Knippenberg, 1995, Inflamm. Res. 44:105–110); mice for influenza virus infection (Dobbs et al., 1996, J. Immunol. 157:1870–1877); lambs for respiratory syncitial virus infection (Masot et al., 1996, Zentralbl. Veterinarmed. 43:233–243); mice for neurotrophic virus infection (Barna et al., 1996, Virology 223:331–343); hamsters for measles infection (Fukuda et al., 1994, Acta Otolaryngol. Suppl (Stockh.) 514:111–116); mice for encephalomyocarditis infection (Hirasawa et al., 1997, J. Virol. 71:4024–4031); and mice for cytomegalovirus infection (Orange and Biron, 1996, J. Immunol. 156:1138–1142). In certain embodiments of the invention more than one Pyrrole-Type compound is administered to a test animal, virus, or viral-infected cell.

5.17.4. Viruses and Viral Infections

Viruses and viral infections that can be treated or prevented by administration of a composition of the invention include but are not limited to those listed in Table 3 including, but not limited to, DNA viruses such as hepatitis type B and hepatitis type C virus; parvoviruses, such as adeno-associated virus and cytomegalovirus; papovaviruses such as papilloma virus, polyoma viruses, and SV40; adenoviruses; herpes viruses such as herpes simplex type I (HSV-I), herpes simplex type II (HSV-II), and Epstein-Barr virus; poxviruses, such as variola (smallpox) and vaccinia virus; and RNA viruses, such as human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, picomaviruses such as poliomyelitis virus, coxsackieviruses, rhinoviruses, reoviruses, togaviruses such as rubella virus (German measles) and Semliki forest virus, arboviruses, and hepatitis type A virus.

In a preferred embodiment of the invention, the compositions of the invention are used to treat or prevent a viral infection associated with a virus as listed in Table 3. In another preferred embodiment, the compositions of the invention are used inhibit the replication or infectivity of a virus listed in Table 3. In yet another preferred embodiment, one or more Pyrrole-Type compounds of the invention are used inhibit the growth of a cell infected with a virus listed in Table 3.

TABLE 3

| | |
|---|---|
| Herpesviruses: | EBV |
| | HHV-8 (KSHV) |
| | Herpesvirus saimiri |
| Adenoviruses: | All strains |
| Retroviruses: | HIV-1 and 2 |
| | HTLV-I |
| Human Papillomaviruses: | HPV - all strains |
| Birnaviruses: | Infectious pancreatic necrosis virus |
| Other: | African Swine Fever virus (all strains) |

5.17.5. Immunosuppression and Treatment and Prevention of Autoimmune Diseases Many human diseases are characterized by excessive or inappropriate immune responses. Examples of such diseases include allergic reactions, auto-immune diseases, and rejection in allogeneic transplants, also known as "graft rejection." Allogeneic tissues and organs are tissues and organs from a genetically different member of the same species. "Graft rejection" occurs when a body's immune system attacks and destroys the transplanted tissue, for example in a heart, kidney, or bone marrow transplant, contains allogeneic. In these diseases, suppression of the immune response in a patient is beneficial, since the individual's immunological response causes more damage or discomfort than the invading microbes or foreign material. It is now recognized that immunosuppressive therapy is appropriate for treating each of these disorders (Blood Reviews, 1995, 9:117–133). The Pyrrole-Type compounds of the invention are useful for causing immunosuppression in a patient in need thereof. Accordingly, the Pyrrole-Type compounds of the invention are useful for treating or preventing allergies, autoimmune diseases, and rejection associated with an allogeneic transplant or "graft rejection."

In allergy, the immune system is hyper-responsive to otherwise harmless environmental antigens. Suppressing the immune system can alleviate the discomfort associated with the a body's excessive reaction to an otherwise harmless environmental antigen. Accordingly, the Pyrrole-Type compounds of the invention are useful for treating or preventing an allergy.

In autoimmune disease, the immune system attacks normal tissues. The immunological mechanisms become sensitized to some part of the individual's own body causing interference with or even destruction of that part. The ability to distinguish between "self" and "not self" antigens, which is vital to the functioning of the immune system as a specific defense against invading microorganisms, is impaired and the body begins to destroy itself. "Non-self" antigens are those antigens on substances in the body that are detectably different from or foreign to the body's own constituents. "Self" antigens are those antigens that are not detectably different from or foreign to the body's own constituents. In other cases, autoimmunity occurs as the result of trauma to an area usually not exposed to lymphocytes such as neural tissue or the lens of the eye. When the tissues in these areas become exposed to lymphocytes, their surface proteins can act as antigens and trigger the production of antibodies and cellular immune responses that then begin to destroy those tissues. Other autoimmune diseases develop after exposure of the individual to antigens that are antigenically similar to, that is cross-react with, the individual's own tissue. Rheumatic fever is an example of this type of disease, in which the antigen of a streptococcal bacterium, which causes rheumatic fever, is cross-reactive with parts of the human heart. Antibodies cannot differentiate between the bacterial antigens and the heart muscle antigens and accordingly, can destroy cells having either of those antigens. Suppression of the immune system would be useful for minimizing or eliminating the effects of autoimmune diseases. Accordingly, the Pyrrole-Type compounds of the invention are useful for treating or preventing autoimmune diseases.

Examples of autoimmune diseases that can be treated or prevented by administering the Pyrrole-Type compounds of the invention, include, but are not limited to, rheumatoid arthritis, insulin-dependent diabetes mellitus (which involves the autoimmune destruction of the β-cells of the islets of Langerhans which are responsible for the secretion of insulin), certain hemolytic anemias, rheumatic fever, thyroiditis, ulceractive colitis, myesthethia gravis, glomerulonephritis, allergic encephalomyelitis, continuing nerve and liver destruction that follows viral hepatitis, multiple sclerosis, systemic lupus erythematosus, juvenile diabetes, autoimmune haemolytic anaemia, psoriasis, idiopathic thrombocytopenic purpura, active chronic hepatitis, idiopathic leucopenia, primary biliary cirrhosis, thyrotoxicosis, dermatomyositis, discoid lupus erythematosus, psoriatic arthritis, regional enteritis, nephrotic syndrome, lupus nephritis, lupoid hepatitis, Sjogren's syndrome, Goodpasture's syndrome, Wegener's granulomatosis, scleroderma, Sezary's disease, uveitis, and mumps orchitis. In a more preferred embodiment, the Pyrrole-Type compounds of the invention are used to treat or prevent rheumatoid arthritis, systemic lupus erythematosus, juvenile diabetis, myesthethia gravis, multiple sclerosis, or psoriasis.

Similarly, when the body rejects allogenic transplants and suffers "graft rejection," it would be extremely useful to suppress the immune response in order to prevent the rejection of useful transplanted tissue or organs. Suppression of the immune response is useful for preventing rejection of allograft tissues and organs. Accordingly, the Pyrrole-Type compounds of the invention are useful for treating or preventing the rejection associated with allogeneic tissue and organ transplants.

6. EXAMPLES

6.1. Preparation of Compound 79

The preparation of Compound 79 generally involved the preparation of the boronic acid 8 of the 1-Boc pyrrole (73) and the corresponding triflate 78 (see Scheme 1 below). The Suzuki coupling of those two intermediates gave the desired product Compound 79 (4-methoxy-5-(1H-indol-2yl-methylene)-2,2'-bi-1H-pyrrole).

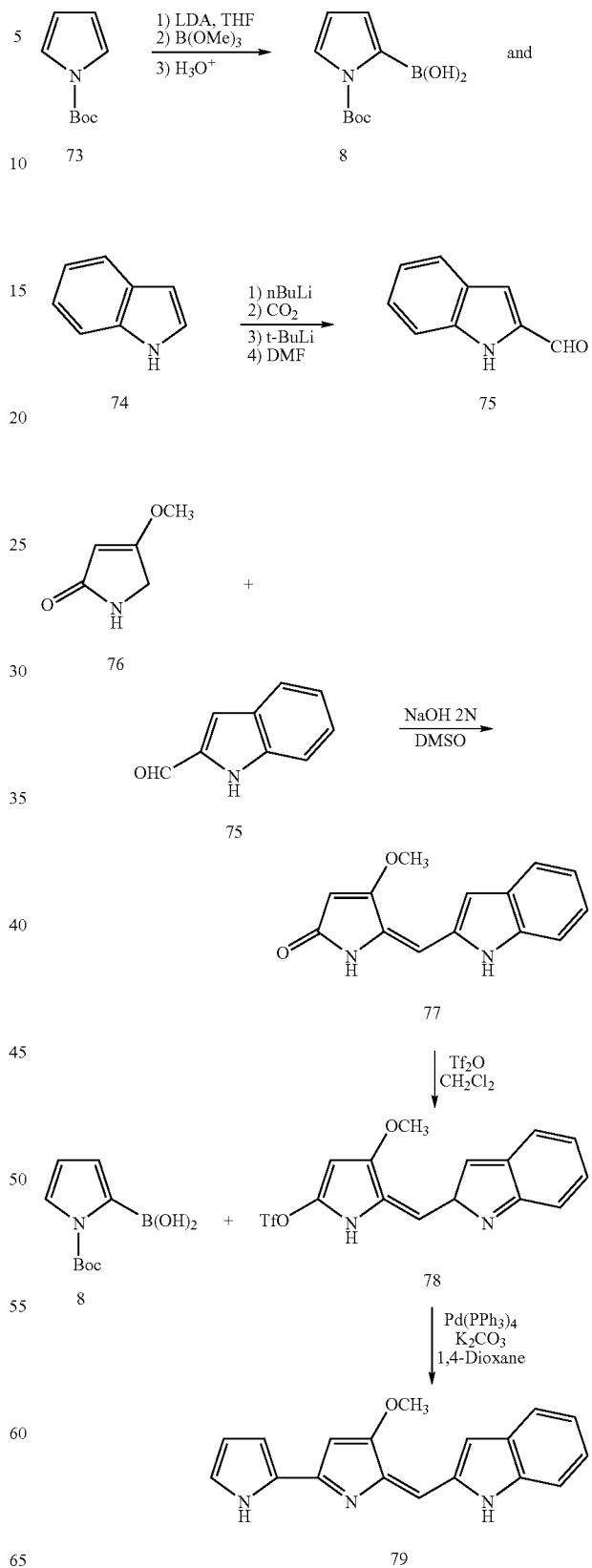

6.1.1. (1-tert-Butoxycarbonylpyrrol-2-yl)boronic acid, (8)

A solution of anhydrous diisopropylamine (3.35 mL, 23.9 mmol) was prepared in 100 mL of anhydrous THF and cooled at −78° C. A solution of 2.5 M of n-butyllithium (10.5 mL, 26.3 mmol) was slowly added to the THF solution over 10 minutes. The resulting mixture was stirred at −78° C. for 15 minutes and was then warmed to 0° C. for 15 minutes. The resulting mixture was cooled again at −78° C. and the tert-butyl 1-pyrrole carboxylate (73) (4.00 mL, 23.9 mmol) was added. The resulting solution was stirred for 1 hour at −78° C. and trimethyl borate (2.70 mL, 23.9 mmol) was added. The resulting solution was allowed to warm up to room temperature overnight. 20 mL of dilute HCl (0.25N) was added to the room temperature solution, which was stirred at room temperature for 15 minutes. The THF was removed under reduced pressure. The residue was extracted with diethyl ether (3×100 mL). The organic layer was dried over sodium sulfate, filtered and then concentrated in vacuo. Trituration with hexane (10 mL) and filtration gave the Compound 8 as beige solid (2.56 g, 51%). $^1$H NMR (500 MHz, CDCl$_3$): δ (ppm), 7.71 (s, 2H); 7.48 (t, 1H, J=2 Hz); 7.15 (t, 1H, J=1.8 Hz); 6.29 (t, 1H, J=3.1 Hz); 1.65 (3, 9H). $^{13}$C NMR (500 MHz, CDCl$_3$): δ (ppm), 153.22; 129.67; 127.92; 112.96; 86.47; 28.84.

6.1.2. Indole 2-carboxaldehyde, (75)

Indole (74) (1.00 g, 8.54 mmol) was dissolved in 50 mL of dry THF. The resulting solution was cooled at −78° C. A solution of 2.5 M of n-butyllithium (3.80 mL, 9.39 mmol) was slowly added to the THF solution and was stirred for 30 min. Carbon dioxide was passed through the reaction mixture over 10 min. The resulting solution was allowed to warm to room temperature. The excess of carbon dioxide was removed under reduced pressure while the solution was concentrated to 25 mL. 50 mL of dry THF was added to the concentrated solution, which was cooled again to −78° C. A solution of 1.7 M of tert-butyllithium (5.00 mL, 8.54 mmol) was slowly added to the THF solution, which was stirred at −78° C. for 1 hour. Anhydrous N,N-dimethylformamide (0.83 mL, 8.5 mmol) was added to the solution. The resulting mixture was warmed to room temperature over a period of 1.5 hours. Water (10 mL) was added and the mixture was stirred for 15 min. Diethyl ether was added. The organic layer was washed with brine (3×). The organic layer was dried over magnesium sulfate, filtered and concentrated in vacuo. The solid was purified over silica gel using 80/20 hexanes/ethyl acetate as eluent to give Compound 75, (0.7129 g, 58%). $^1$H NMR (500 MHz, CDCl$_3$): d (ppm), 9.88 (s, 1H); 7.77 (d, 1H, J=8.1 Hz); 7.48 (d, 1H, J=8.3 Hz); 7.41 (t, 1H, J=7.0 Hz); 7.3 (s, 1H); 7.20 (t, 1H, J=7.4 Hz). $^{13}$C NMR (500 MHz, CDCl$_3$): δ (ppm), 182.89; 138.80; 136.87; 128.25; 124.37; 122.20; 115.60; 113.28.

6.1.3. 4-Methoxy-5-(1H-indol-2-yl-methylene)-1,5-dihydro-2-pyrrol-2-one, (77)

To a solution of indole 2-carboxaldehyde (75) (0.1500 g, 1.033 mmol) and 4-methoxy-3-pyrrolin-2-one (76) (0.2330 g, 2.060 mmol) in DMSO (10 mL) were added 5 mL of a solution of 2N NaOH. The resulting mixture was stirred overnight at 60° C. The stirred mixture was allowed to cool to room temperature and then poured into 250 mL of water. The resulting yellow solid precipitate was filtered and dried in a dessicator to give Compound 77 (0.1257 g, 51%). $^1$H NMR (500 MHz, DMSO): δ (ppm), 11.14 (s, 1H); 9.69 (s, 1H); 7.49 (d, 1H, J=7.9 Hz); 7.34 (d, 1H, 8.1 Hz); 7.11 (t, 1H, J=7.4 Hz); 6.99 (m. 2H); 6.25 (s, 1H); 5.35 (s, 1H) 3.89 (s, 3H). $^{13}$C NMR (500 MHz, DMSO): δ (ppm) 172.47; 168.25; 138.41; 133.78; 131.53; 129.92; 123.80; 121.60; 120.98; 112.46; 105.91; 98.22; 93.71; 59.95.

6.1.4. 2-trifluoromethanesulfonyloxy-4-methoxy-5-(1H-indol-2-yl-methylene)-1H-pyrrole, (78)

To a solution of 77 (8.4 mg, 35 mol) in 5 mL of dry dichloromethane was added 1.1 equivalent of triluoromethanesulfonic anhydride at 0° C. The resulting solution was stirred at 0° C. for 5 min and was then poured into 5 mL of saturated aqueous NaHCO$_3$. The organic layer was dried over sodium sulfate, filtered and rapidly concentrated to give the crude triflate 78, which was used immediately, without further purification. $^1$H NMR (500 MHz, CD$_2$Cl$_2$): δ (ppm), 11.15 (s 1H); 7.72 (m, 3H); 7.61 (s, 1H); 7.50 (m, 1H), 7.20 (m, 1H); 6.01 (s, 1H); 4.16 (s, 3H).

6.1.5. 4-methoxy-5-(1H-indol-2-yl-methylene)-2,2'-bi-1H-pyrrole (79)

The crude triflate 78 was mixed with about 3 equivalent of boronic acid 8, 8 equivalents of potassium carbonate and about 0.1 equivalent of tetrakistriphenylphosphine palladium under argon. Anhydrous 1,4-dioxane (10 mL) was added to the reaction mixture, and it was heated at 90° C. in a sand bath. After three hours, the mixture was cooled and added to ethyl acetate (100 mL). The organic layer was washed with brine (3×100 mL) and was then dried over sodium sulfate, filtered and concentrated in vacuo. The resulting crude mixture was passed through a short column of neutral alumina using 50/50 hexanes/ethyl acetate as an eluent. The relevant fractions were combined and concentrated, and the resulting crude product was purified using a preparative plate of neutral alumina and eluted using 80/20 hexanes/ethyl acetate. The alumina band containing Compound 79 was washed with ethyl acetate and concentrated to provide the Compound 79 as a red dark solid (2 mg, 20%). (500 MHz, CD$_3$OD) : δ (ppm), 7.55 (m, 2H); 7.20 (t, 1H); 7.13 (s, 1H); 7.03 (t, 1H); 6.90 (s, 1H), 6.88 (s, 1H); 6.85 (s, 1H); 6.32 (s, 1H); 6.17 (s, 1H); 3.97 (s, 3H). MS (M+H): 290.0.

6.2. In Vitro Activity of Compound 79 (4-Methoxy-5-(1H-Indol-2YL-Methylene)-2,2'-BI-1H-Pyrrole)

Compound 79's selective toxicity to cancer cells by apoptosis is shown below.

6.2.1. Compound 79 Selectively Affects Cancer Cell Viability

Without being bound by theory, a marked decrease in mitochondrial ATP production is associated with progression towards irreversible cell dysfunction and death. To determine the effect of compound 79 (4-methoxy-5-(1H-indol-2yl-methylene)-2,2'-bi-1H-pyrrole) on cell viability, the cellular ATP levels were measured following compound 79 treatment. H1299 non-small cell lung carcinoma cells, C33A cervical carcinoma cells, Mrc-5 normal lung fibroblasts (American Type Culture Collection, Manassas, Va. USA) and HMEC normal mammary epithelial cells (Clonetics San Diego, Calif., USA) were cultured in the media recommended by the American Type Culture Collection.

The four cells lines were plated in 96-well microtiter plates (PerkinElmer Life Sciences Inc, Boston, Mass. USA) at a density that allowed them to reach confluence after 4 days of growth. One day after plating, the cells were treated with 10 µM Compound 79. 50 mM stock solutions of Compound 79 were prepared in dimethyl sulfoxide (Sigma-Aldrich Inc., St. Louis, Mo. USA), diluted in media and then added to the cells. The total dimethyl sulfoxide on the cells was 1%. After 3 days of incubation, the ATP levels in the cells were quantified using the luminescent VIALIGHT detection system (Bio Whittaker, MD, USA). The results were plotted relative to untreated control cells, which were set at 100 (FIG. 1).

The results shown in FIG. 1 demonstrate that a 72-hour treatment with 10 µM of compound 79 lowered the ATP levels of the cancer cell lines H1299 and C33A to a greater extent than the ATP levels of the normal cell lines HMEC and MRC-5. Therefore, Compound 79 is selectively toxic to cancer cells, particularly non-small cell lung carcinoma and cervical carcinoma cells.

6.2.2. Compound 79 Selectively Induces Apoptosis in Cancer Cells

To demonstrate the ability of the Compound 79 to trigger caspase activation, and, therefore, apoptosis, lysates of cells treated with various concentrations of Compound 79 were prepared. H1299 non-small cell lung carcinoma cells, C33A cervical carcinoma cells, Mrc-5 normal lung fibroblasts (American Type Culture Collection, Manassas, Va. USA) and HMEC normal mammary epithelial cells (Clonetics San Diego, Calif., USA) were maintained in media recommended by the American Type Culture Collection. Cells were harvested and suspended at $2.5–5 \times 10^5$ cells/ml in media. A 45 µL aliquot of cell suspension was added to each well of a 96-well microtiter plate (PerkinElmer Life Sciences Inc, Boston, Mass. USA). Cells were incubated overnight in a 5% $CO_2$-95% humidity incubator at 37° C. and then, 5 µL of a 10% dimethyl sulfoxide (Sigma-Aldrich Inc., St. Louis, Mo. USA) solution containing various concentrations of Compound 79 or 5 µL of 10% dimethyl sulfoxide (solvent control) were added. The plates were further incubated for 16 hr. Cells were lysed in lysis buffer (50 mM Hepes pH 7.4; 0.1% Chaps; 10 mM EDTA; 10 mM DTT) and set aside for caspase activity testing.

To demonstrate the caspase activity in the cell lysates, 0.35 µg of N-terminal biotinylated EGKRKGDEVDGVP-DRRASV peptide (Phoenix Pharmaceuticals Inc, Belmont, Calif. USA) were labeled with 1 mCi of [$^{32}$P]-γATP (PerkinElmer Life Sciences Inc, Boston, Mass. USA) using 250 units of Protein Kinase A catalytic subunit from bovine heart (Sigma-Aldrich Inc., St. Louis, Mo. USA) in 500 µL of HMK buffer (20 mM pH 7.5 Tris-HCl; 0.1 M NaCl; 12 mM $MgCl_2$; 1 mM DTT) at 37° C. for one hour. The reaction was then filtered using Sephadex G-10 Poly-Prep chromatography column (Amersham Biosciences, Inc, Piscataway, N.J., USA). The labeled peptide was coupled to 1.25 mL of streptavidin sepharose beads (Amersham Biosciences, Inc, Piscataway, N.J., USA) during 15 minutes at room temperature on a rotary mixer. The beads were washed seven times with 6 mL of 0.5 M NaCl in PBS and resuspended in a total volume of 7.25 mL of 0.5 M NaCl in PBS solution to which 9 mL of RPMI 1640 media (Bio Whittaker, MD, USA) was added. 96-well 0.45 µm MultiScreen-HV filter plates (Millipore, Bedford, Mass. USA) were then pre-wetted with 200 µL of 0.5 M NaCl in PBS and 40 µL of beads suspension was added to each well. Each well was washed five times with 200 µL of 0.5 M NaCl in PBS. In each well, 50 µL of cell lysate was added together with 12.5 µL of 0.5 M NaCl in 30% glycerol solution to each well. The plates were incubated at 30° C. with shaking at 220 rpm overnight. The next day, the filter plates containing the beads and the extract were centrifuged into of 96-well sample plates (PerkinElmer Life Sciences Inc, Boston, Mass. USA) containing 100 µL of Optiphase SuperMix liquid scintillant fluid (PerkinElmer Life Sciences Inc, Boston, Mass. USA) in each well and centrifuged at 1500 rpm for 10 minutes at room temperature. The number of radioactive counts per minute (cpm) in each well of the sample plate was measured using a liquid scintillation counter (PerkinElmer Life Sciences Inc, Boston, Mass. USA). The potency of caspase cascade activation was determined by the percentage increase in cpm in wells compared to cells treated only with dimethyl sulfoxide. Values 1.5-fold higher (150%) than control were considered positive and indicated that the compound triggered caspase activation in the cells, and, therefore, apoptosis.

The Compound 79 concentration required to positively activate caspases and, therefore, cause apoptosis in cancer cell lines was 250 µM and 125 µM for H1299- and C3AA-cancer cell lines, respectively (Table 4). However, in normal cell lines concentrations of greater than 500 µM are required to obtain such caspase activation (Table 4). These results demonstrate that caspases were activated in cancer cell lines but not in the normal cell line following 16 hours incubation with Compound 79. Accordingly, Compound 79 induces apoptosis selectively in cancer cells, particularly non-small cell lung carcinoma and cervical carcinoma cells.

TABLE 4

| | Concentration Required for Positive Caspase Activation (µM) | | | |
|---|---|---|---|---|
| | Cancer Cell Lines | | Normal Cell Lines | |
| Compound | H1299 | C33A | HMEC | MRC5 |
| 79 (4-methoxy-5-(1H-indol-2yl-methylene)-2,2'-bi-1H-pyrrole) | 250 | 125 | >500 | >500 |

The above example shows that an illustrative Pyrrole-Type Compound is selectively cytotoxic to cancer cells. This example also demonstrates that the Pyrrole-Type Compounds are useful for the treatment and prevention of cancer, particularly lung carcinoma and cervical carcinoma. This example further demonstrates that the Pyrrole-Type Compounds are useful for the inhibition of cancerous growth, particularly lung carcinoma growth and cervical carcinoma growth.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A compound of general Formula (VIII):

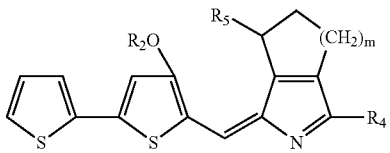

(VIII)

or a pharmaceutically acceptable salt thereof, wherein:
$R_2$ is a $C_1$–$C_{10}$ straight chain alkyl or —$CH_2C_6H_5$;
$R_4$ is —H or a $C_1$–$C_{10}$ straight chain alkyl;
$R_5$ is —H or a $C_1$–$C_{10}$ straight chain alkyl; and m is 1 to 4.

2. The compound of claim 1, wherein:
$R_2$ is —$CH_3$ or —$CH_2C_6H_5$;
$R_4$ and $R_5$ is —H or —$CH_3$; and
m is 2.

3. The compound of claim 2, wherein:
$R_2$ and $R_5$ is —$CH_3$;
$R_4$ is —H or —$CH_3$; and
m is 2.

4. A compound of general Formula (IX):

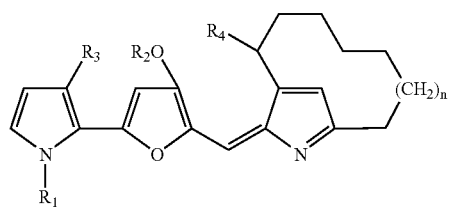

(IX)

or a pharmaceutically acceptable salt thereof, wherein:
$R_1$ is —H, —$CH_3$, —$SO_2$-4-methylphenyl, —$CH_2C_6H_5$, —$Si(R_5R_6R_7)$, —$CH_2OCH_2CH_2SiCH_3$, $C(O)OC(CH_3)_3$, or —$C(O)CH_2C_6H_5$;
$R_2$ is —$CH_3$, —$CH_2CH_3$, —$CH_2CH_2CH_3$, or —$CH_2C_6H_5$;
$R_3$ is —H or Cl;
$R_4$ is —H or a $C_1$–$C_{10}$ straight chain alkyl;
$R_5$ is a $C_1$–$C_4$ straight or branched chain alkyl or —$C_6H_5$;
$R_6$ is a $C_1$–$C_3$ straight or branched chain alkyl;
$R_7$ is a $C_1$–$C_3$ straight or branched chain alkyl; and
n is 1 to 5.

5. The compound of claim 4, wherein:
$R_1$ is —H;
$R_2$ is —$CH_3$ or —$CH_2C_6H_5$;
$R_3$ is —H;
$R_4$ is —H or a $C_1$–$C_4$ straight or branched chain alkyl; and
n is 1 to 3.

6. The compound of claim 5, wherein:
$R_1$ is —H;
$R_2$ is —$CH_3$;
$R_3$ is —H;
$R_4$ is —$C_4H_9$; and
n is 1.

7. The compound of claim 5, wherein:
$R_1$ is —H;
$R_2$ is —$CH_3$;
$R_3$ is —H;
$R_4$ is —$C_2H_5$; and
n is 3.

8. A compound of general Formula (X):

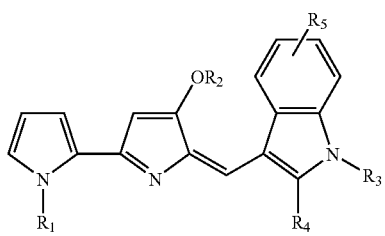

(X)

or a pharmaceutically acceptable salt thereof, wherein:
$R_1$ is —H, —$CH_3$, —$CH_2C_6H_5$, —$COCH_3$, —$C(O)OC(CH_3)_3$, or —$C(O)CH_2C_6H_5$;
$R_2$ is a $C_1$–$C_{10}$ straight chain alkyl or —$CH_2C_6H_5$, the —$CH_2C_6H_5$ being unsubstituted or substituted with one or more halo, methoxyl, methyl, methoxycarbonyl, or nitro groups;
$R_3$ is —H, —$CH_3$, —$CH_2C_6H_5$, or —$C(O)OC(CH_3)_3$;
$R_4$ is —H or —$CH_3$;
$R_5$ is —H, —$CH_3$, —$OCH_3$, —F, —Cl, —Br, —I, —CN, —$NH_2$; —$NH(C_1$–$C_3$ straight or branched chain alkyl), —$NHCOCH_3$, —$NO_2$, —COOH, —$COOR_6$, —OH, or —$OCH_2C_6H_5$; and
$R_6$ is a $C_1$–$C_6$ straight chain alkyl.

9. The compound of claim 8, wherein:
$R_1$ is —H;
$R_2$ is —$CH_3$ or —$CH_2C_6H_5$;
$R_3$ is —H;
$R_4$ is —H or —$CH_3$;
$R_5$ is —H, halogen, or —$COOR_6$; and
$R_6$ is —$CH_3$.

10. The compound of claim 9, wherein:
$R_1$ is —H;
$R_2$ is —$CH_3$;
$R_3$ is —H;
$R_4$ is —H or —$CH_3$; and
$R_5$ is —H.

11. A compound of general Formula (XI):

(XI)

or a pharmaceutically acceptable salt thereof, wherein:
$R_1$ is —H, —$CH_3$, —$CH_2C_6H_5$, —$COCH_3$, —$C(O)OC(CH_3)_3$, or —$C(O)CH_2C_6H_5$;
$R_2$ is a $C_1$–$C_{10}$ straight chain alkyl or —$CH_2C_6H_5$;
$R_3$ is —H, —$CH_3$, —$CH_2C_6H_5$, —$C(O)OC(CH_3)_3$, or —$C(O)CH_2C_6H_5$;
$R_4$ is —H or —$CH_3$;

R$_5$ is —H, a C$_1$–C$_{10}$ straight chain alkyl, —OR$_6$, —F, —Cl, —Br, —I, —CN, —COOH, —COOR$_6$, —NH$_2$; —NHCOR$_6$, —NO$_2$, —OH, or —OCH$_2$C$_6$H$_5$; and R$_6$ is a C$_1$–C$_6$ straight chain alkyl.

12. The compound of claim 11, wherein:
R$_1$ is —H;
R$_2$ is —CH$_3$ or —CH$_2$C$_6$H$_5$;
R$_3$ is —H;
R$_4$ is —H or —CH$_3$;
R$_5$ is —H, —CH$_3$, halogen, or COOR$_6$; and
R$_6$ is —CH$_3$.

13. The compound of claim 12, wherein:
R$_1$ is —H;
R$_2$ is —CH$_3$;
R$_3$ is —H;
R$_4$ is —CH$_3$; and
R$_5$ is —H or Cl.

14. A pharmaceutical composition comprising the compound of claim 1 and a pharmaceutically acceptable carrier.

15. A pharmaceutical composition comprising the compound of claim 2 and a pharmaceutically acceptable carrier.

16. A pharmaceutical composition comprising the compound of claim 3 and a pharmaceutically acceptable carrier.

17. A pharmaceutical composition comprising the compound of claim 4 and a pharmaceutically acceptable carrier.

18. A pharmaceutical composition comprising the compound of claim 5 and a pharmaceutically acceptable carrier.

19. A pharmaceutical composition comprising the compound of claim 6 and a pharmaceutically acceptable carrier.

20. A pharmaceutical composition comprising the compound of claim 7 and a pharmaceutically acceptable carrier.

21. A pharmaceutical composition comprising the compound of claim 8 and a pharmaceutically acceptable carrier.

22. A pharmaceutical composition comprising the compound of claim 9 and a pharmaceutically acceptable carrier.

23. A pharmaceutical composition comprising the compound of claim 10 and a pharmaceutically acceptable carrier.

24. A pharmaceutical composition comprising the compound of claim 11 and a pharmaceutically acceptable carrier.

25. A pharmaceutical composition comprising the compound of claim 12 and a pharmaceutically acceptable carrier.

26. A pharmaceutical composition comprising the compound of claim 13 and a pharmaceutically acceptable carrier.

27. The compound of claim 11, having the formula:

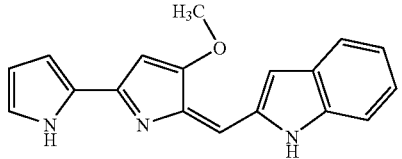

or a pharmaceutically acceptable salt thereof.

28. A pharmaceutical composition comprising the compound of claim 27 and a pharmaceutically acceptable carrier.

* * * * *